United States Patent
Kalla et al.

(10) Patent No.: US 7,317,017 B2
(45) Date of Patent: *Jan. 8, 2008

(54) $A_{2B}$ ADENOSINE RECEPTOR ANTAGONISTS

(75) Inventors: Rao Kalla, Mountain View, CA (US); Thao Perry, San Jose, CA (US); Elfatih Elzein, Fremont, CA (US); Vaibhav Varkhedkar, San Diego, CA (US); Xiaofen Li, Palo Alto, CA (US); Prabha Ibrahim, Mountain View, CA (US); Venkata Palle, Gurgaon (IN); Dengming Xiao, Longmont, CO (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/189,202

(22) Filed: Jul. 25, 2005

(65) Prior Publication Data

US 2005/0261316 A1  Nov. 24, 2005

Related U.S. Application Data

(63) Continuation of application No. 10/431,167, filed on May 6, 2003, now Pat. No. 6,977,300, which is a continuation-in-part of application No. 10/290,921, filed on Nov. 8, 2002, now Pat. No. 6,825,349.

(51) Int. Cl.
C07D 473/12 (2006.01)
C07D 473/06 (2006.01)
C07D 473/04 (2006.01)
A61K 51/522 (2006.01)
A61P 11/06 (2006.01)

(52) U.S. Cl. .................. 514/263.2; 514/263.22; 514/263.34; 544/267; 544/269; 544/270; 544/271; 544/272

(58) Field of Classification Search .......... 544/267, 544/269, 270, 271, 272; 514/263.2, 263.34, 514/263.22
See application file for complete search history.

(56) References Cited

U.S. PATENT DOCUMENTS 5,776,940 A * 7/1998 Daluge et al. ............ 544/271
6,825,349 B2 * 11/2004 Kalla et al. .............. 544/267
6,977,330 B2 * 12/2005 Santa Cruz et al. ......... 84/322
2003/0207879 A1 * 11/2003 Baraldi et al. .......... 514/228.5

OTHER PUBLICATIONS

Profire, Farmacia 1997 45(6) 55-68.*
Mazur, Farmatsevtichnii Zh. 1996 (3) 82-84.*
Priimenko, Ukrainskii Khimicheskii Zh. 62(7-8) 121-124.*
Klosa, Arch. Pharm. 1956 287, 211-217.*

* cited by examiner

Primary Examiner—Mark L. Berch
(74) Attorney, Agent, or Firm—J. Elin Hartrum; CV Therapeutics, Inc.

(57) ABSTRACT

Disclosed are novel $A_{2B}$ adenosine receptor antagonists having the structure of Formula I or Formula II

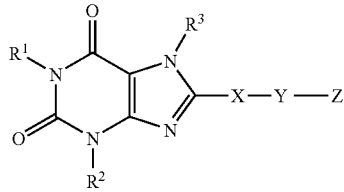
Formula I

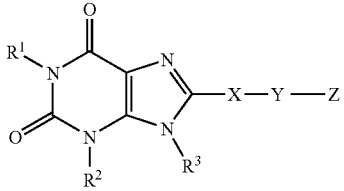
Formula II The compounds are particularly useful for treating asthma, inflammatory gastrointestinal tract disorders, cardiovascular diseases, neurological disorders, and diseases related to undesirable angiogenesis.

15 Claims, No Drawings

$A_{2B}$ ADENOSINE RECEPTOR ANTAGONISTS

This is a continuation of U.S. patent application Ser. No. 10/431,167, filed May 6, 2003, which issued as U.S. Pat. No. 6,977,300, which is a Continuation in Part of U.S. patent application Ser. No. 10/290,921, filed Nov. 8, 2002, which issued as U.S. Pat. No. 6,825,349, the complete disclosures of which are hereby incorporated by reference.

FIELD OF THE INVENTION

The present invention relates to $A_{2B}$ adenosine receptor antagonists, and to their use in treating mammals for various disease states, such as gastrointestinal disorders, immunological disorders, neurological disorders, and cardiovascular diseases due to both cellular hyperproliferation and apoptosis, and the like. The invention also relates to methods for the preparation of such compounds, and to pharmaceutical compositions containing them.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148-153), and $A_3$ adenosine receptors modulate cell proliferation processes.

Adenosine $A_{2B}$ receptors are ubiquitous, and regulate multiple biological activities. For example, adenosine binds to $A_{2B}$ receptors on endothelial cells, thereby stimulating angiogenesis. Adenosine also regulates the growth of smooth muscle cell populations in blood vessels. Adenosine stimulates $A_{2B}$ receptors on mast cells, thus modulating Type I hypersensitivity reactions. Adenosine also stimulates gastrosecretory activity by ligation with $A_{2B}$ in the intestine.

While many of these biological effects of adenosine are necessary to maintain normal tissue homeostasis, under certain physiological changes it is desirable to modulate its effects. For example, the binding of $A_{2B}$ receptors stimulates angiogenesis by promoting the growth of endothelial cells. Such activity is necessary in healing wounds, but the hyperproliferation of endothelial cells promotes diabetic retinopathy. Also, an undesirable increase in blood vessels occurs in neoplasia. Accordingly, inhibition of the binding of adenosine to $A_{2B}$ receptors in the endothelium will alleviate or prevent hypervasculation, thus preventing retinopathy and inhibibiting tumor formation.

$A_{2B}$ receptors are found in the colon in the basolateral domains of intestinal epithelial cells, and when acted upon by the appropriate ligand act to increase chloride secretion, thus causing diarrhea, which is a common and potentially fatal complication of infectious diseases such as cholera and typhus. $A_{2B}$ antagonists can therefore be used to block intestinal chloride secretion, and are thus useful in the treatment of inflammatory gastrointestinal tract disorders, including diarrhea.

Insensitivity to insulin exacerbates diabetes and obesity. Insulin sensitivity is decreased by the interaction of adenosine with $A_{2B}$ receptors. Thus, blocking the adenosine $A_{2B}$ receptors of individuals with diabetes or obesity would benefit patients with these disorders. It has also been demonstrated that $A_{2B}$-antagonists cause a reduction of blood glucose levels, and thus would be particularly useful in the treatment of type-II diabetes.

Another adverse biological effect of adenosine acting at the $A_{2B}$ receptor is the over-stimulation of cerebral IL-6, a cytokine associated with dementias and Altheimer's disease. Inhibiting the binding of adenosine to $A_{2B}$ receptors would therefore mitigate those neurological disorders that are produced by IL-6.

Type I hypersensitivtiy disorders, such as asthma, hay fever, and atopic ezcema, are stimulated by binding to $A_{2B}$-receptors of mast cells. Therefore, blocking these adenosine receptors would provide a therapeutic benefit against such disorders.

There are several compounds presently used in the treatment of asthma. For example, theophylline is an effective antiasthmatic agent, even though it is a poor adenosine receptor antagonist. However, considerable plasma levels are needed for it to be effective. Additionally, theophylline has substantial side effects, most of which are due to its CNS action, which provide no beneficial effects in asthma, and to the fact that it non-specifically blocks all adenosine receptor subtypes.

Additionally adenosine treatment, such as inhaled adenosine (or adenosine monophosphate), provokes bronchoconstriction in asthmatics, but not in the normal population. This process is known to involve mast cell activation, in that it releases mast cell mediators, including histamine, PGD2-β-hexosaminidase and tryptase, and because it can be blocked by specific histamine $H_1$ blockers and chromolyn sodium. Accordingly, there is an intrinsic difference in the way adenosine interacts with mast cells from asthmatics, and thus $A_{2B}$ antagonists are particularly useful in modulating mast cell function or in the activation of human lung cells.

Accordingly, it is desired to provide compounds that are potent $A_{2B}$ antagonists (i.e., compounds that inhibit the $A_{2B}$ adenosine receptor), fully or partially selective for the $A_{2B}$ receptor, useful in the treatment of various disease states related to modulation of the $A_{2B}$ receptor, for example cancer, asthma and diarrhea.

SUMMARY OF THE INVENTION

It is an object of this invention to provide $A_{2B}$ receptor antagonists. Accordingly, in a first aspect, the invention relates to compounds of Formula I and Formula II:

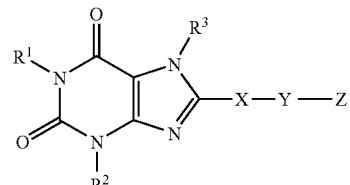

Formula I

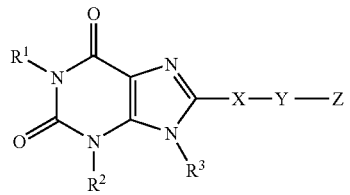

Formula II wherein:

$R^1$ and $R^2$ are independently chosen from hydrogen, optionally substituted alkyl, or a group -D-E, in which D is a covalent bond or alkylene, and E is optionally substituted alkoxy, optionally substituted cycloalkyl, optionally substituted aryl, optionally substituted heteroaryl, optionally substituted heterocyclyl, optionally substituted alkenyl or optionally substituted alkynyl, with the proviso that when D is a covalent bond E cannot be alkoxy;

$R^3$ is hydrogen, optionally substituted alkyl or optionally substituted cycloalkyl;

X is optionally substituted arylene or optionally substituted heteroarylene;

Y is a covalent bond or alkylene in which one carbon atom can be optionally replaced by —O—, —S—, or —NH—, and is optionally substituted by hydroxy, alkoxy, optionally substituted amino, or —COR, in which R is hydroxy, alkoxy or amino;

with the proviso that when the optional substitution is hydroxy or amino it cannot be adjacent to a heteroatom; and Z is optionally substituted monocyclic aryl or optionally substituted monocyclic heteroaryl; or Z is hydrogen when X is optionally substituted heteroarylene and Y is a covalent bond; with the proviso that when X is optionally substituted arylene, Z is optionally substituted monocyclic heteroaryl.

A second aspect of this invention relates to pharmaceutical formulations, comprising a therapeutically effective amount of a compound of Formula I or Formula II, or a mixture thereof, and at least one pharmaceutically acceptable excipient.

A third aspect of this invention relates to a method of using the compounds of Formula I and Formula II in the treatment of a disease or condition in a mammal that is amenable to treatment with an $A_{2B}$ receptor antagonist (i.e., inhibiting an adenosine receptor characterized as $A_{2B}$), comprising administering to a mammal in need thereof a therapeutically effective dose of a compound of Formula I or Formula II, or a mixture thereof. Such diseases include, but are not limited to, at least one of asthma, inflammatory gastrointestinal tract disorders, including diarrhea, cardiovascular diseases such as atherosclerosis, neurological disorders such as senile dementia, Alzheimer's disease, and Parkinson's disease, and diseases related to angiogenesis, for example diabetic retinopathy and cancer.

A fourth aspect of this invention relates to methods for preparing the compounds of Formula I and Formula II.

One preferred group of compounds of Formula I and II are those in which $R^1$ and $R^2$ are independently hydrogen, optionally substituted lower alkyl, or a group -D-E, in which D is a covalent bond or alkylene, and E is optionally substituted phenyl, optionally substituted cycloalkyl, optionally substituted alkenyl, or optionally substituted alkynyl, particularly those in which $R^3$ is hydrogen.

Within this group, a first preferred class of compounds include those in which $R^1$ and $R^2$ are independently lower alkyl optionally substituted by cycloalkyl, preferably n-propyl, and X is optionally substituted phenylene. Within this class, a preferred subclass of compounds are those in which Y is alkylene, including alkylene in which a carbon atom is replaced by oxygen, preferably —O—CH$_2$—, more especially where the oxygen is the point of attachment to phenylene. Within this subclass, it is preferred that Z is optionally substituted oxadiazole, particularly optionally substituted [1,2,4]-oxadiazol-3-yl, especially [1,2,4]-oxadiazol-3-yl substituted by optionally substituted phenyl or optionally substituted pyridyl.

A second preferred class of compounds include those in which X is optionally substituted 1,4-pyrazolene. Within this class, a preferred subclass of compounds are those in which Y is a covalent bond or alkylene, especially lower alkylene, and Z is hydrogen, optionally substituted phenyl, optionally substituted pyridyl, or optionally substituted oxadiazole. Within this subclass, one preferred embodiment includes compounds in which $R^1$ is lower alkyl optionally substituted by cycloalkyl, and $R^2$ is hydrogen. A more preferred embodiment includes those compounds in which Y is —(CH$_2$)— or —CH(CH$_3$)— and Z is optionally substituted phenyl, or Y is —(CH$_2$)— or —CH(CH$_3$)— and Z is optionally substituted oxadiazole, particularly 3,5-[1,2,4]-oxadiazole, or Y is —(CH$_2$)— or —CH(CH$_3$)— and Z is optionally substituted pyridyl. Within this subclass, also preferred are those compounds in which $R^1$ and $R^2$ are independently lower alkyl optionally substituted by cycloalkyl, especially n-propyl. More preferred are those compounds in which Y is a covalent bond, —(CH$_2$)— or —CH(CH$_3$)— and Z is hydrogen, optionally substituted phenyl, or optionally substituted pyridyl, particularly where Y is a covalent bond and Z is hydrogen.

At present, the preferred compounds are:
1-propyl-8-(1-{[3-(trifluoromethyl)phenyl]-methyl}pyrazol-4-yl)-1,3,7-trihydropurine-2,6-dione;
1-propyl-8-[1-benzylpyrazol-4-yl]-1,3,7-trihydropurine-2,6-dione;
1-butyl-8-(1-{[3-fluorophenyl]methyl}pyrazol-4-yl)-1,3,7-trihydropurine-2,6-dione;
1-propyl-8-[1-(phenylethyl)pyrazol-4-yl]-1,3,7-trihydropurine-2,6-dione;
8-(1-{[5-(4-chlorophenyl)(1,2,4-oxadiazol-3-yl)]methyl}pyrazol-4-yl)-1-propyl-1,3,7-trihydropurine-2,6-dione;
8-(1-{[5-(4-chlorophenyl)(1,2,4-oxadiazol-3-yl)]methyl}pyrazol-4-yl)-1-butyl-1,3,7-trihydropurine-2,6-dione;
1,3-dipropyl-8-pyrazol-4-yl-1,3,7-trihydropurine-2,6-dione;
1-methyl-3-sec-butyl-8-pyrazol-4-yl-1,3,7-trihydropurine-2,6-dione;
1-cyclopropylmethyl-3-methyl-8-{1-[(3-trifluoromethylphenyl)methyl]pyrazol-4-yl}-1,3,7-trihydropurine-2,6-dione;
1,3-dimethyl-8-{1-[(3-fluorophenyl)methyl]pyrazol-4-yl}-1,3,7-trihydropurine-2,6-dione;
3-methyl-1-propyl-8-{1-[(3-trifluoromethylphenyl)methyl]pyrazol-4-yl}-1,3,7-trihydropurine-2,6-dione;
3-ethyl-1-propyl-8-{1-[(3-trifluoromethylphenyl)methyl]pyrazol-4-yl}-1,3,7-trihydropurine-2,6-dione;
1,3-dipropyl-8-(1-{[3-(trifluoromethyl)phenyl]methyl}pyrazol-4-yl)-1,3,7-trihydropurine-2,6-dione;
1,3-dipropyl-8-{1-[(3-fluorophenyl)methyl]pyrazol-4-yl}-1,3,7-trihydropurine-2,6-dione;
1-ethyl-3-methyl-8-{1-[(3-fluorophenyl)methyl]pyrazol-4-yl}-1,3,7-trihydropurine-2,6-dione;
1,3-dipropyl-8-{1-[(2-methoxyphenyl)methyl]pyrazol-4-yl}-1,3,7-trihydropurine-2,6-dione;
1,3-dipropyl-8-(1-{[3-(trifluoromethyl)-phenyl]ethyl}pyrazol-4-yl)-1,3,7-trihydropurine-2,6-dione;
1,3-dipropyl-8-{1-[(4-carboxyphenyl)methyl]pyrazol-4-yl}-1,3,7-trihydropurine-2,6-dione;
2-[4-(2,6-dioxo-1,3-dipropyl(1,3,7-trihydropurin-8-yl))pyrazolyl]-2-phenylacetic acid;
8-{4-[5-(2-methoxyphenyl)-[1,2,4]oxadiazol-3-ylmethoxy]phenyl}-1,3-dipropyl-1,3,7-trihydropurine-2,6-dione;

8-{4-[5-(3-methoxyphenyl)-[1,2,4]oxadiazol-3-ylmethoxy] phenyl}-1,3-dipropyl-1,3,7-trihydropurine-2,6-dione;

8-{4-[5-(4-fluorophenyl)-[1,2,4]oxadiazol-3-ylmethoxy] phenyl}-1,3-dipropyl-1,3,7-trihydropurine-2,6-dione.

1-(cyclopropylmethyl)-8-[1-(2-pyridylmethyl)pyrazol-4-yl]-1,3,7-trihydropurine-2,6-dione;

1-n-butyl-8-[1-(6-trifluoromethylpyridin-3-ylmethyl)pyrazol-4-yl]-1,3,7-trihydropurine-2,6-dione;

8-(1-{[3-(4-chlorophenyl)(1,2,4-oxadiazol-5-yl)] methyl}pyrazol-4-yl)-1,3-dipropyl-1,3,7-trihydropurine-2,6-dione;

1,3-dipropyl-8-[1-({5-[4-(trifluoromethyl)phenyl]isoxazol-3-yl}methyl)pyrazol-4-yl]-1,3,7-trihydropurine-2,6-dione;

1,3-dipropyl-8-[1-(2-pyridylmethyl)pyrazol-4-yl]-1,3,7-trihydropurine-2,6-dione;

3-{[4-(2,6-dioxo-1,3-dipropyl-1,3,7-trihydropurin-8-yl) pyrazolyl]methyl}benzoic acid;

1,3-dipropyl-8-(1-{[6-(trifluoromethyl)(3-pyridyl)] methyl}pyrazol-4-yl)-1,3,7-trihydropurine-2,6-dione;

1,3-dipropyl-8-{1-[(3-(1H-1,2,3,4-tetraazol-5-yl)phenyl) methyl]pyrazol-4-yl}-1,3,7-trihydropurine-2,6-dione;

6-{[4-(2,6-dioxo-1,3-dipropyl-1,3,7-trihydropurin-8-yl) pyrazolyl]methyl}pyridine-2-carboxylic acid;

3-ethyl-1-propyl-8-[1-(2-pyridylmethyl)pyrazol-4-yl]-1,3,7-trihydropurine-2,6-dione;

8-(1-{[5-(4-chlorophenyl)isoxazol-3-yl]methyl}pyrazol-4-yl)-3-ethyl-1-propyl-1,3,7-trihydropurine-2,6-dione;

8-(1-{[3-(4-chlorophenyl)(1,2,4-oxadiazol-5-yl)] methyl}pyrazol-4-yl)-3-ethyl-1-propyl-1,3,7-trihydropurine-2,6-dione;

3-ethyl-1-propyl-8-(1-{[6-(trifluoromethyl)(3-pyridyl)] methyl}pyrazol-4-yl)-1,3,7-trihydropurine-2,6-dione;

1-(cyclopropylmethyl)-3-ethyl-8-(1-{[6-(trifluoromethyl) (3-pyridyl)]methyl}pyrazol-4-yl)-1,3,7-trihydropurine-2,6-dione; and 3-ethyl-1-(2-methylpropyl)-8-(1-{[6-(trifluoromethyl)(3-pyridyl)]methyl}pyrazol-4-yl)-1,3,7-trihydropurine-2,6-dione.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$) CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

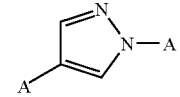

where A represents the point of attachment.

Unless otherwise constrained by the definition for the heteroaryl or heteroarylene substituent, such heteroaryl or hetarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$ R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I and Formula II" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is n-propyl, $R^2$ is n-propyl, $R^3$ is hydrogen, X is phenylene, Y is —O—($CH_2$), and Z is 5-(2-methoxyphenyl)-[1,2,4]-oxadiazol-3-yl,

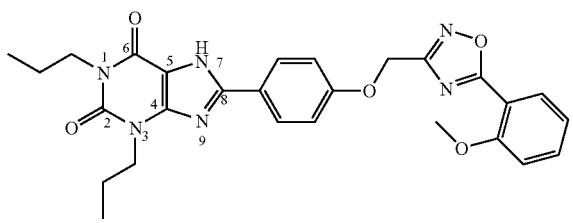

which is named:
8-{4-[5-(2-methoxyphenyl)-[1,2,4]-oxadiazol-3-yl-methoxy]-phenyl}-1,3-dipropyl-1,3,7-trihydropurine-2,6-dione.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I where $R^1$ and $R^2$ are the same, $R^3$ is hydrogen, and Y includes an oxygen, sulfur or nitrogen atom may be prepared as shown in Reaction Scheme I.

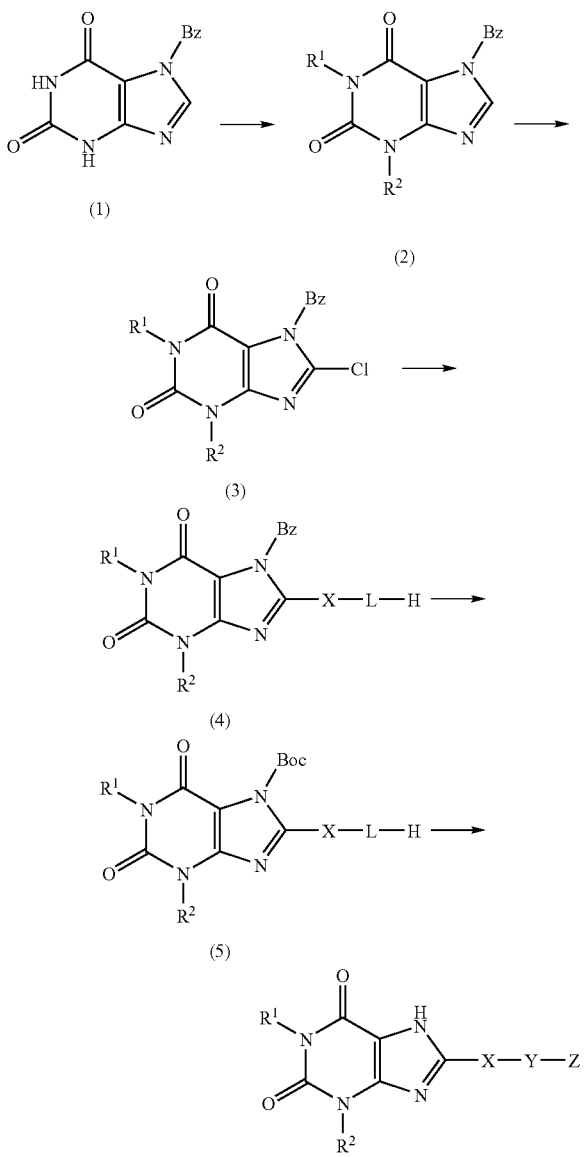

where Bz is benzyl, Boc is t-butyloxycarbonyl, and L is —O—, —S—, or —NH—.

Note that when $R^3$ is hydrogen, Formula I and II are the same compound as a consequence of tautomerism.

Step 1—Preparation of Formula (2)

The compound of formula (1), which is protected at the N-7 position, is commercially available, or may be prepared by means well known in the art (see, for example, Synthetic Communications, 20(16), 2459-2467 (1990)). The compound of formula (1) is reacted with at least two equivalents of a compound of formula $R^1LG$, where LG is a leaving group, preferably chlorine, bromine, or iodine, in the presence of a strong base, for example sodium hydride. The reaction is carried out in a polar solvent, for example DMF, initially at a temperature of about room temperature, followed by reaction at a temperature of about 30-100° C., for example about 70° C., for about 6-24 hours. When the reaction is substantially complete, the product of formula (2) is isolated by conventional means, for example by removal of the solvent under reduced pressure, followed by chromatography of the residue on silica gel.

It should be noted that this reaction only provides compounds of formula (2) in which $R^1$ and $R^2$ are the same. A procedure for preparing compounds of formula (2) in which $R^1$ and $R^2$ are different is shown below in Reaction Scheme III.

A different synthesis is required for the preparation of compounds of formula (2) in which $R^1$ and/or $R^2$ are aryl or heteroaryl groups, and is shown in Reaction Scheme III.

Step 2—Preparation of Formula (3)

The compound of formula (2) is then halogenated at the 8-position, to give a compound of formula (3), by reaction with a halogenating agent, for example N-chlorosuccinimide, to give the 8-chloro compound of formula (3). In general, the compound of formula (2) is dissolved in an inert solvent, for example tetrahydrofuran, and N-bromosuccinimide (or N-chlorosuccinimide) is added. The reaction is carried out at a temperature of about 0-30° C., for example about room temperature, for about 1-10 hours, for example about 4 hours. When the reaction is substantially complete, the product of formula (3) is isolated by conventional means, and recrystallized.

Step 3—Preparation of Formula (4)

The compound of formula (3) is then converted to a compound of formula (4) by reaction with an appropriately substituted boronic acid derivative in the presence of a palladium(0) complex. For example, where X is optionally substituted phenyl, the compound of formula (3) is reacted with an optionally substituted phenylboronic acid. The reaction is carried out in an inert solvent, for example toluene/ethanol, in the presence of aqueous sodium carbonate solution and tetrakis(triphenylphosphine)-palladium(0), at about reflux temperature for about 24 hours. When the reaction is substantially complete, the product of formula (4) is isolated by conventional means, for example by removing the solvent under reduced pressure, followed by chromatography of the residue on silica gel.

Step 4—Preparation of Formula (5)

a) The benzyl protecting group of the compound of formula (4) is then replaced by Boc, to give the compound of formula (5). In general, the compound of formula (4) is dissolved in an inert solvent, for example methanol, and a hydrogenation catalyst added. The reaction is stirred under an atmosphere of hydrogen, at a temperature of about 0-30° C., for example about room temperature, for about 8-24 hours, for example about 18 hours. When the reaction is substantially complete, the catalyst is removed by filtration, and the product isolated by conventional means.

b) The product is then dissolved in an inert solvent, for example methanol, to which was added an excess of di t-butyldicarbonate and a hindered base, for example ethyldiisopropylamine. The mixture is refluxed for about 8-24 hours, for example about 18 hours. When the reaction is substantially complete, the catalyst is removed by filtration, and the compound of formula (5) isolated by conventional means, for example by removing the solvent under reduced pressure, followed by chromatography of the residue on silica gel.

Step 5—Preparation of Formula I where $R^3$ is Hydrogen

The compound of formula (5) is then converted to a compound of Formula I by reaction with a compound of the formula Z-Y-LG, where Z and Y are as defined above and LG is a leaving group, preferably a halogen, more preferably chloro (the Boc protecting group is removed simultaneously). The reaction is carried out in the presence of a strong base, for example sodium hydride, in an inert polar solvent, preferably DMF, at a temperature of about 0-30° C., preferably about room temperature, for about 8-24 hours, preferably about 16 hours. The BOC protecting group is also removed in this reaction sequence. When the reaction is substantially complete, the product of Formula I where $R^3$ is hydrogen is isolated by conventional means, for example by chromatography on silica gel.

Step 5—Preparation of Formula I where $R^3$ is other than Hydrogen

A compound of Formula I in which $R^3$ is hydrogen may be converted to a compound of Formula I in which $R^3$ is not hydrogen by reaction with a compound of formula R3-LG, where LG is a leaving group, preferably iodo or bromo. The reaction is carried out in the presence of a mild base, for example potassium carbonate, in an inert polar solvent, preferably DMF, at a temperature of about 30-100° C., preferably about 70° C., for about 8-24 hours, preferably about 16 hours. When the reaction is substantially complete, the product of Formula I where $R^3$ is other than hydrogen is isolated by conventional means, for example by chromatography on silica gel.

Alternatively, the benzyl protecting group of formula (4) may be replaced by a trimethylsilyl-ethoxymethyl protecting group (instead of a BOC group), the subsequent removal of which can be accomplished under milder reaction conditions. In general, the product of Step 4a is dissolved in an inert solvent, preferably anhydrous DMF (100 mL), and reacted with trimethylsilyl-ethoxymethyl chloride in the presence of a base, preferably potassium carbonate. The reaction is conducted at a temperature of about 50-90° C., preferably about 70° C., for about 1-6 days, preferably about 72 hours. When the reaction is substantially complete, the catalyst is removed by filtration, and the product isolated by conventional means, preferably flash chromatography.

The product is then reacted with Z-Y-LG, where Z and Y are as defined above and LG is a leaving group, as shown in step 5 above. The trimethylsilyl-ethoxymethyl protecting group is removed from the resulting intermediate compound by treatment by acid in a protic solvent, preferably hydrochloric acid in ethanol, to give a compound of Formula I.

Alternatively, the benzyl group of the starting material of formula (1) can be replaced by BOC before the halogenation of step 2. In this manner, there is no need to change the protecting group from benzyl to BOC as outlined above in step 4.

An alternative method for preparing the compounds of Formula I where $R^3$ is hydrogen, Z is an optionally substituted 1,2,4-oxadiazole, and preferably Y is oxygen, is shown in Reaction Scheme II.

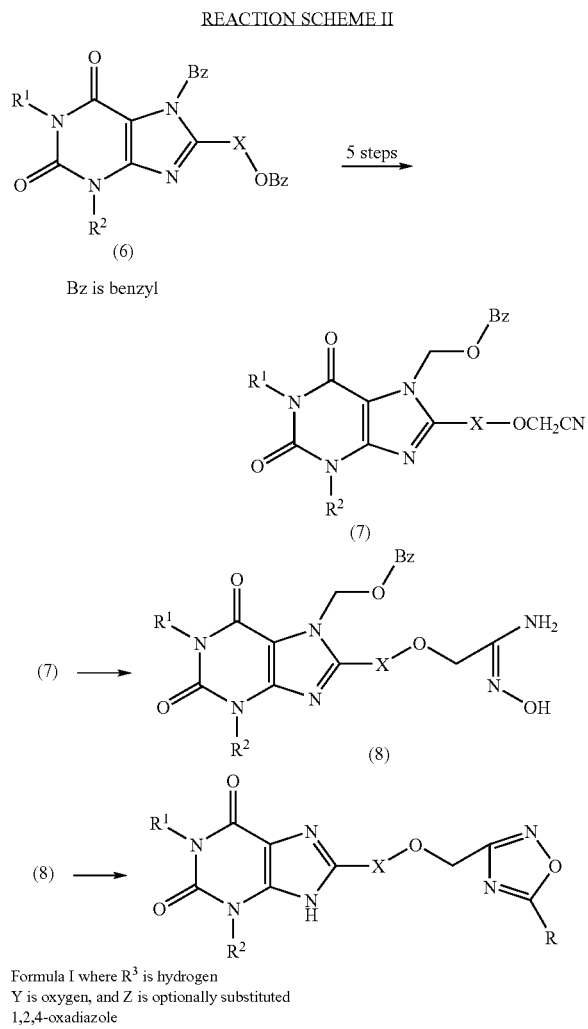

Formula I where $R^3$ is hydrogen
Y is oxygen, and Z is optionally substituted
1,2,4-oxadiazole Step 1—Preparation of Formula (7)

The compound of formula (6) is prepared in a manner similar to that shown above for compound (4). It is deprotected by treatment with hydrogen in the presence of a catalyst, preferably Pd on carbon. The hydroxy compound thus produced is reacted with tert-butyldimethylsilyl chloride in the presence of imidazole to give the tert-butyldimethylsilyloxy derivative. This compound is reacted with sodium hydride, and the anion thus produced is reacted with benzyloxymethyl chloride to provide a compound that is protected at the N-7 position by benzyloxymethyl. The tert-butyldimethylsilyl protecting group is then removed by the usual means, for example treatment with tetrabutylammonium fluoride, and the resulting hydroxy compound is reacted with iodoacetonitrile or chloroacetonitrile, in the presence of a strong base, for example potassium t-butoxide. The reaction is carried out in an inert solvent, preferably tetrahydrofuran at about room temperature, for about 6-24 hours. When the reaction is substantially complete, the product of formula (7) is isolated by conventional means, for example by removal of the solvent under reduced pressure, followed by chromatography of the residue on silica gel.

Step 2—Preparation of Formula (8)

The compound of formula (7) is then reacted with hydroxylamine hydrochloride. In general, the compound of formula (7) is dissolved in an inert solvent, for example ethanol, and hydroxylamine hydrochloride is added, along with an equivalent amount of a strong base, for example sodium ethoxide. The reaction is carried out at a temperature of about 0-30° C., for example about room temperature, for about 6-24 hours. When the reaction is substantially complete, the product of formula (8) is isolated by conventional means, for example by removal of the solvent under reduced pressure, followed by chromatography of the residue on silica gel.

Step 3—Preparation of Formula I

The compound of formula (8) is then cyclized to an optionally substituted 1,2,4-oxadiazole of Formula I by reaction with an appropriately substituted acid chloride of formula RC(O)Cl, in which R represents an optional substitution that leads to 5-substitution on the oxadiazole ring. In general, the compound of formula (8) is dissolved in an inert solvent, for example dioxane, and potassium carbonate and the acid chloride added. The mixture is allowed to react for about 10 minutes at a temperature of about 0-30° C., preferably about room temperature. When the reaction is substantially complete, the intermediate is isolated conventionally, and dissolved in a high boiling inert solvent, for example xylene. The mixture is reacted for about 6-24 hours, at a temperature of about 100-160° C., preferably about 145° C. The product of Formula I is isolated by conventional means, for example by removal of the solvent under reduced pressure, followed by chromatography of the residue on silica gel.

A method for preparing compounds of Formula I in which $R^1$ and $R^2$ are not the same is shown in Reaction Scheme III.

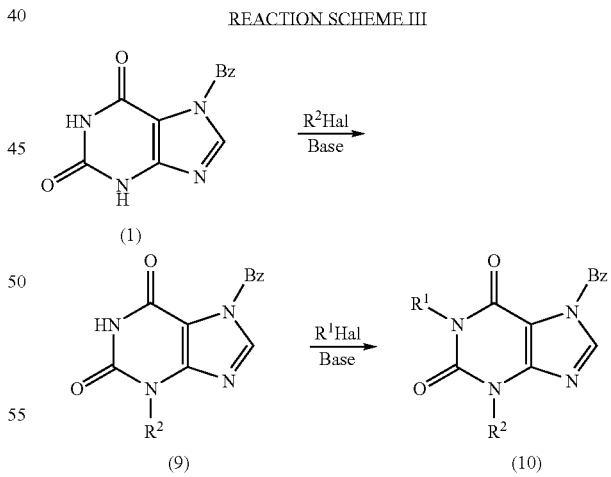

where $R^1$ and $R^2$ are as defined above, Bz is benzyl, and Hal is chloro, bromo, or iodo.

In general, the procedure is carried out as described in Synthetic Communications, 20(16), 2459-2467 (1990). The reaction scheme takes advantage of the fact that xanthines are well known to react with alkylating agents in the order N3>N7>N1. With N7 protected, as in the compound of formula (1), reaction with a compound of formula $R^2$LG, where LG is a leaving group, preferably chlorine, bromine, or iodine, with a slight excess of $R^2LG$ in the same manner as shown above for the preparation of a compound of formula (2) provides the compound of formula (9). Further reaction of (9) with a compound of formula $R^2LG$ provides the compound of formula (10) in which $R^1$ and $R^2$ are different.

A method for preparing compounds of formula (2) in which $R^2$ is hydrogen or alkyl and $R^1$ is aryl or heteroaryl is shown in Reaction Scheme IV.

REACTION SCHEME IV

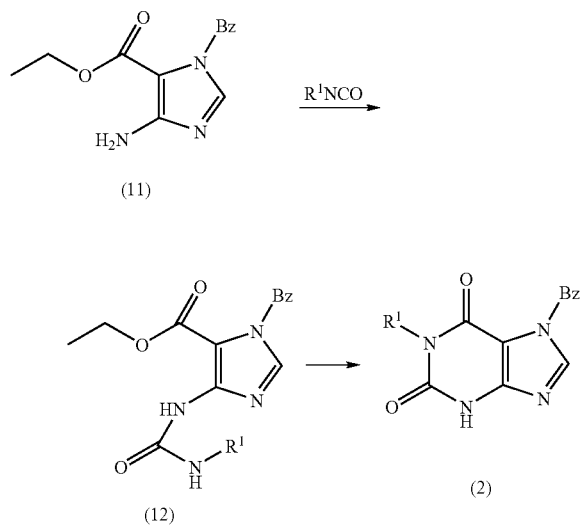

The compounds of formula (2) in which $R^1$ is aryl or heteroaryl may be prepared as described in *Synthesis*, 1995, p855-858. In general, a compound of formula (11), prepared by means well known in the art, is reacted with an appropriately substituted isocyanate of formula $R^1NCO$ to provide a compound of formula (12), which is cyclized under basic conditions, for example treatment with sodium ethoxide, to provide a compound of formula (2) in which $R^1$ is aryl or heteroaryl and $R^2$ is hydrogen. This method can also be used to provide compounds in which $R^1$ is alkyl etc.

The compound of formula (2) in which $R^2$ is hydrogen can then be further reacted with an alkyl halide of formula $R^2$hal in the same manner as shown in Reaction Scheme I to provide a compound of formula (2) in which $R^1$ is aryl or heteroaryl and $R^2$ is alkyl.

Compounds of formula (2) in which $R^1$ and $R^2$ are both aryl or heteroaryl are prepared as shown in Chem. Ber., GE; 111; 1978; 982-995.

A method for preparing compounds of Formula I in which $R^3$ is not hydrogen is shown in Reaction Scheme V.

REACTION SCHEME V

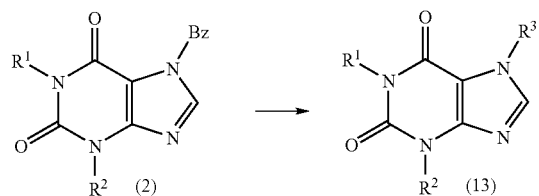

Preparation of Formula (13)

The benzyl protecting group of the compound of formula (2) is removed by hydrogenation as described in Reaction Scheme I, step 4. The resulting compound is then reacted with a compound of formula $R^3LG$, where LG is a leaving group, preferably chlorine, bromine, or iodine, in the presence of a base, for example potassium carbonate. The reaction is carried out in a polar solvent, for example DMF, initially at a temperature of about room temperature, followed by reaction at a temperature of about 30-100° C., for example about 70° C., for about 6-24 hours. When the reaction is substantially complete, the product of formula (13) is isolated by conventional means, for example by removal of the solvent under reduced pressure, followed by chromatography of the residue on silica gel.

The reaction is disclosed in more detail in J. Med. Chem., 1999, 42, 2527-2534.

An alternative method for preparing compounds of Formula I is shown in Reaction Scheme VI. Coupling of the 8-chloro derivative of formula (14) with a compound of formula $(HO)_2B$—X—Y-Z is a convenient method for providing compounds of Formula I without a heteroatom in the chain.

REACTION SCHEME VI

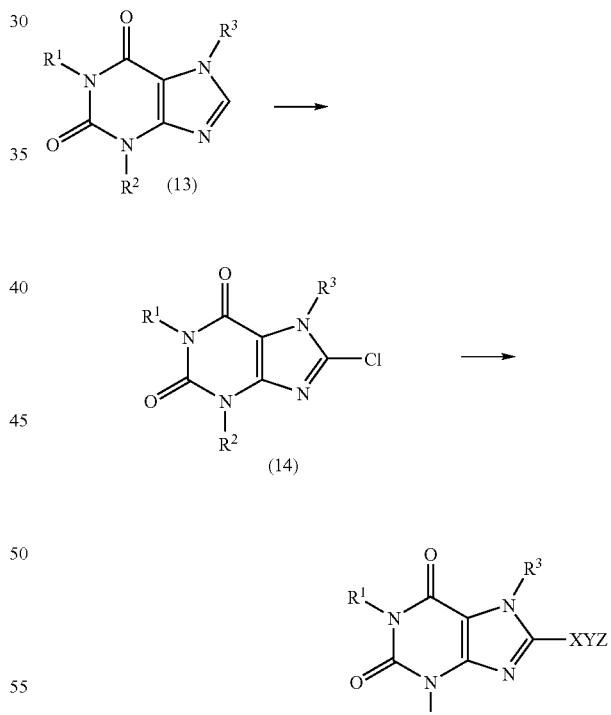

Formula 1

Preparation of a Compound of Formula II

The preparation of a compound of Formula II is carried out in the same manner as shown above in Reaction Scheme I, II and III, starting with a compound of the formula (18), the preparation of which is shown in Reaction Scheme VII

REACTION SCHEME VII

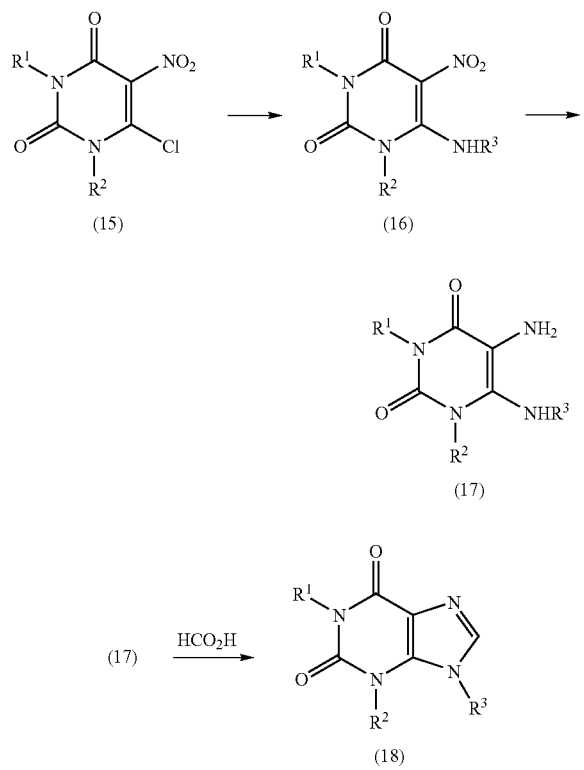

Similar reaction sequences are disclosed in U.S. Pat. No. 5,631,260, the complete disclosure of which is hereby incorporated by reference.

It should be noted that if $RCO_2H$ (or $RCOCl$) is used in place of formic acid, a compound of formula (18) that is substituted at the 8-position by R will result. Thus, if $RCO_2H$ is equivalent to $ZYXCO_2H$ (a compound of formula (22)), an alternative synthesis of a compound of Formula II can be accomplished, as shown in Reaction Schee VIII.

REACTION SCHEME VIII

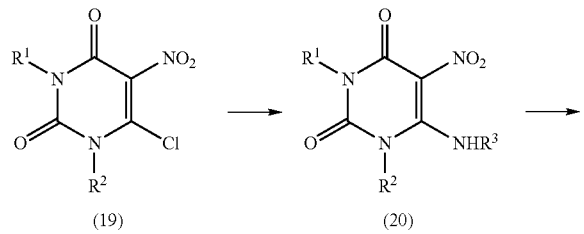

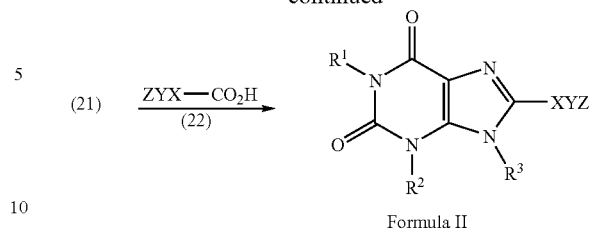

It should be noted that if $R^3$ is hydrogen, a compound of Formula I or II is produced.

The compound of formula (19) is commercially available, or is prepared by means well known in the art. It is converted into a compound of Formula II (or a compound of Formula I when $R^3$ is hydrogen) as described in U.S. Pat. No. 5,446,046, the complete disclosure of which is hereby incorporated by reference.

The compound of formula (21) in which $R^3$ is hydrogen may be purchased from a commercial source, for example 5,6-diamino-1,3-dipropyluracil, or prepared by means well known in the art.

A similar reaction can be carried out starting with a nitroso amino derivative of the formula (24).

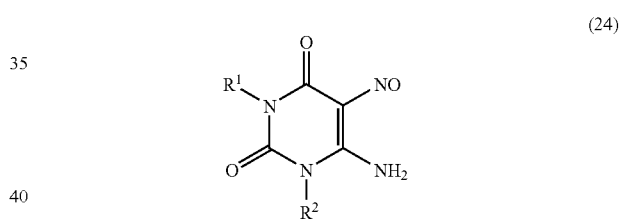

Reduction of the compound of formula (24) with hydrogen/platinum oxide catalyst provides the corresponding diamino compound (21) in which $R^3$ is hydrogen. Alternatively, the compound of formula (24) can be first substituted with $R^3$ as described in Reaction Scheme VII above, to provide the corresponding diamino compound of formula (21) where $R^3$ is other than hydrogen.

Alternatively, a compound of formula (24) in which $R^2$ is hydrogen and $R^1$ is other than hydrogen can be converted to a compound of Formula I in which $R^2$ is hydrogen and $R^1$ is other than hydrogen as shown in Reaction Scheme IX.

REACTION SCHEME IX

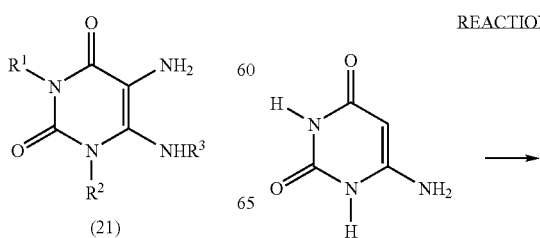

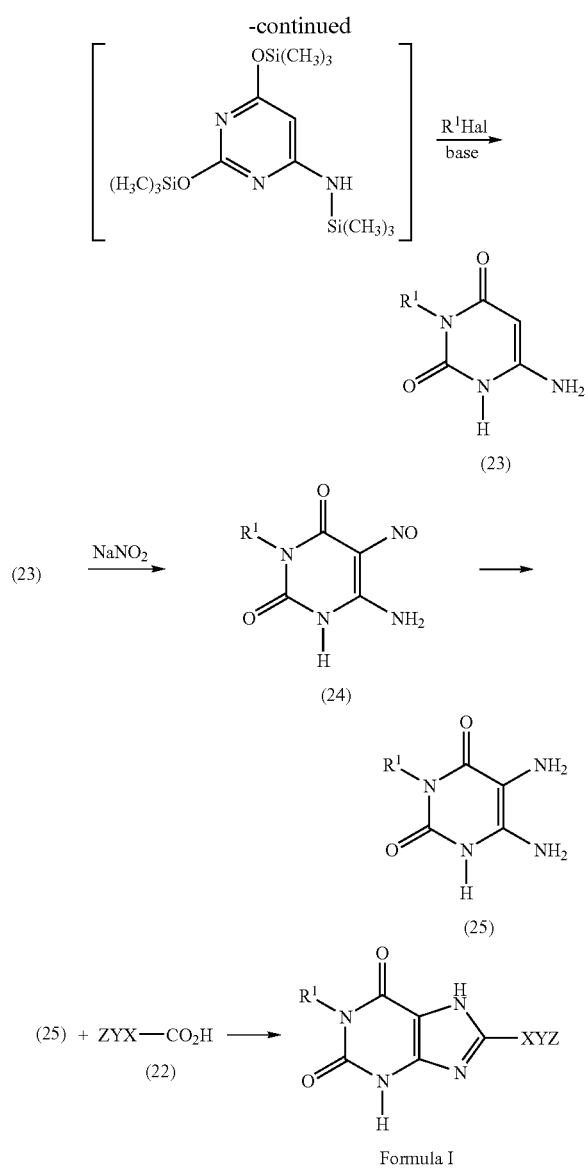

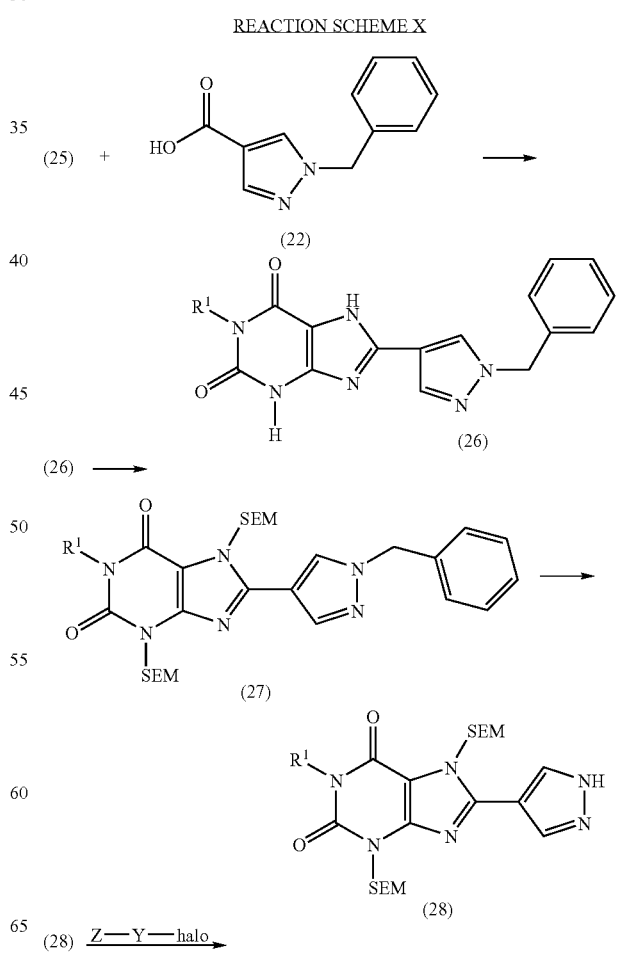

plete, the product of formula (24) is isolated by conventional means, for example by filtration.

Step 3—Preparation of Formula (25)

The compound of formula (24) is then reduced to a diamino derivative. In general, the compound of formula (24) is dissolved in aqueous ammonia, and then a reducing agent, for example sodium hydrosulfite, added. The reaction is conducted at a temperature of about 70° C. When the reaction is substantially complete, the product of formula (25) is isolated conventionally, for example by filtration of the cooled reaction mixture.

Step 4—Preparation of Formula I

The compound of formula (25) is then reacted with a carboxylic acid of the formula Z-Y—X—CO$_2$H in the presence of a carbodiimide, for example 1-(3-dimethylaminopropyl)-3-ethylcarbodiimide hydrochloride. The reaction is conducted at a temperature of about 20-30° C., for about 12-48 hours. The product is isolated conventionally, for example by filtration, and reacted with excess hexamethyldisilazane in the presence of ammonium sulfate, for about 2 days at reflux. When the reaction is substantially complete, the product of Formula I is isolated conventionally, for example by filtration of the cooled reaction mixture.

A specific example of the preparation shown in Reaction Scheme IX, where X is optionally substituted 1,4-pyrazolene, is shown in Reaction Scheme X.

Step 1—Preparation of Formula (23)

The commercially available compound 6-aminouracil is first silylated, for example by reaction with hexamethyldisilazane as a solvent in the presence of a catalyst, for example ammonium sulfate. The reaction is carried out at about reflux temperature, for about 1-10 hours. When the reaction is substantially complete, the silylated compound thus produced is isolated conventionally, and then reacted with a compound of formula R$^1$Hal, where R$^1$ is as defined above other than hydrogen, preferably in the absence of a solvent. The reaction is carried out at about reflux, for about 12 hours to 7 days. When the reaction is substantially complete, the product of formula (23) is isolated by conventional means.

Step 2—Preparation of Formula (24)

The compound of formula (23) is then dissolved in an aqueous acid, for example aqueous acetic acid, and reacted with sodium nitrite. The reaction is carried out at a temperature of about 20-50° C., preferably about 30° C., over about 30 minutes. When the reaction is substantially com-

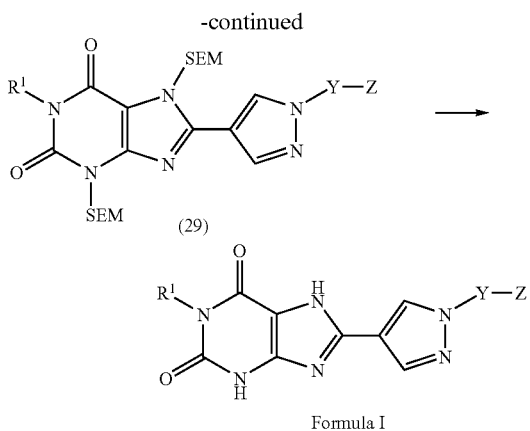

Formula I where SEM is 2,2-(trimethylsilyl)ethoxymethyl and halo is chloro, bromo, or iodo. It should be noted that the compound of formula (26) corresponds to a compound of Formula I in which $R^2$ and $R^3$ are hydrogen, X is 1-pyrazol-4-yl, Y is methylene, and Z is phenyl. This reaction is described in more detail in the following examples.

The same reaction scheme can be used for the preparation of a compound of Formula I in which the 1 and 3 positions are substituted (i.e., $R^1$ and $R^2$ are not hydrogen), by starting with a compound of formula (21) in which $R^3$ is hydrogen and reacting with the compound of formula (22) as above.

An example of a synthesis of a compound of formula (22) is shown in Reaction Scheme XI:

REACTION SCHEME XI

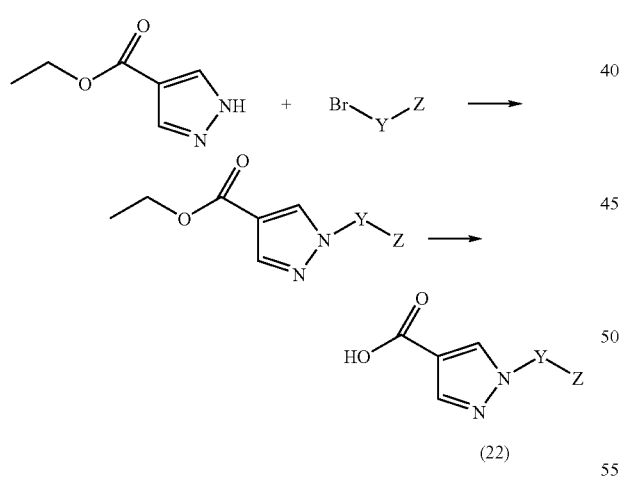

For example, if Z-Y—Br represents 3-phenylpropyl bromide, then the product (22) is 1-(3-phenylpropyl)pyrazole-4-carboxylic acid. If Z-Y—Br represents (1-oxy-pyridin-3yl)methyl bromide, then the product (22) is 1-(1-oxypyridin-3-ylmethyl)pyrazole-4-carboxylic acid. The reaction is carried out as shown in Example 9.

The pyrazole product of formula (22) is then reacted with a compound of formula (21) or (25) as described above, and in Example 9, to provide a compound of Formula H (and Formula I if $R^3$ is hydrogen). For example:

Formula I or II

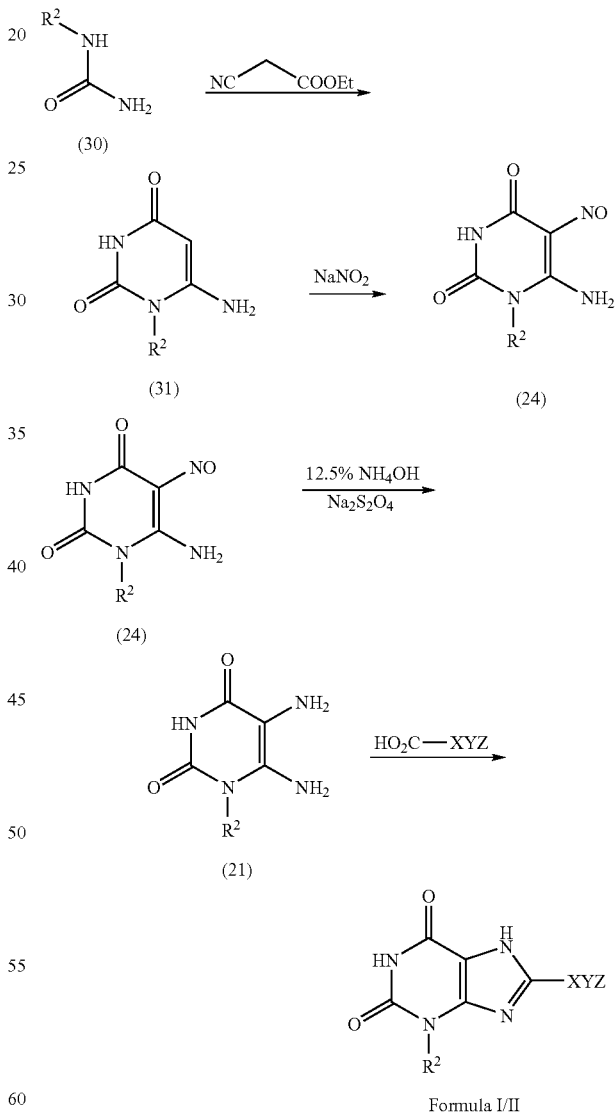

The preparation of a compound of Formula I in which $R^1$ is hydrogen and $R^2$ is other than hydrogen from a compound of formula (24) is shown in Reaction Scheme XII.

REACTION SCHEME XII

Step 1—Preparation of Formula (31)

The compound of formula (30) is either commercially available or prepared by means well known in the art. It is reacted with ethyl cyanoacetate in a protic solvent, for example ethanol, in the presence of a strong base, for example sodium ethoxide. The reaction is carried out at about reflux temperature, for about 4 to about 24 hours. When the reaction is substantially complete, the compound of formula (31) thus produced is isolated conventionally.

Step 2—Preparation of Formula (24)

The compound of formula (31) is then mixed with sodium nitrite in an aqueous solvent, for example dimethylformamide and water, and reacted with a strong acid, for example hydrochloric acid, to produce the nitroso compound of formula (24). The reaction is carried out at a temperature of about 50° C. to about 100° C., for about 1 hour. When the reaction is substantially complete, the product of formula (24) is isolated by conventional means.

Step 3—Preparation of Formula (21)

The compound of formula (24) is then reduced to a diamino derivative. In general, the compound of formula (24) is dissolved in aqueous ammonia, and then a reducing agent, for example sodium hydrosulfite, added. The reaction is conducted at a temperature of about 70° C. When the reaction is substantially complete, the product of formula (21) is isolated conventionally, for example by filtration of the cooled reaction mixture.

Step 4—Preparation of Formula I

The compound of formula (21) is then reacted with a carboxylic acid of the formula Z—Y—X—CO$_2$H in the same manner as described for Reaction Scheme IX, step 4, to produce a compound of Formula I.

The compound of formula (31) can be used in an alternative synthesis to prepare a compound of Formula I in which R$^1$ is hydrogen and R$^2$ is other than hydrogen, or both R$^1$ and R$^2$ are other than hydrogen and are the same or different, as shown in Reaction Scheme XIII.

REACTION SCHEME XIII

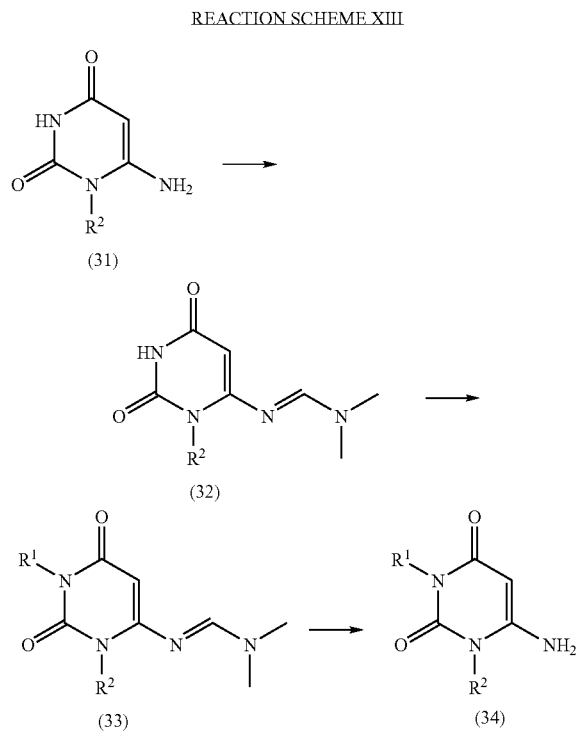

Steps 1 and 2

The compound of formula (31), prepared as shown above, is reacted with the dimethylacetal of N,N-dimethylformamide in a polar solvent, for example N,N-dimethylformamide. The reaction is carried out at about 40° C., for about 1 hour. When the reaction is substantially complete, the compound of formula (32) thus produced is reacted with a compound of formula R$^1$Hal, where Hal is chloro, bromo, or iodo, in the presence of a base, for example potassium carbonate. The reaction is carried out at about 80° C., for about 4-24 hour. When the reaction is substantially complete, the product of formula (33) is isolated conventionally, for example by evaporation of the solvents under reduced pressure, and the residue is used in the next reaction with no further purification.

Step 2

The compound of formula (33) is reacted with aqueous ammonia in a polar solvent, for example suspended in methanol. The reaction is carried out at about room temperature, for about 1-3 days. When the reaction is substantially complete, the product of formula (33) is isolated conventionally, for example by evaporation of the solvents under reduced pressure, and triturating the residue with water.

The compound of formula (34) is then converted to a compound of Formula I in the same manner as shown above for the preparation of the compound of formula (23) in Reaction Scheme IX.

Preferred Processes and Last Steps

The compounds of the present invention can be prepared according to the following last steps:
1. Contacting a compound of the formula:

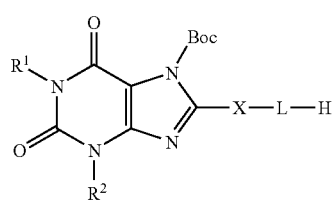

(5)

in which R$^1$, R$^2$, and X are as defined in the Summary of the Invention, L is —O—. —S—, or —NH—, and Boc is is t-butyloxycarbonyl;

with a compound of the formula Z-Y-LG, in which Z and Y are as defined in the Summary of the Invention, and LG is a leaving group.
2. Contacting a compound of the formula:

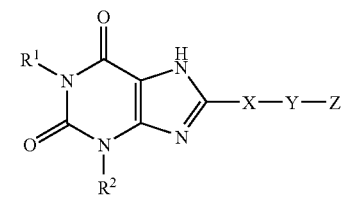

Formula I where R$^3$ is hydrogen in which R$^1$, R$^2$, and X, Y and Z are as defined in the Summary of the Invention:

with a compound of the formula R³-LG, where R³ is as defined in the Summary of the Invention, and LG is a leaving group.

3. Contacting a compound of the formula:

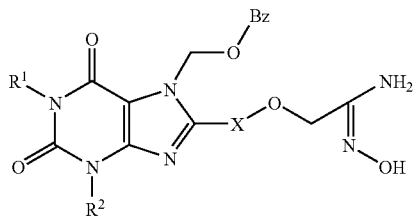

(8)

in which R¹, R², and X are as defined in the Summary of the Invention:

with an acid chloride of the formula RC(O)Cl, in which R represents an optional substitution that leads to 5-substitution on the oxadiazole ring;

to provide a compound of Formula I in which Y is oxygen, and Z is optionally substituted 1,2,4-oxadiazole.

4. Contacting a Compound of the Formula:

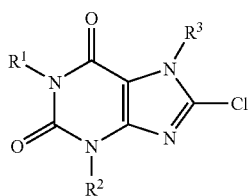

(14)

in which R¹, R², and R³ are as defined in the Summary of the Invention:

with a compound of formula (HO)₂B—X—Y-Z, in which X, Y and Z are as defined in the Summary of the Invention.

5. Contacting a compound of the formula:

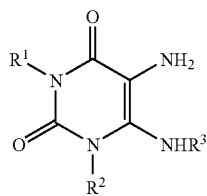

(17)

in which R¹, R², and R³ are as defined in the Summary of the Invention:

with a compound of the formula ZYXCO₂H (a compound of formula (22)), in which X, Y and Z are as defined in the Summary of the Invention.

Utility, Testing and Administration

General Utility

The compounds of Formula I and II are effective in the treatment of conditions that respond to administration of $A_{2B}$ adenosine receptor antagonists. Such conditions include, but are not limited to, at least one of diarrhea, atherosclerosis, restenosis, diabetes, in particular type-II diabetes, macular degeneration, diabetic retinopathy, cancer, senile dementia, Alzheimer's disease, Parkinson's disease, traumatic brain injury, and Type I hypersensitivity reactions, including asthma, atopic eczema, and hay fever.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule).

The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

Preparation of a Compound of Formula (2) where $R^1$ and $R^2$ are both n-Propyl

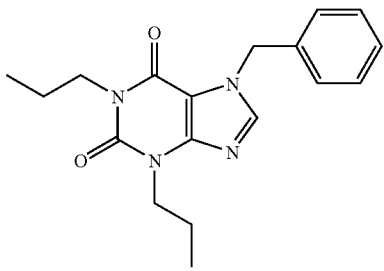

To a solution of 7-benzyl-1,3,7-trihydropurine-2,6-dione (6.4 g, 26.4 mmol), the compound of formula (1), in N,N-dimethylformamide (200 ml) at room temperature was added sodium hydride (2.6 g, 66 mmol). The mixture was stirred for 20 minutes, then iodopropane (6.5 ml, 66 mmol) added, and stirred at room temperature for 3 hours. The mixture was then heated to 70° C. and stirred overnight. The solvent was removed under reduced pressure, dissolved in dichloromethane, and passed through a silica gel plug, washing with 1:1 hexane/ethyl acetate. The solvent was removed under reduced pressure, affording crude 7-benzyl-1,3-dipropyl-1,3,7-trihydropurine-2,6-dione (8.5 g, 98% yield), which was used in the next reaction with no further purification.

B. Preparation of a Compound of Formula (2), Varying $R^1$ and $R^2$

Similarly, following the procedure of 1A above, but replacing iodopropane by other halides, the following compounds of formula (3) are prepared:

7-benzyl-1,3-dimethyl-1,3,7-trihydropurine-2,6-dione;

7-benzyl-1,3-diethyl-1,3,7-trihydropurine-2,6-dione;

7-benzyl-1,3-di(methoxyethyl)-1,3,7-trihydropurine-2,6-dione;

7-benzyl-1,3-di-n-butyl-1,3,7-trihydropurine-2,6-dione;

7-benzyl-1,3-diisobutyl-1,3,7-trihydropurine-2,6-dione;

1,3,7-tribenzyl-1,3,7-trihydropurine-2,6-dione;

7-benzyl-1,3-di(phenylethyl)-1,3,7-trihydropurine-2,6-dione;

7-benzyl-1,3-dicyclobutyl-1,3,7-trihydropurine-2,6-dione;

7-benzyl-1,3-di(pyrid-4-ylmethyl)-1,3,7-trihydropurine-2,6-dione;

7-benzyl-1,3-di(furan-3-ylmethyl)-1,3,7-trihydropurine-2,6-dione;

7-benzyl-1,3-di(4-methoxybenzyl)-1,3,7-trihydropurine-2,6-dione;

7-benzyl-1,3-di(4-trifluoromethylbenzyl)-1,3,7-trihydropurine-2,6-dione; and 7-benzyl-1,3-di(3-fluorobenzyl)-1,3,7-trihydropurine-2,6-dione.

EXAMPLE 2

Preparation of a Compound of Formula (3)

A. Preparation of a Compound of Formula (3) where $R^1$ and $R^2$ are both n-Propyl

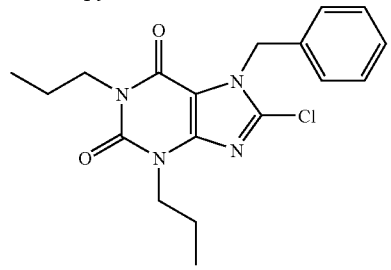

7-Benzyl-1,3-dipropyl-1,3,7-trihydropurine-2,6-dione, a compound of formula (2), (2.0 g, 6.1 mmole) and N-chlorosuccinimide (1.0 g, 7.4 mmole) were combined in 100 mL of tetrahydrofuran and stirred at room temperature for 4 hours. The solvent was removed under reduced pressure, and the residue dissolved in ethyl acetate. The solution was washed with water, then brine, and dried over magnesium sulfate. The solvent was removed under vacuum, to afford a compound of formula (3) where $R^1$ and $R^2$ are both n-propyl, 7-benzyl-8-chloro-1,3-dipropyl-1,3,7-trihydropurine-2,6-dione, which was recrystallized from ethyl acetate/hexane (1:50).

B. Preparation of a Compound of Formula (3), Varying $R^1$ and $R^2$

Similarly, following the procedure of 2A above, but replacing 7-benzyl-1,3-dipropyl-1,3,7-trihydropurine-2,6-dione by other compounds of formula (2), the following compounds of formula (3) are prepared:

7-benzyl-8-chloro-1,3-dimethyl-1,3,7-trihydropurine-2,6-dione;

7-benzyl-8-chloro-1,3-diethyl-1,3,7-trihydropurine-2,6-dione;

7-benzyl-8-chloro-1,3-di(methoxyethyl)-1,3,7-trihydropurine-2,6-dione;

7-benzyl-8-chloro-1,3-di-n-butyl-1,3,7-trihydropurine-2,6-dione;

7-benzyl-8-chloro-1,3-diisobutyl-1,3,7-trihydropurine-2,6-dione;

8-chloro-1,3,7-tribenzyl-1,3,7-trihydropurine-2,6-dione;

7-benzyl-8-chloro-1,3-di(phenylethyl)-1,3,7-trihydropurine-2,6-dione;

7-benzyl-8-chloro-1,3-dicyclobutyl-1,3,7-trihydropurine-2,6-dione;

7-benzyl-8-chloro-1,3-di(pyrid-4-ylmethyl)-1,3,7-trihydropurine-2,6-dione;

7-benzyl-8-chloro-1,3-di(furan-3-ylmethyl)-1,3,7-trihydropurine-2,6-dione;

7-benzyl-8-chloro-1,3-di(4-methoxybenzyl)-1,3,7-trihydropurine-2,6-dione;

7-benzyl-8-chloro-1,3-di(4-trifluoromethylbenzyl)-1,3,7-trihydropurine-2,6-dione; and 7-benzyl-8-chloro-1,3-di(3-fluorobenzyl)-1,3,7-trihydropurine-2,6-dione.

C. Preparation of a Compound of Formula (3), Varying $R^1$ and $R^2$

Similarly, following the procedure of 2A above, but replacing 7-benzyl-1,3-dipropyl-1,3,7-trihydropurine-2,6-dione by other compounds of formula (2), any compound of formula (3) is prepared.

EXAMPLE 3

Preparation of a Compound of Formula (4)

A. Preparation of a Compound of Formula (4) where $R^1$ and $R^2$ are both n-Propyl, X is Phenyl, and L is —O—

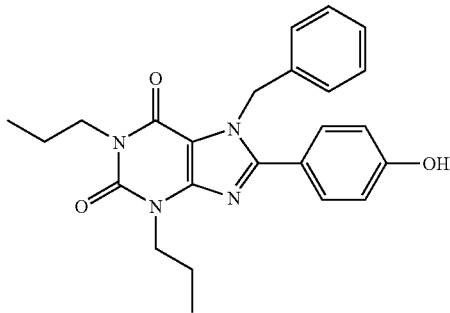

7-Benzyl-8-chloro-1,3-dipropyl-1,3,7-trihydropurine-2,6-dione, a compound of formula (3) where $R^1$ and $R^2$ are both n-propyl (5.0 g, 14 mmoles), and 4-hydroxyphenylboronic acid (2.0 g, 14 mmoles) were dissolved in 100 ml of a mixture of toluene/ethanol (4:1) and stirred at reflux for 16 hours. Solvent was removed under reduced pressure, and the residue was chromatographed over a silica gel column, eluting with ethyl acetate:hexane (1:4) to give a compound of formula (4) where $R^1$ and $R^2$ are both n-propyl, X is phenyl, and L is —O— (7-benzyl-8-(4-hydroxyphenyl)-1,3-dipropyl-1,3,7-trihydropurine-2,6-dione), as a pale yellow solid.

B. Preparation of a Compound of Formula (4), Varying $R^1$, $R^2$, X and L

Similarly, following the procedure of 3A above, replacing 7-benzyl-8-chloro-1,3-dipropyl-1,3,7-trihydropurine-2,6-dione with other compounds of formula (3), the following compounds of formula (4) are prepared:

7-benzyl-8-(4-hydroxyphenyl)-1,3-dimethyl-1,3,7-trihydropurine-2,6-dione;
7-benzyl-8-(4-hydroxyphenyl)-1,3-diethyl-1,3,7-trihydropurine-2,6-dione;
7-benzyl-8-(4-hydroxyphenyl)-1,3-di(methoxyethyl)-1,3,7-trihydropurine-2,6-dione;
7-benzyl-8-(3-methoxy-4-hydroxyphenyl)-1,3-di-n-butyl-1,3,7-trihydropurine-2,6-dione;
7-benzyl-8-(3-hydroxypyrid-2-yl)-1,3-diisobutyl-1,3,7-trihydropurine-2,6-dione;
8-(2-fluoro-3-hydroxyphenyl)-1,3,7-tribenzyl-1,3,7-trihydropurine-2,6-dione;
7-benzyl-8-(2-trifluoromethyl-4-hydroxyphenyl)-1,3-di(phenylethyl)-1,3,7-trihydropurine-2,6-dione;
7-benzyl-8-(5-hydroxybenzothiazol-2-yl)-1,3-dicyclobutyl-1,3,7-trihydropurine-2,6-dione;
7-benzyl-8-(4-hydroxyphenyl)-1,3-di(pyrid-4-ylmethyl)-1,3,7-trihydropurine-2,6-dione;
7-benzyl-8-(4-hydroxyphenyl)-1,3-di(furan-3-ylmethyl)-1,3,7-trihydropurine-2,6-dione;
7-benzyl-8-(4-hydroxyphenyl)-1,3-di(4-methoxybenzyl)-1,3,7-trihydropurine-2,6-dione;
7-benzyl-8-(4-hydroxyphenyl)-1,3-di(4-trifluoromethylbenzyl)-1,3,7-trihydropurine-2,6-dione; and
7-benzyl-8-(4-hydroxyphenyl)-1,3-di(3-fluorobenzyl)-1,3,7-trihydropurine-2,6-dione.

C. Preparation of a Compound of Formula (4), Varying $R^1$, $R^2$, X and L

Similarly, following the procedure of 3A above, but replacing 7-benzyl-8-chloro-1,3-dipropyl-1,3,7-trihydropurine-2,6-dione with other compounds of formula (3), any compound of formula (4) is prepared.

EXAMPLE 4

Preparation of a Compound of Formula (5)

A. Preparation of a Compound of Formula (5) where $R^1$ and $R^2$ are both n-Propyl, X is Phenyl, and L is —O—

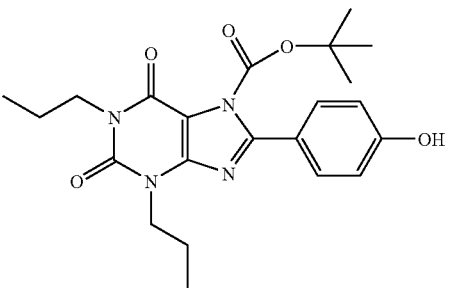

The compound of formula (4) where $R^1$ and $R^2$ are both n-propyl, X is phenyl, and L is —O— (7-benzyl-8-(4-hydroxyphenyl)-1,3-dipropyl-1,3,7-trihydropurine-2,6-dione) (613 mg) was dissolved in methanol (50 ml), a catalytic amount of palladium hydroxide added, and the mixture stirred under hydrogen at room temperature overnight. The mixture was filtered, washing the catalyst with methanol, and the solvent was evaporated from the filtrate under reduced pressure to provide. 8-(4-hydroxyphenyl)-1,3-dipropyl-1,3,7-trihydropurine.

This product was dissolved in methanol, di-tert-butyldicarbonate (0.7 g, 3.2 mmol) and N,N-di-isopropylethylamine (1 ml) added, and the mixture refluxed overnight. The solvent was removed under reduced pressure, and the residue chromatographed on a silica gel column, to give a compound of formula (5), 7-t-butoxycarbonyl-8-(4-hydroxyphenyl)-1,3-dipropyl-1,3,7-trihydropurine-2,6-dione.

B. Preparation of a Compound of Formula (5), Varying $R^1$, $R^2$, X and L

Similarly, following the procedure of 4A above, replacing 7-benzyl-8-(4-hydroxyphenyl)-1,3-dipropyl-1,3,7-trihydropurine-2,6-dione with other compounds of formula (4), the following compounds of formula (5) are prepared:

7-t-butoxycarbonyl-8-(4-hydroxyphenyl)-1,3-dimethyl-1,3,7-trihydropurine-2,6-dione;
7-t-butoxycarbonyl-8-(4-hydroxyphenyl)-1,3-diethyl-1,3,7-trihydropurine-2,6-dione;
7-t-butoxycarbonyl-8-(4-hydroxyphenyl)-1,3-di(methoxyethyl)-1,3,7-trihydropurine-2,6-dione;
7-t-butoxycarbonyl-8-(3-methoxy-4-hydroxyphenyl)-1,3-di-n-butyl-1,3,7-trihydropurine-2,6-dione;
7-t-butoxycarbonyl-8-(3-hydroxypyrid-2-yl)-1,3-diisobutyl-1,3,7-trihydropurine-2,6-dione;
7-t-butoxycarbonyl-8-(2-fluoro-3-hydroxyphenyl)-1,3-dibenzyl-1,3,7-trihydropurine-2,6-dione;
7-t-butoxycarbonyl-8-(2-trifluoromethyl-4-hydroxyphenyl)-1,3-di(phenylethyl)-1,3,7-trihydropurine-2,6-dione;

7-t-butoxycarbonyl-8-(5-hydroxybenzothiazol-2-yl)-1,3-dicyclobutyl-1,3,7-trihydropurine-2,6-dione;

7-t-butoxycarbonyl-8-(4-hydroxyphenyl)-1,3-di(pyrid-4-ylmethyl)-1,3,7-trihydropurine-2,6-dione;

7-t-butoxycarbonyl-8-(4-hydroxyphenyl)-1,3-di(furan-3-ylmethyl)-1,3,7-trihydropurine-2,6-dione;

7-t-butoxycarbonyl-8-(4-hydroxyphenyl)-1,3-di(4-methoxybenzyl)-1,3,7-trihydropurine-2,6-dione;

7-t-butoxycarbonyl-8-(4-hydroxyphenyl)-1,3-di(4-trifluoromethylbenzyl)-1,3,7-trihydropurine-2,6-dione; and 7-t-butoxycarbonyl-8-(4-hydroxyphenyl)-1,3-di(3-fluorobenzyl)-1,3,7-trihydropurine-2,6-dione.

C. Preparation of a Compound of Formula (5), Varying $R^1$, $R^3$, and X

Similarly, following the procedure of 4A above, but replacing 7-benzyl-8-(4-hydroxyphenyl)-1,3-dipropyl-1,3,7-trihydropurine-2,6-dione with other compounds of formula (3), any compound of formula (5) is prepared.

EXAMPLE 5

Preparation of a Compound of Formula I

A. Preparation of a Compound of Formula I where $R^1$ and $R^2$ are n-Propyl, X is Phenyl, Y is —O—CH$_2$—, and Z is 5-(4-methoxyphenyl)-[1,2,4]oxadiazol-3-yl

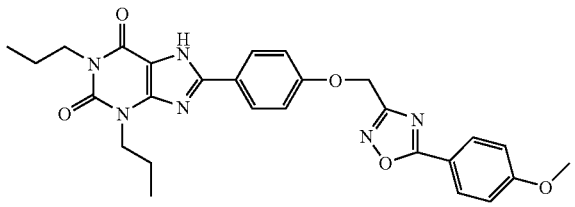

A mixture of 7-t-butoxycarbonyl-8-(4-hydroxyphenyl)-1,3-dipropyl-1,3,7-trihydropurine-2,6-dione, a compound of formula (5) (50 mg, 0.117 mmol), 3-chloromethyl-5-(4-methoxyphenyl)-[1,2,4]oxadiazole (26 mg, 0.117 mmol), and sodium hydride (10 mg, 0.234 mmol) in N,N-dimethylformamide was stirred at room temperature for 24 hours. The solvent was removed under reduced pressure, and the residue purified by preparative thin layer chromatography, to afford 8-{4-[5-(4-methoxyphenyl)-[1,2,4]oxadiazol-3-ylmethoxy]phenyl}-1,3-dipropyl-1,3,7-trihydropurine-2,6-dione.

B. Preparation of a Compound of Formula I where $R^1$ and $R^2$ are n-Propyl, Varying X, Y, and Z Similarly, following the procedure of 5A above, but optionally replacing 7-t-butoxycarbonyl-8-(4-hydroxyphenyl)-1,3-dipropyl-1,3,7-trihydropurine-2,6-dione by other compounds of formula (5), and optionally replacing 3-chloromethyl-5-(4-methoxyphenyl)-[1,2,4]oxadiazole by other compounds of formula Cl—Y-Z, the following compounds of Formula I were prepared:

8-{4-[5-(2-methoxyphenyl)-[1,2,4]oxadiazol-3-ylmethoxy]phenyl}-1,3-dipropyl-1,3,7-trihydropurine-2,6-dione;

8-{4-[5-(3-methoxyphenyl)-[1,2,4]oxadiazol-3-ylmethoxy]phenyl}-1,3-dipropyl-1,3,7-trihydropurine-2,6-dione;

8-{4-[5-(4-fluorophenyl)-[1,2,4]oxadiazol-3-ylmethoxy]phenyl}-1,3-dipropyl-1,3,7-trihydropurine-2,6-dione;

8-{4-[5-(4-(trifluoromethyl)phenyl)-[1,2,4]oxadiazol-3-ylmethoxy]phenyl}-1,3-dipropyl-1,3,7-trihydropurine-2,6-dione; and 8-{4-[5-(4-trifluoromethylphenyl)-[1,2,4]oxadiazol-3-ylmethoxy]phenyl}-1,3-dipropyl-1,3,7-trihydropurine-2,6-dione.

C. Preparation of a Compound of Formula I, Varying $R^1$, $R^2$, X, Y and Z

Similarly, following the procedure of 5A above, but optionally replacing 7-t-butoxycarbonyl-8-(4-hydroxyphenyl)-1,3-dipropyl-1,3,7-trihydropurine-2,6-dione by other compounds of formula (5), and optionally replacing 3-chloromethyl-5-(4-methoxyphenyl)-[1,2,4]oxadiazole by other compounds of formula YZ, the following compounds of Formula I are prepared:

8-{4-[5-(4-methoxyphenyl)-[1,2,4]oxadiazol-3-ylmethoxy]phenyl}-1,3-dimethyl-1,3,7-trihydropurine-2,6-dione;

8-{4-[5-(4-methoxyphenyl)-[1,2,4]oxadiazol-3-ylmethoxy]phenyl}-1,3-diethyl-1,3,7-trihydropurine-2,6-dione;

8-{4-[5-(4-methoxyphenyl)-[1,2,4]oxadiazol-3-ylmethoxy]phenyl}-1,3-di(methoxyethyl)-1,3,7-trihydropurine-2,6-dione;

8-{4-[5-(4-methoxyphenyl)-[1,2,4]oxadiazol-3-ylmethoxy]phenyl}-1,3-di-n-butyl-1,3,7-trihydropurine-2,6-dione;

8-{4-[5-(4-methoxyphenyl)-[1,2,4]oxadiazol-3-ylmethoxy]phenyl}-1,3-diisobutyl-1,3,7-trihydropurine-2,6-dione;

8-{4-[5-(2-fluoro-3-hydroxyphenyl)-[1,2,4]oxadiazol-3-ylmethoxy]phenyl}-1,3-dibenzyl-1,3,7-trihydropurine-2,6-dione;

8-{4-[5-(2-trifluoromethyl-4-hydroxyphenyl)-[1,2,4]oxadiazol-3-ylmethoxy]phenyl}-1,3-di-(phenylethyl)-1,3,7-trihydropurine-2,6-dione;

8-{4-[5-(4-trifluoromethyl-3-hydroxyphenyl)-[1,2,4]oxadiazol-3-ylmethoxy]phenyl}-1,3-dicyclobutyl-1,3,7-trihydropurine-2,6-dione;

8-{4-[5-(4-hydroxyphenyl)-[1,2,4]oxadiazol-3-ylmethoxy]phenyl}-1,3-di(pyrid-4-ylmethyl)-1,3,7-trihydropurine-2,6-dione;

8-{4-[5-(4-hydroxyphenyl)-[1,2,4]oxadiazol-3-ylmethoxy]phenyl}-1,3-di(furan-3-ylethyl)-1,3,7-trihydropurine-2,6-dione;

8-{4-[5-(4-methoxyphenyl)imidazol-2-ylmethoxy]phenyl}-1,3-dipropyl-1,3,7-trihydropurine-2,6-dione;

8-{4-[5-(4-methoxyphenyl)oxazol-2-ylmethoxy]phenyl}-1,3-dipropyl-1,3,7-trihydropurine-2,6-dione;

8-{4-[5-(4-methoxyphenyl)thiazol-2-ylmethoxy]phenyl}-1,3-dipropyl-1,3,7-trihydropurine-2,6-dione;

8-{4-[5-(4-methoxyphenyl)-1,3,5-triazin-2-ylmethoxy]phenyl}-1,3-dipropyl-1,3,7-trihydropurine-2,6-dione;

8-{4-[5-(4-methoxyphenyl)pyrimidin-2-ylmethoxy]phenyl}-1,3-dipropyl-1,3,7-trihydropurine-2,6-dione;

8-{4-[5-(4-methoxyphenyl)-[1,2,4]oxadiazol-3-ylethoxy]phenyl}-1,3-dipropyl-1,3,7-trihydropurine-2,6-dione;

8-{4-[5-(4-methoxyphenyl)-[1,2,4]oxadiazol-3-ylpropoxy]phenyl}-1,3-dipropyl-1,3,7-trihydropurine-2,6-dione;

8-{4-[5-(4-fluorophenyl)-[1,2,4]oxadiazol-3-ylmethoxy]phenyl}-1,3-dipropyl-1,3,7-trihydropurine-2,6-dione;

8-{4-[5-(4-trifluoromethylphenyl)-[1,2,4]oxadiazol-3-ylmethoxy]phenyl}-1,3-dipropyl-1,3,7-trihydropurine-2,6-dione;

8-{4-[5-(3,4-dimethoxyphenyl)-[1,2,4]oxadiazol-3-ylmethoxy]phenyl}-1,3-dipropyl-1,3,7-trihydropurine-2,6-dione; and 8-{5-[5-(4-methoxyphenyl)-[1,2,4]oxadiazol-3-ylethoxy]pyridin-2-yl}-1,3-dipropyl-1,3,7-trihydropurine-2,6-dione.

D. Preparation of a Compound of Formula I, Varying $R^1$, $R^2$, X, Y, and Z

Similarly, following the procedure of 5A above, but optionally replacing 7-t-butoxycarbonyl-8-(4-hydroxyphenyl)-1,3-dipropyl-1,3,7-trihydropurine-2,6-dione by other compounds of formula (5), and optionally replacing 3-chloromethyl-5-(4-methoxyphenyl)-[1,2,4]oxadiazole by other compounds of formula YZ, any compound of Formula I can be prepared.

EXAMPLE 6

Preparation of a Compound of Formula (7)

A. Preparation of a Compound of Formula (7) where $R^1$ and $R^2$ are n-Propyl and X is 1,4-Phenylene

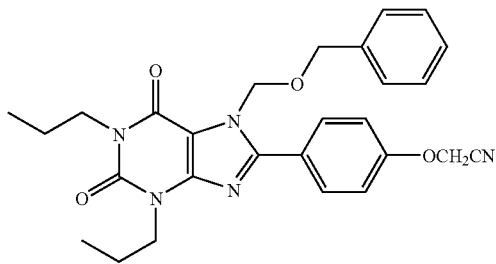

a) A solution of 7-benzyl-8-(4-benzyloxyphenyl)-1,3-dipropyl-1,3,7-trihydropurine-2,6-dione (4.39 g, 8.117 mmol) (prepared in a manner analogous to the preparation of the compound of formula (5)) in methylene chloride-methanol (1:1) (100 ml) was stirred under hydrogen with a catalytic amount of 10% Pd(OH)$_2$/C at room temperature overnight. The catalyst was filtered off, washed with dichloromethane/methanol, and the filtrate was evaporated under reduced pressure to give a solid, which was washed with methylene chloride to afford pure product, 8-(4-hydroxyphenyl)-1,3-dipropyl-1,3,7-trihydropurine-2,6-dione.

b) A mixture of 8-(4-hydroxyphenyl)-1,3-dipropyl-1,3,7-trihydropurine-2,6-dione (2.2 g, 6.7 mmol), tert-butyldimethylsilyl chloride (2.0 g, 13.4 mmol), and imidazole (0.91 g, 13.4 mmol) in tetrahydrofuran (50 ml) was stirred overnight at room temperature, then refluxed for 10 hours. The solvent was removed under reduced pressure, and the residue was dissolved in methylene chloride and passed through a silica gel plug, which was then washed with ethyl acetate. The filtrate was concentrated under reduced pressure to afford 8-[(4-tert-butyldimethylsilyloxy)phenyl]-1,3-dipropyl-1,3,7-trihydropurine-2,6-dione.

c) To a solution of 8-[(4-tert-butyldimethylsilyloxy)phenyl]-1,3-dipropyl-1,3,7-trihydropurine-2,6-dione (13.7 g, 31 mmol) in tetrahydrofuran (200 ml) was added sodium hydride (1.6 g, 40 mmol), and the mixture was stirred for 30 minutes at room temperature. Benzyloxymethyl chloride (4.9 g, 31 mmol) was then added, and the mixture stirred for 1 hour at room temperature. The solvent was then removed under reduced pressure, and the residue dissolved in methylene chloride. This solution was washed with brine, and the solvent removed under reduced pressure. The residue was chromatographed on silica gel, eluting with ethyl acetate, to afford 7-benzyloxymethyl-8-[(4-tert-butyldimethylsilyloxy)-phenyl]-1,3-dipropyl-1,3,7-trihydropurine-2,6-dione as a liquid.

d) To a solution of 7-benzyloxymethyl-8-[(4-tert-butyldimethylsilyloxy)-phenyl]-1,3-dipropyl-1,3,7-trihydropurine-2,6-dione (10.5 g, 18.7 mmol) in tetrahydrofuran (200 ml) was added tetra(tert-butyl)ammonium fluoride (3 g), and the mixture stirred for 2 hours at room temperature. The product was passed through a silica gel plug, which was washed with ethyl acetate. The filtrate was evaporated under reduced pressure, and the residue washed with dichloromethane, to afford 7-benzyloxymethyl-8-(4-hydroxy-phenyl)-1,3-dipropyl-1,3,7-trihydropurine-2,6-dione as a white solid.

e) To a solution of 7-benzyloxymethyl-8-(4-hydroxyphenyl)-1,3-dipropyl-1,3,7-trihydropurine-2,6-dione (1 g, 2.2 mmol) in tetrahydrofuran (20 ml) was added potassium t-butoxide (0.28 g, 2.4 mmol), and the mixture stirred for 30 minutes at room temperature. Iodoacetonitrile (0.38 g, 2.23 mmol) was then added, and the mixture stirred for 16 hours at room temperature. The solvent was removed under reduced pressure, and the residue was dissolved in ethyl acetate and passed through a silica gel plug, to provide 7-benzyloxymethyl-8-(4-cyanomethoxyphenyl)-1,3-dipropyl-1,3,7-trihydropurine-2,6-dione, a compound of formula (7)

B. Preparation of a Compound of Formula (7), Varying $R^1$ and $R^2$

Similarly, following the procedure of 6A above, but replacing 7-benzyl-8-(4-benzyloxyphenyl)-1,3-dipropyl-1,3,7-trihydropurine-2,6-dione with other similar compounds, other compounds of formula (7) are prepared.

EXAMPLE 7

Preparation of a Compound of Formula (8)

A. Preparation of a Compound of Formula (8) where $R^1$ and $R^2$ are n-Propyl and X is 1,4-Phenylene

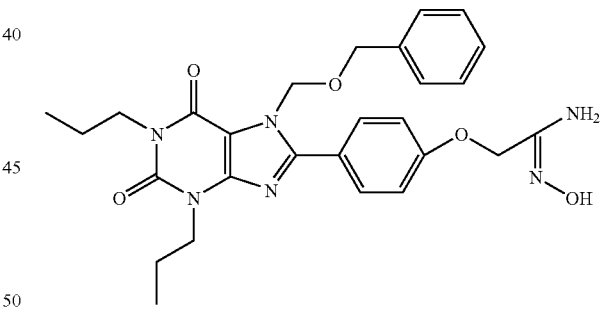

A solution of 7-benzyloxymethyl-8-(4-cyanomethoxyphenyl)-1,3-dipropyl-1,3,7-trihydropurine-2,6-dione (1.15 g, 2.36 mmol) in ethanol (50 ml) was stirred with sodium ethoxide (0.25 g, 3.54 mmol) and hydroxylamine hydrochloride (0.15 g, 3.54 mmol) at room temperature overnight. The solvent was removed under reduced pressure, the residue dissolved in dichloromethane/methanol (50:1), and the solution passed through a silica gel plug. The filtrate was evaporated under reduced pressure to afford 8-[4-(2-amino-2-(hydroxyimino)ethoxy)phenyl]-7-[(phenylmethoxy)methyl]-1,3-dipropyl-1,3,7-trihydropurine-2,6-dione.

B. Preparation of a Compound of Formula (8), Varying $R^1$ and $R^2$

Similarly, following the procedure of 7A above, but replacing 7-benzyloxymethyl-8-(4-cyanomethoxyphenyl)-

1,3-dipropyl-1,3,7-trihydropurine-2,6-dione with other similar compounds, other compounds of formula (8) are prepared.

EXAMPLE 8

Preparation of a Compound of Formula I

A. Preparation of a Compound of Formula I where $R^1$ and $R^2$ are n-Propyl, $R^3$ is Hydrogen, X is 1,4-Phenylene, Y is —O(CH$_2$)—, and Z is 5-(2-chlorophenyl)-[1,2,4]oxadiazol-3-yl

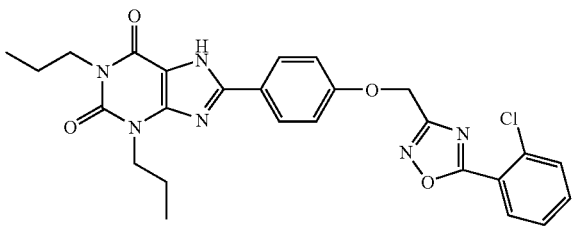

To a solution of 7-benzyloxymethyl-8-[4-(amino(hydroxyimino)methoxy)-phenyl]-1,3-dipropyl-1,3,7-trihydropurine-2,6-dione (50 mg) in dioxane (3 ml) was added potassium carbonate (0.5 g), followed by 2-chlorobenzoyl chloride. The mixture was stirred at room temperature for 10 minutes, then the solids filtered off. The filtrate was evaporated under reduced pressure, and the residue dissolved in xylene. The solution was heated to 145° C. overnight, then the solvent removed under reduced pressure, and the residue chromatographed on silica gel, eluting with ethyl acetate, to afford 8-{4-[5-(2-chlorophenyl)-[1,2,4]oxadiazol-3-yl-methoxy]phenyl}-1,3-dipropyl-1,3-dihydropurine-2,6-dione.

B. Preparation of a Compound of Formula I where $R^1$ and $R^2$ are n-Propyl, Varying X, Y, and Z Similarly, following the procedure of 8A above, but optionally replacing 7-benzyloxymethyl-8-[4-(amino(hydroxyimino)methoxy)-phenyl]-1,3-dipropyl-1,3,7-trihydropurine-2,6-dione by other compounds of formula (8), and optionally replacing RC(O)Cl by other compounds of formula RC(O)Cl, the following compounds of Formula I were prepared:

8-(4-{[5-(3-methylphenyl)(1,2,4-oxadiazol-3-yl)]methoxy}phenyl)-1,3-dipropyl-1,3,7-trihydropurine-2,6-dione;

8-(4-{[5-(2-fluorophenyl)(1,2,4-oxadiazol-3-yl)]methoxy}phenyl)-1,3-dipropyl-1,3,7-trihydropurine-2,6-dione;

8-(4-{[5-(2-methylphenyl)(1,2,4-oxadiazol-3-yl)]methoxy}phenyl)-1,3-dipropyl-1,3,7-trihydropurine-2,6-dione;

8-(4-{[5-(3-methoxyphenyl)(1,2,4-oxadiazol-3-yl)]methoxy}phenyl)-1,3-dipropyl-1,3,7-trihydropurine-2,6-dione;

methyl 4-(3-{[4-(2,6-dioxo-1,3-dipropyl-1,3,7-trihydropurin-8-yl)phenoxy]methyl}-1,2,4-oxadiazol-5-yl)benzoate;

1,3-dipropyl-8-[4-({5-[2-(trifluoromethoxy)phenyl](1,2,4-oxadiazol-3-yl)}methoxy)phenyl]-1,3,7-trihydropurine-2,6-dione;

8-(4-{[5-(2-bromophenyl)(1,2,4-oxadiazol-3-yl)]methoxy}phenyl)-1,3-dipropyl 1,3,7-trihydropurine-2,6-dione; and 8-(4-{[5-(2,4-dimethoxyphenyl)(1,2,4-oxadiazol-3-yl)]methoxy}phenyl)-1,3-dipropyl-1,3,7-trihydropurine-2,6-dione.

C. Similarly, following the procedure of 8A above, but optionally replacing 7-benzyloxymethyl-8-[4-(amino(hydroxyimino)methoxy)-phenyl]-1,3-dipropyl-1,3,7-trihydropurine-2,6-dione by other compounds of formula (8), and optionally replacing RC(O)Cl by other compounds of formula RC(O)Cl, other compounds of Formula I were prepared, for example:

8-[1-(1-oxy-pyridin-3-ylmethyl)-1H-pyrazol-4-yl]-1,3-dipropyl-3,7-dihydro-purine-2,6-dione.

1,3-dipropyl-8-[1-(1-oxypyrid-4-ylmethyl)pyrazol-4-yl]-1,3,7-trihydropurine-2,6-dione; and 1,3-dipropyl-8-[1-(1-oxypyrid-3-ylmethyl)pyrazol-4-yl]-1,3,7-trihydropurine-2,6-dione.

EXAMPLE 9A

Preparation of a Compound of Formula I in which $R^1$ and $R^2$ are the Same

A. Preparation of a Compound of Formula I where $R^1$ and $R^2$ are n-Propyl, X is 1,4-Pyrazolene, $R^3$ is Hydrogen, Y is Propylene, and Z is Phenyl

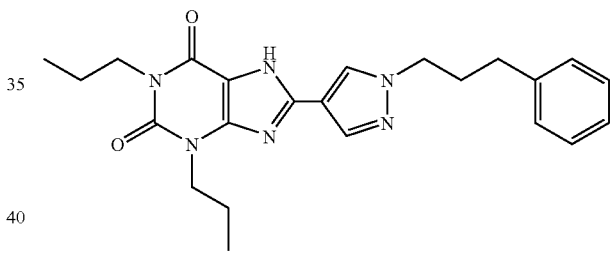

a) To a solution of ethyl 4-pyrazole carboxylate (3.57 mmol) in acetone (30 ml) was added potassium carbonate (35.7 mmol) and 1-bromo-3-phenylpropane (3.57 mmol). The suspension was refluxed overnight, after which the solvent was removed under reduced pressure. The residue was partitioned between ethyl acetate and water, the organic layer dried over magnesium sulfate, filtered, and the filtrate evaporated under reduced pressure to give an oil, which was purified by preparative TLC, to give ethyl 1-(3-phenylpropyl)pyrazole-4-carboxylate.

b) The ester was then dissolved in methanol (30 ml), and potassium hydroxide (1.5 g) added. The mixture was refluxed for 5 hours under nitrogen, then the solvent removed under reduced pressure. The residue was partitioned between methylene chloride and water. The aqueous layer was separated and acidified to pH 1-2 with 6N hydrochloric acid, then extracted with ethyl acetate. The combined organic layers were dried over magnesium sulfate, and the solvent removed under reduced pressure, to give 1-(3-phenylpropyl)pyrazole-4-carboxylic acid.

c To a solution of 1-(3-phenylpropyl)pyrazole-4-carboxylic acid (300 mg, 1.30 mmol) in N,N-dimethylformamide (7 ml) was added 1-[3-(dimethylamino)propyl]-3-ethylcarbodiimide hydrochloride (300 mg). The suspension was stirred at room temperature until all solid was dissolved, then 5,6-diamino-1,3-dipropyl-1,3-dihydropyrimidine-2,4-dione (450 mg) added, and the reaction mixture stirred at room temperature overnight. 2N sodium hydroxide (10 ml) was then added, and the suspension heated at 120° C. for 2 hours. The reaction mixture was cooled in ice water and acidified to pH 2-3. The mixture was partitioned between water and ethyl acetate, and the ethyl acetate layer and any solid material was washed with water, and the solvent removed under reduced pressure. The residue was triturated with ether, giving pure product, 8-[1-(3-phenylpropyl)pyrazol-4-yl)]-1,3-dipropyl-1,3,7-trihydropurine-2,6-dione.

EXAMPLE 9B

Alternative Preparation of a Compound of Formula I in which $R^1$ and $R^2$ are the Same A. Preparation of a Compound of Formula I where $R^1$ and $R^2$ are n-Propyl, X is 1,4-Pyrazolene, $R^3$ is Hydrogen, Y is Methylene, and Z is Phenyl

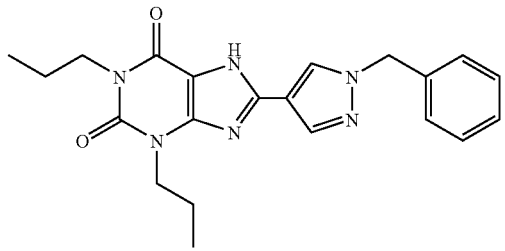

a) To a solution of 1-benzylpyrazole-4-carboxylic acid (4 g, 19.8 mmol) in N,N-dimethylformamide (80 ml) was added 1-[3-(dimethylamino)propyl]-3-ethylcarbodiimide hydrochloride (4 g). The suspension was stirred for 15 minutes at room temperature, then 5,6-diamino-1,3-dipropyl-1,3-dihydropyrimidine-2,4-dione (5.37 mg) added, and the reaction mixture stirred at room temperature overnight. The dimethylformamide was removed under reduced pressure, and 2N sodium hydroxide (60 ml) was then added, and the suspension heated at 120° C. for 2 hours. The reaction mixture was cooled in ice water and acidified to pH 1-2. The mixture was partitioned between water and ethyl acetate, the ethyl acetate layer and accompanying solid was washed several times with water, and the solvent removed under reduced pressure. The residue was triturated with ether, giving 8-[1-benzylpyrazol-4-yl]-1,3-dipropyl-1,3,7-trihydropurine-2,6-dione.

b) 8-[1-benzylpyrazol-4-yl]-1,3-dipropyl-1,3,7-trihydropurine-2,6-dione (3.88 g) was dissolved in dimethylformamide (30 ml), and potassium carbonate (0.642 g) was added, followed by 2-(trimethylsilyl)ethoxymethyl chloride (SEM chloride, 0.768 g). The suspension was stirred at room temperature overnight, at which time a further 0.4 equivalents of potassium carbonate and SEM chloride were added, and the mixture stirred for a further 3 hours. The solid was filtered off, and solvent removed from the filtrate under reduced pressure. The residue was chromatographed on a silica gel column, eluting with 20% ethyl acetate/hexanes, to yield 7-[(3,3-dimethyl-3-silabutoxy)methyl]-8-[1-benzylpyrazol-4-yl]-1,3-dipropyl-1,3,7-trihydropurine-2,6-dione.

c) To a solution of 7-[(3,3-dimethyl-3-silabutoxy)methyl]-8-[1-benzylpyrazol-4-yl]-1,3-dipropyl-1,3,7-trihydropurine-2,6-dione (3 g) in ethanol (100 ml) was added cyclohexene (50 ml) and palladium hydroxide (3 g). The mixture was refluxed for 4 days, then the catalyst was filtered off, and solvent removed from the filtrate under reduced pressure. The residue was chromatographed on a silica gel column, eluting with 30% ethyl acetate/hexanes, to yield 7-[(3,3-dimethyl-3-silabutoxy)methyl]-1,3-dipropyl-8-pyrazol-4-yl-1,3,7-trihydropurine-2,6-dione.

d) To a solution of 7-[(3,3-dimethyl-3-silabutoxy)methyl]-1,3-dipropyl-8-pyrazol-4-yl-1,3,7-trihydropurine-2,6-dione (50 mg) in dimethylformamide (2 ml) was added bromoethylbenzene (0.16 ml) and potassium carbonate (159 mg). The mixture was stirred at room temperature overnight, and the solid material filtered off. Solvent was removed from the filtrate under reduced pressure, and the residue was chromatographed by preparative thin layer chromatography, eluting with 30% ethyl acetate/hexanes, to yield 7-[(3,3-dimethyl-3-silabutoxy)methyl]-8-[1-(2-phenylethyl)pyrazol-4-yl]-1,3-dipropyl-1,3,7-trihydropurine-2,6-dione.

e) A solution of 7-[(3,3-dimethyl-3-silabutoxy)methyl]-8-[1-(2-phenylethyl)pyrazol-4-yl]-1,3-dipropyl-1,3,7-trihydropurine-2,6-dione (53 mg) in ethanol/hydrochloric acid (1M, 2 ml) was refluxed for 2 hours. Solvent was removed from the product under reduced pressure, and the residue was washed with ether, to provide 8-[1-(2-phenylethyl)pyrazol-4-yl]-1,3-dipropyl-1,3,7-trihydropurine-2,6-dione.

B. Preparation of a Compound of Formula I where $R^1$ and $R^2$ are the same, Varying X, Y, and Z Similarly, following the procedure of Example 9A and/or 9B above, the following compounds of Formula I were prepared:

8-(1-benzylpyrazol-4-yl)-1,3-dipropyl-1,3,7-trihydropurine-2,6-dione;

8-{1-[(3,5-dimethylisoxazol-4-yl)methyl]pyrazol-4-yl}-1,3-dipropyl-1,3,7-trihydropurine-2,6-dione;

8-[1-(3-cyclohexylpropyl)pyrazol-4-yl]-1,3-dipropyl-1,3,7-trihydropurine-2,6-dione;

8-(1-{[5-(2-methoxyphenyl)(1,2,4-oxadiazol-3-yl)]methyl}pyrazol-4-yl)-1,3-dipropyl-1,3,7-trihydropurine-2,6-dione;

8-[1-(2-phenoxyethyl)pyrazol-4-yl]-1,3-dipropyl-1,3,7-trihydropurine-2,6-dione;

8-(1-{[5-(4-chlorophenyl)(1,2,4-oxadiazol-3-yl)]methyl}pyrazol-4-yl)-1,3-dipropyl-1,3,7-trihydropurine-2,6-dione;

N-(2,6-dimethylphenyl)-2-[4-(2,6-dioxo-1,3-dipropyl(1,3,7-trihydropurin-8-yl))pyrazolyl]acetamide;

8-(1-{[3-(4-methylphenyl)(1,2,4-oxadiazol-5-yl)]methyl}pyrazol-4-yl)-1,3-dipropyl-1,3,7-trihydropurine-2,6-dione;

8-{1-[2-(1,3-dioxobenzo[c]azolin-2-yl)ethyl]pyrazol-4-yl}-1,3-dipropyl-1,3,7-trihydropurine-2,6-dione;

2-[4-(2,6-dioxo-1,3-dipropyl(1,3,7-trihydropurin-8-yl))pyrazolyl]-N-(2-chlorophenyl)acetamide;

2-[4-(2,6-dioxo-1,3-dipropyl(1,3,7-trihydropurin-8-yl))pyrazolyl]-N-phenylacetamide;

8-{1-[(2-methylphenyl)methyl]pyrazol-4-yl}-1,3-dipropyl-1,3,7-trihydropurine-2,6-dione;

8-{1-[(3-methylphenyl)methyl]pyrazol-4-yl}-1,3-dipropyl-1,3,7-trihydropurine-2,6-dione;

1,3-dipropyl-8-(1-{[2-(trifluoromethyl)phenyl]methyl}pyrazol-4-yl)-1,3,7-trihydropurine-2,6-dione;

8-{1-[(4-methylphenyl)methyl]pyrazol-4-yl}-1,3-dipropyl-1,3,7-trihydropurine-2,6-dione;
8-{1-[(2-fluorophenyl)methyl]pyrazol-4-yl)-1,3-dipropyl-1,3,7-trihydropurine-2,6-dione;
8-{1-[(3-methoxyphenyl)methyl]pyrazol-4-yl}-1,3-dipropyl-1,3,7-trihydropurine-2,6-dione;
8-{1-[(3-chlorophenyl)methyl]pyrazol-4-yl}-1,3-dipropyl-1,3,7-trihydropurine-2,6-dione;
8-{1-[(2-chlorophenyl)methyl]pyrazol-4-yl}-1,3-dipropyl-1,3,7-trihydropurine-2,6-dione;
1,3-dipropyl-8-(1-{[4-(trifluoromethyl)phenyl]methyl}pyrazol-4-yl)-1,3,7-trihydropurine-2,6-dione;
8-{1-[(4-chlorophenyl)methyl]pyrazol-4-yl]-1,3-dipropyl-1,3,7-trihydropurine-2,6-dione;
8-{1-[(4-fluorophenyl)methyl]pyrazol-4-yl)}-1,3-dipropyl-1,3,7-trihydropurine-2,6-dione;
8-{1-[(4-methoxyphenyl)methyl]pyrazol-4-yl]-1,3-dipropyl-1,3,7-trihydropurine-2,6-dione;
2-[4-(2,6-dioxo-1,3-dipropyl-1,3,7-trihydropurin-8-yl)pyrazolyl]acetic acid;
8-[1-(2-hydroxyethyl)pyrazol-4-yl]-1,3-dipropyl-1,3,7-trihydropurine-2,6-dione;
2-[4-(2,6-dioxo-1,3-dipropyl(1,3,7-trihydropurin-8-yl))pyrazolyl]-2-phenylacetic acid;
2-[4-(2,6-dioxo-1,3-dipropyl(1,3,7-trihydropurin-8-yl))pyrazolyl]-2-(4-fluorophenyl)acetic acid;
2-[4-(2,6-dioxo-1,3-dipropyl(1,3,7-trihydropurin-8-yl)pyrazolyl]propanoic acid;
8-[1-(phenylethyl)pyrazol-4-yl]-1,3-dipropyl-1,3,7-trihydropurine-2,6-dione;
8-[1-(4-chlorophenyl)-5-(trifluoromethyl)pyrazol-4-yl]-1,3-dipropyl-1,3,7-trihydropurine-2,6-dione;
8-[1-phenyl-5-(trifluoromethyl)pyrazol-4-yl]-1,3-dipropyl-1,3,7-trihydropurine-2,6-dione;
8-(1-phenyl-5-propylpyrazol-4-yl)-1,3-dipropyl-1,3,7-trihydropurine-2,6-dione;
8-(5-methyl-1-phenylpyrazol-4-yl)-1,3-dipropyl-1,3,7-trihydropurine-2,6-dione; ethyl 2-[4-(2,6-dioxo-1,3-dipropyl(1,3,7-trihydropurin-8-yl))pyrazolyl]-2-phenylacetate;
1,3-dimethyl-8-(1-{[3-(trifluoromethyl)phenyl]methyl}pyrazol-4-yl)-1,3,7-trihydropurine-2,6-dione;
1,3-dipropyl-8-{1-[(3-fluorophenyl)methyl]pyrazol-4-yl}-1,3,7-trihydropurine-2,6-dione;
1,3-dipropyl-8-[1-phenylpyrazol-4-yl}-1,3,7-trihydropurine-2,6-dione;
1,3-dipropyl-8-[1,3-dimethylpyrazol-4-yl}-1,3,7-trihydropurine-2,6-dione;
1,3-dipropyl-8-[1-ethyl-3-methylpyrazol-4-yl}-1,3,7-trihydropurine-2,6-dione;
1,3-dibutyl-8-[1-benzylpyrazol-4-yl]-1,3,7-trihydropurine-2,6-dione;
1,3-dibutyl-8-pyrazol-4-yl-1,3,7-trihydropurine-2,6-dione;
1,3-dipropyl-8-pyrazol-4-yl-1,3,7-trihydropurine-2,6-dione;
1,3-dimethyl-8-[1-benzylpyrazol-4-yl]-1,3,7-trihydropurine-2,6-dione;
1,3-diethyl-8-[1-benzylpyrazol-4-yl]-1,3,7-trihydropurine-2,6-dione;
1,3-dipropyl-8-{1-[(2-methoxyphenyl)methyl]pyrazol-4-yl}-1,3,7-trihydropurine-2,6-dione;
1,3-di-(sec-butyl)-8-[1-benzylpyrazol-4-yl]-1,3,7-trihydropurine-2,6-dione;
1,3-di(sec-butyl)-8-{1-[(3-trifluoromethylphenyl)methyl]pyrazol-4-yl}-1,3,7-trihydropurine-2,6-dione;
1,3-di(sec-butyl)-8-{1-[(3-fluorophenyl)methyl]pyrazol-4-yl}-1,3,7-trihydropurine-2,6-dione;
1,3-dimethyl-8-{1-[(3-fluorophenyl)methyl]pyrazol-4-yl}-1,3,7-trihydropurine-2,6-dione;
1,3-dipropyl-8-{1-[(2,5-dichlorophenyl)methyl]pyrazol-4-yl}-1,3,7-trihydropurine-2,6-dione;
1,3-diethyl-8-{1-[(3-fluorophenyl)methyl]pyrazol-4-yl}-1,3,7-trihydropurine-2,6-dione;
1,3-diethyl-8-{1-[(3-trifluoromethylphenyl)methyl]pyrazol-4-yl}-1,3,7-trihydropurine-2,6-dione;
1,3-dipropyl-8-1-[(4-carboxyphenyl)methyl]pyrazol-4-yl}-1,3,7-trihydropurine-2,6-dione;
1,3-dipropyl-8-(1-{[3-(trifluoromethyl)phenyl]methyl}pyrazol-4-yl)-1,3,7-trihydropurine-2,6-dione;
1,3-dipropyl-8-(1-{[3-(trifluoromethyl)phenyl]ethyl}pyrazol-4-yl)-1,3,7-trihydropurine-2,6-dione; and
2-[4-(2,6-dioxo-1,3-dipropyl(1,3,7-trihydropurin-8-yl))pyrazolyl]-2-phenylacetic acid;
1,3-diethyl-8-(pyrazol-4-yl)-1,3,7-trihydropurine-2,6-dione.
8-(1-{[3-(4-chlorophenyl)(1,2,4-oxadiazol-5-yl)]methyl}pyrazol-4-yl)-1,3-dipropyl-1,3,7-trihydropurine-2,6-dione;
8-{1-[(5-phenyl(1,2,4-oxadiazol-3-yl))methyl]pyrazol-4-yl}-1,3-dipropyl-1,3,7-trihydropurine-2,6-dione;
1,3-dipropyl-8-[1-({5-[4-(trifluoromethyl)phenyl](1,2,4-oxadiazol-3-yl)}methyl)pyrazol-4-yl]-1,3,7-trihydropurine-2,6-dione;
8-{1-[(5-phenylisoxazol-3-yl)methyl]pyrazol-4-yl}-1,3-dipropyl-1,3,7-trihydropurine-2,6-dione;
8-(1-{[5-(2-chlorophenyl)isoxazol-3-yl]methyl}pyrazol-4-yl)-1,3-dipropyl-1,3,7-trihydropurine-2,6-dione;
8-(1-{[5-(4-chlorophenyl)isoxazol-3-yl]methyl}pyrazol-4-yl)-1,3-dipropyl-1,3,7-trihydropurine-2,6-dione;
8-(1-{[5-(3,4-dichlorophenyl)isoxazol-3-yl]methyl}pyrazol-4-yl)-1,3-dipropyl-1,3,7-trihydropurine-2,6-dione;
1,3-dipropyl-8-[1-({5-[4-(trifluoromethyl)phenyl]isoxazol-3-yl}methyl)pyrazol-4-yl]-1,3,7-trihydropurine-2,6-dione;
8-{1-[(6-chloro-2-fluorophenyl)methyl]pyrazol-4-yl}-1,3-dipropyl-1,3,7-trihydropurine-2,6-dione;
8-{1-[(2,3-difluorophenyl)methyl]pyrazol-4-yl}-1,3-dipropyl-1,3,7-trihydropurine-2,6-dione;
8-{1-[(2,4-difluorophenyl)methyl]pyrazol-4-yl}-1,3-dipropyl-1,3,7-trihydropurine-2,6-dione;
8-{1-[(2,6-difluorophenyl)methyl]pyrazol-4-yl}-1,3-dipropyl-1,3,7-trihydropurine-2,6-dione;
8-{1-[(3,4-difluorophenyl)methyl]pyrazol-4-yl}-1,3-dipropyl-1,3,7-trihydropurine-2,6-dione;
8-(1-{[4-fluoro-3-(trifluoromethyl)phenyl]methyl}pyrazol-4-yl)-1,3-dipropyl-1,3,7-trihydropurine-2,6-dione;
8-(1-{[4-chloro-3-(trifluoromethyl)phenyl]methyl}pyrazol-4-yl)-1,3-dipropyl-1,3,7-trihydropurine-2,6-dione;
1,3-dipropyl-8-(1-{[3-(trifluoromethyl)phenyl]ethyl}pyrazol-4-yl)-1,3,7-trihydropurine-2,6-dione;
8-(1-{[3-chloro-2-fluoro-5-(trifluoromethyl)phenyl]methyl}pyrazol-4-yl)-1,3-dipropyl-1,3,7-trihydropurine-2,6-dione;
8-(1-{[4-methoxy-3-(trifluoromethyl)phenyl]methyl}pyrazol-4-yl)-1,3-dipropyl-1,3,7-trihydropurine-2,6-dione;
8-(1-{[3,5-bis(trifluoromethyl)phenyl]methyl}pyrazol-4-yl)-1,3-dipropyl-1,3,7-trihydropurine-2,6-dione;
8-{1-[(3-phenylisoxazol-5-yl)methyl]pyrazol-4-yl}-1,3-dipropyl-1,3,7-trihydropurine-2,6-dione;
1,3-dipropyl-8-[1-(2-pyridylmethyl)pyrazol-4-yl]-1,3,7-trihydropurine-2,6-dione;
1,3-dipropyl-8-[1-({2-[4-(trifluoromethyl)phenyl](1,3-oxazol-4-yl)}methyl)pyrazol-4-yl]-1,3,7-trihydropurine-2,6-dione;

8-(1-{[5-(2,4-difluorophenyl)isoxazol-3-yl]
  Methyl}pyrazol-4-yl)-1,3-dipropyl-1,3,7-trihydropurine-
  2,6-dione;
1,3-dipropyl-8-{1-[(2,4,6-trifluorophenyl)methyl]pyrazol-
  4-yl}-1,3,7-trihydropurine-2,6-dione;
8-{1-[(3-chloro-2-fluorophenyl)methyl]pyrazol-4-yl}-1,3-
  dipropyl-1,3,7-trihydropurine-2,6-dione;
8-{1-[(2-fluoro-3-methylphenyl)methyl]pyrazol-4-yl}-1,3-
  dipropyl-1,3,7-trihydropurine-2,6-dione;
8-(1-{[2-chloro-5-(trifluoromethyl)phenyl]methyl}pyrazol-
  4-yl)-1,3-dipropyl-1,3,7-trihydropurine-2,6-dione;
1,3-dipropyl-8-[1-({5-[3-(trifluoromethyl)phenyl](1,2,4-
  oxadiazol-3-yl)}methyl)pyrazol-4-yl]-1,3,7-trihydropu-
  rine-2,6-dione;
1,3-dipropyl-8-[1-(4-pyridylmethyl)pyrazol-4-yl]-1,3,7-tri-
  hydropurine-2,6-dione;
1,3-dipropyl-8-[1-(3-pyridylmethyl)pyrazol-4-yl]-1,3,7-tri-
  hydropurine-2,6-dione;
8-[1-((1R)indanyl)pyrazol-4-yl]-1,3-dipropyl-1,3,7-trihy-
  dropurine-2,6-dione;
8-[1-((1S)indanyl)pyrazol-4-yl]-1,3-dipropyl-1,3,7-trihy-
  dropurine-2,6-dione;
methyl 3-{[4-(2,6-dioxo-1,3-dipropyl-1,3,7-trihydropurin-
  8-yl)pyrazolyl]methyl}-benzoate;
3-{[4-(2,6-dioxo-1,3-dipropyl-1,3,7-trihydropurin-8-yl)
  pyrazolyl]methyl}benzoic acid;
1,3-dipropyl-8-(1-{[6-(trifluoromethyl)(3-pyridyl)]
  methyl}pyrazol-4-yl)-1,3,7-trihydropurine-2,6-dione;
8-{1-[(6-chloro(3-pyridyl))methyl]pyrazol-4-yl}-1,3-dipro-
  pyl-1,3,7-trihydropurine-2,6-dione;
1,3-dipropyl-8-{1-[(3-(1H-1,2,3,4-tetraazol-5-yl)phenyl)
  methyl]pyrazol-4-yl}-1,3,7-trihydropurine-2,6-dione;
4-{[4-(2,6-dioxo-1,3-dipropyl-1,3,7-trihydropurin-8-yl)
  pyrazolyl]metbyl}benzene -carbonitrile;
8-{1-[(4-methoxy-3,5-dimethyl(2-pyridyl))methyl]pyrazol-
  4-yl}-1,3-dipropyl-1,3,7-trihydropurine-2,6-dione;
8-{1-[(3,4-dimethoxy(2-pyridyl))methyl]pyrazol-4-yl}-1,3-
  dipropyl-1,3,7-trihydropurine-2,6-dione;
8-{1-[(5-chloro(2-thienyl))methyl]pyrazol-4-yl}-1,3-dipro-
  pyl-1,3,7-trihydropurine-2,6-dione; and
6-{[4-(2,6-dioxo-1,3-dipropyl-1,3,7-trihydropurin-8-yl)
  pyrazolyl]methyl}pyridine-2-carboxylic acid.

C. Preparation of a Compound of Formula I where $R^1$ and $R^2$ are the same, Varying X, Y, and Z Similarly, following the procedure of Example 9A and/or 9B above, other compounds of Formula I are prepared:

EXAMPLE 10
Preparation of a Compound of Formula I

A. Preparation of a Compound of Formula I where $R^1$ and $R^2$ are n-Propyl, X is 1,4-Pyrazolene, $R^3$ is 2-Hydroxyethyl, Y is Methylene, and Z is Phenyl

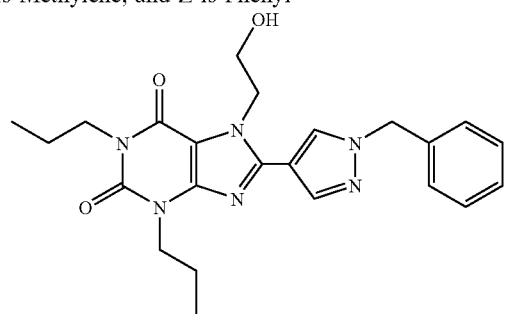

To a solution of 8-(1-benzylpyrazol-4-yl)-1,3-dipropyl-1,3,7-trihydropurine-2,6-dione (0.51 mmol) in N,N-dimethylformamide (2 ml) was added potassium carbonate (5.1 mmol) and 2-bromoethanol (5.1 mmol). The suspension was heated at 70° C. overnight, the solvent removed under reduced pressure, and the residue purified by preparative TLC, yielding pure 7-(2-hydroxyethyl)-8-(1-benzylpyrazol-4-yl)-1,3-dipropyl-1,3,7-trihydropurine-2,6-dione.

B. Preparation of a Compound of Formula I where $R^1$ and $R^2$ are n-Propyl, Varying X, Y, and Z Similarly, following the procedure of 10A above, but replacing 2-bromoethanol with other compounds of formula $R^3LG$, the following compounds of Formula I were prepared:

7-allyl-8-(1-benzylpyrazol-4-yl)-1,3-dipropyl-1,3,7-trihy-
  dropurine-2,6-dione;
7-(methylethyl)-8-{4-[5-(2-methoxyphenyl)-[1,2,4]oxadia-
  zol-3-ylmethoxy]phenyl}-1,3-dipropyl-1,3,7-trihydropu-
  rine-2,6-dione;
7-(2-methoxyethyl)-8-{4-[5-(2-methoxyphenyl)-[1,2,4]oxa-
  diazol-3-ylmethoxy]phenyl}-1,3-dipropyl-1,3,7-trihydro-
  purine-2,6-dione;
7-methyl-8-{4-[5-(2-methoxyphenyl)-[1,2,4]oxadiazol-3-
  ylmethoxy]phenyl}-1,3-dipropyl-1,3,7-trihydropurine-2,
  6-dione; and
7-(prop-2-enyl)-8-{4-[5-(2-methoxyphenyl)-[1,2,4]oxadia-
  zol-3-ylmethoxy]phenyl}-1,3-dipropyl-1,3,7-trihydropu-
  rine-2,6-dione.

C. Preparation of a Compound of Formula I where $R^1$ and $R^2$ are n-Propyl, Varying X, Y, and Z Similarly, following the procedure of 10A above, but replacing 2-bromoethanol with other compounds of formula $R^3LG$, other compounds of Formula I are prepared:

EXAMPLE 11

Preparation of a Compound of Formula (22)

A. Preparation of a Compound of Formula HO—C(O)—XYZ in which X is Phenyl, Y is —O—$CH_2$—, and Z is 5-(2-Methoxyphenyl)-[1,2,4]oxadiazol-3-yl

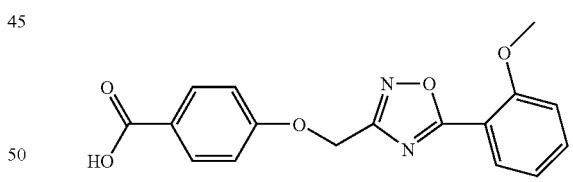

a) A solution of methyl 4-hydroxybenzoate (3.04 g, 20 mmol) and 3-chloromethyl-5-(2-methoxyphenyl)-[1,2,4] oxadiazole (4.48 g, 20 mmol) in acetone (200 ml) was refluxed overnight. The mixture was filtered, solvent removed from the filtrate, and the residue was dissolved in ethyl acetate. Methanol was added to this solution to precipitate the product, methyl 4-{2-[5-(2-methoxyphenyl)-1,2,4-oxadiazol-3-yl]methoxy}benzoate.

b) A solution of methyl 4-{2-[5-(2-methoxyphenyl)-1,2,4-oxadiazol-3-yl]methoxy}benzoate (5.0 g) and potassium hydroxide (10 g) in methanol(200 ml) was refluxed for 4.5 hours. The solvent was removed under reduced pressure, and the residue partitioned between methylene chloride and water. The aqueous layer was acidified with 6N hydrochloric acid to pH 3, and the precipitate extracted into ethyl acetate. The solvent was removed under reduced pressure to give 4-{2-[5-(2-methoxyphenyl)-1,2,4-oxadiazol-3-yl]methoxy}benzoic acid.

B. Preparation of a Compound of Formula HO—C(O)—XYZ, Varying X, Y and Z

Similarly, following the procedure of 11A above, but replacing 3-chloromethyl-5-(2-methoxyphenyl)-[1,2,4]oxadiazole with other 3-chloromethyl-5-substituted-[1,2,4]oxadiazoles, the following compounds of formula HO—C(O)—XYZ I were prepared:

4-{2-[5-(3-fluorophenyl)-1,2,4-oxadiazol-3-yl]methoxy}benzoic acid;

4-{2-[5-cyclopentyl)-1,2,4-oxadiazol-3-yl]methoxy}benzoic acid; and

4-{2-[5-cyclohexyl)-1,2,4-oxadiazol-3-yl]methoxy}benzoic acid.

C. Preparation of a Compound of Formula HO—C(O)—XYZ, Varying X, Y and Z

Similarly, following the procedure of 11A above, but replacing 3-chloromethyl-5-(2-methoxyphenyl)-[1,2,4]oxadiazole with other 3-chloromethyl-5-substituted-[1,2,4]oxadiazoles, other compounds of formula HO—C(O)—XYZ I are prepared:

EXAMPLE 12

Preparation of a Compound of Formula I

A. Preparation of a Compound of Formula I where $R^1$ and $R^2$ are n-Propyl $R^3$ is Hydrogen, X is 1,4-Phenylene, Y is —O(CH$_2$)—, and Z is 5-(2-Methoxyphenyl)-[1,2,4]oxadiazol-3-yl

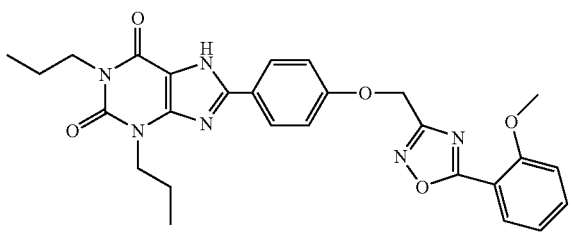

A mixture of 4-{2-[5-(2-methoxyphenyl)-1,2,4-oxadiazol-3-yl]methoxy}benzoic acid (3.0 g), 5,6-diamino-1,3-dipropyl-1,3-dihydropyrimidine-2,4-dione (3.2 g) and 1-[3-(dimethylamino)propyl]-3-ethylcarbodiimide hydrochloride (3.0 g)in N,N-dimethyl-formamide (50 ml) was stirred overnight at room temperature. The solvent was removed under reduced pressure, and the residue dried under vacuum for 1 hour. To this was added 150 ml of 2N sodium hydroxide, and the mixture was heated at 120° C. for 2 hours. The mixture was cooled to 0° C., and acidified with 6N hydrochloric acid to pH 2-3. The mixture was partitioned between water and ethyl acetate, and the ethyl acetate layer separated along with some solid product. This mixture was washed with water, solvent removed from the organic layer to a volume of about 20 ml. The solid thus obtained was filtered off, washed with ethyl acetate, and once with ethyl acetate/methanol (1:1). The solid was dried under vacuum to provide 8-{4-[5-(2-methoxyphenyl)-[1,2,4]-oxadiazol-3-ylmethoxy]phenyl}-1,3-dipropyl-1,3,7-trihydropurine-2,6-dione, a compound of Formula I.

B. Preparation of a Compound of Formula I where $R^1$ and $R^2$ are n-Propyl, Varying X, Y, and Z Similarly, following the procedure of 12A above, but optionally replacing 4-{2-[5-(2-methoxyphenyl)-1,2,4-oxadiazol-3-yl]methoxy}benzoic acid with other compounds of formula (22), and optionally replacing 5,6-diamino-1,3-dipropyl-1,3-dihydropyrimidine-2,4-dione with similar compounds, the following compounds of Formula I were prepared:

8-{4-[(3,5-dimethylisoxazol-4-yl)methoxy]phenyl}-1,3-dipropyl-1,3,7-trihydropurine-2,6-dione;

8-{4-[2-phenoxyethoxy)phenyl-[1,2,4]-oxadiazol-3-ylmethoxy]phenyl}-1,3-dipropyl-1,3,7-trihydropurine-2,6-dione;

8-{4-[5-(4-fluorophenyl)-[1,2,4]-oxadiazol-3-ylmethoxy]phenyl}-1,3-dipropyl-1,3,7-trihydropurine-2,6-dione;

8-{4-[5-(3-cyclohexyl)-[1,2,4]-oxadiazol-3-ylmethoxy]phenyl}-1,3-dipropyl-1,3,7-trihydropurine-2,6-dione;

8-{4-[5-(3-cyclopentyl)-[1,2,4]-oxadiazol-3-ylmethoxy]phenyl}-1,3-dipropyl-1,3,7-trihydropurine-2,6-dione;

8-{4-[3-(3-chlorophenyl)-[1,2,4]-oxadiazol-5-ylmethoxy]-phenyl}-1,3-dipropyl-1,3,7-trihydropurine-2,6-dione;

8-{4-[3-(4-biphenyl)-[1,2,4]-oxadiazol-5-ylmethoxy]-phenyl}-1,3-dipropyl-1,3,7-trihydropurine-2,6-dione;

8-{4-[3-(4-isopropylphenyl)-[1,2,4]-oxadiazol-5-ylmethoxy]-phenyl}-1,3-dipropyl-1,3,7-trihydropurine-2,6-dione;

8-{4-[3-(4-tert-butylphenyl)-[1,2,4]-oxadiazol-5-ylmethoxy]-phenyl}-1,3-dipropyl-1,3,7-trihydropurine-2,6-dione;

8-{4-[5-(4-iodopyrazol-1-yl)ethoxy]-phenyl}-1,3-dipropyl-1,3,7-trihydropurine-2,6-dione;

8-{4-[5-(4-chlorophenyl)-[1,2,4]-oxadiazol-3-ylmethoxy]-phenyl}-1,3-dipropyl-1,3,7-trihydropurine-2,6-dione;

8-{4-[3-(4-methylphenyl)-[1,2,4]-oxadiazol-5-ylmethoxy]-phenyl}-1,3-dipropyl-1,3,7-trihydropurine-2,6-dione; and 8-{4-[3,5-dimethyl-[1,2,4]-oxadiazol-5-ylmethoxy]-phenyl}-1,3-dipropyl-1,3,7-trihydropurine-2,6-dione.

C. Preparation of a Compound of Formula I where $R^1$ and $R^2$ are n-Propyl, Varying X, Y, and Z Similarly, following the procedure of 12A above, but optionally replacing 4-{2-[5-(2-methoxyphenyl)-1,2,4-oxadiazol-3-yl]methoxy}benzoic acid with other compounds of formula (22), and optionally replacing 5,6-diamino-1,3-dipropyl-1,3-dihydropyrimidine-2,4-dione with other similar compounds, other compounds of Formula I are prepared.

EXAMPLE 13

Preparation of a Compound of Formula I

A. Preparation of a Compound of Formula I where $R^1$ and $R^2$ are n-Propyl, $R^3$ is Hydrogen, X is 1,4-Phenylene, Y is —O(CH$_2$)—, and Z is 5-(2-Methoxyphenyl)-[1,2,4]oxadiazol-3-yl

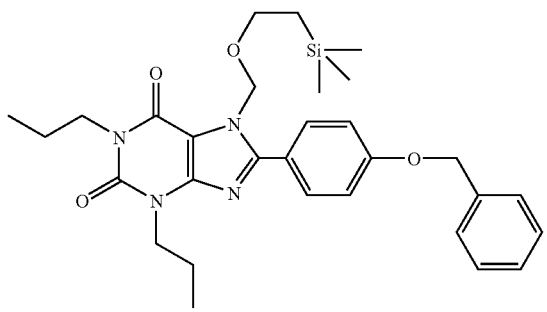

a) To a solution of 8-[4-(phenylmethoxy)phenyl]-1,3-dipropyl-1,3,7-trihydropurine-2,6-dione (3.8 g, 9.08 mmoles) in anhydrous dimethylformamide (100 mL) was added potassium carbonate (6.27 g, 45.4 mmoles), followed by 2-(trimethylsilyl)ethoxymethyl chloride (3.21 mL, 18 mmoles), and the mixture stirred at 70° C. for 72 hours. The solvent was removed under reduced pressure, and the residue purified by flash column chromatography, eluting with 30% EtOAc/Hexanes, to give 3.7 g of 7-[(2-trimethylsilyl)ethoxymethyl]-8-[4-(phenylmethoxy)phenyl]-1,3-dipropyl-1,3,7-trihydropurine-2,6-dione.

b)

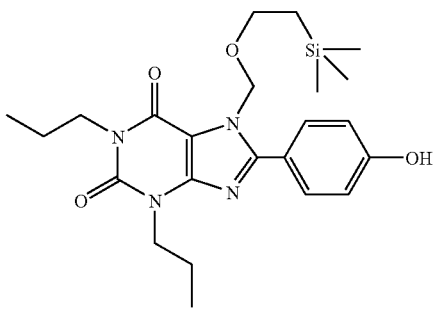

7-[(2-trimethylsilyl)ethoxymethyl]-8-[4-(phenylmethoxy)phenyl]-1,3-dipropyl-1,3,7-trihydropurine-2,6-dione (1.74 g, 3.17 mmoles) was dissolved in methanol (100 mL), and to it was added Pearlmann's catalyst (1.0 g). The resulting suspension was stirred at room temperature under a positive hydrogen pressure for 16 hours. The suspension was filtered through celite, washed several times with 50:50 methylene chloride:methanol, and the filtrate was evaporated to give 7-[(2-trimethylsilyl)ethoxymethyl]-8-[4-hydroxyphenyl]-1,3-dipropyl-1,3,7-trihydropurine-2,6-dione (1.2 g) as a white solid.

c)

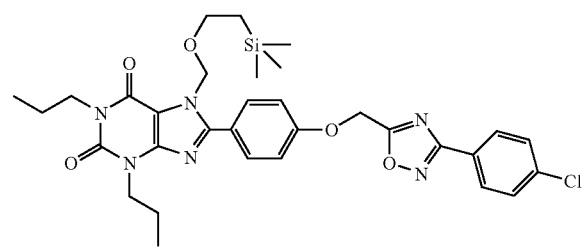

7-[(2-trimethylsilyl)ethoxymethyl]-8-[4-hydroxyphenyl]-1,3-dipropyl-1,3,7-trihydropurine-2,6-dione (50 mg, 0.1 mmoles) was dissolved in acetone (2.5 mL), to which was added potassium carbonate (0.5 g), followed by 5-chloromethyl 3-[(4-chloro)phenyl]oxadiazole (25 mg, 0.1 mmoles), and the mixture was stirred at 60 deg C. for 16 hours. The solvent was removed under reduced pressure, and evaporated and the residue was subjected to preparative thin layer chromatography, eluting with 30% EtOAc/Hexanes, to provide 7-(2-trimethylsilyl)ethoxymethyl-8-(4-{[3-(4-chlorophenyl)(1,2,4-oxadiazol-5-yl)]methoxy}phenyl)-1,3-dipropyl-1,3,7-trihydropurine-2,6-dione (50 mg).

d)

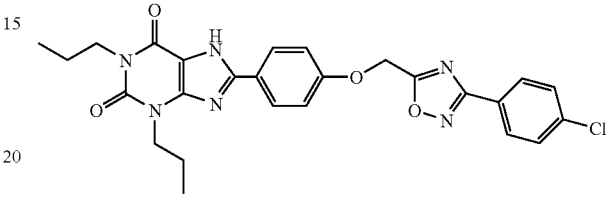

7-(2-trimethylsilyl)ethoxymethyl-8-(4-{[3-(4-chlorophenyl)(1,2,4-oxadiazol-5-yl)]methoxy}phenyl)-1,3-dipropyl-1,3,7-trihydropurine-2,6-dione was dissolved in ethanol (2 mL), to which was added 1M HCL (0.5 mL). The mixture was refluxed for 2 hours. The resulting white residue was collected by evaporating the solvent under reduced pressure and washing the residue with ethanol (3×2 mL), to give pure 8-(4-{[3-(4-chlorophenyl)(1,2,4-oxadiazol-5-yl)]methoxy}phenyl)-1,3-dipropyl-1,3,7-trihydropurine-2,6-dione.

B. Preparation of a Compound of Formula I where $R^1$ and $R^2$ are n-Propyl, Varying X, Y, and Z Similarly, following the procedure of 13A above, but replacing 5-chloromethyl 3-[(4-chloro)phenyl]oxadiazole with similar compounds, the following compounds of Formula I were prepared:

8-(4-{[5-(4-chlorophenyl)(1,2,4-oxadiazol-3-yl)]methoxy}phenyl)-1,3-dipropyl-1,3,7-trihydropurine-2,6-dione;

8-(4-{[3-(4-methylphenyl)(1,2,4-oxadiazol-5-yl)]methoxy}phenyl)-1,3-dipropyl-1,3,7-trihydropurine-2,6-dione;

8-{4-[2-(4-iodopyrazolyl)ethoxy]phenyl}-1,3-dipropyl-1,3,7-trihydropurine-2,6-dione;

8-{4-[2-(4-methylpyrazolyl)ethoxy]phenyl}-1,3-dipropyl-1,3,7-trihydropurine-2,6-dione;

8-{4-[(5-methylisoxazol-3-yl)methoxy]phenyl}-1,3-dipropyl-1,3,7-trihydropurine-2,6-dione;

8-(1-{[5-(2-methoxyphenyl)(1,2,4-oxadiazol-3-yl)]methyl}pyrazol-4-yl)-1,3-dipropyl-1,3,7-trihydropurine-2,6-dione;

N-(2,6-dimethylphenyl)-2-[4-(2,6-dioxo-1,3-dipropyl(1,3,7-trihydropurin-8-yl))pyrazolyl]acetamide;

8-(1-{[3-(4-methylphenyl)(1,2,4-oxadiazol-5-yl)]methyl}pyrazol-4-yl)-1,3-dipropyl-1,3,7-trihydropurine-2,6-dione;

8-{1-[2-(1,3-dioxoisoindolin-2-yl)ethyl]pyrazol-4-yl}-1,3-dipropyl-1,3,7-trihydropurine-2,6-dione;

2-[4-(2,6-dioxo-1,3-dipropyl(1,3,7-trihydropurin-8-yl))pyrazolyl]-N-(2-chlorophenyl)acetamide;

2-[4-(2,6-dioxo-1,3-dipropyl(1,3,7-trihydropurin-8-yl))pyrazolyl]-N-phenylacetamide;

1,3-dipropyl-8-pyrazol-4-yl-1,3,7-trihydropurine-2,6-dione;

methyl 4-(3-{[4-(2,6-dioxo-1,3-dipropyl-1,3,7-trihydropurin-8-yl)phenoxy]methyl}-1,2,4-oxadiazol-5-yl)benzoate;

1,3-dipropyl-8-[4-({5-[2-(trifluoromethoxy)phenyl](1,2,4-oxadiazol-3-yl)}methoxy)phenyl]-1,3,7-trihydropurine-2,6-dione;

8-(4-{[5-(2-bromophenyl)(1,2,4-oxadiazol-3-yl)]methoxy}phenyl)-1,3-dipropyl-1,3,7-trihydropurine-2,6-dione;

8-(4-{[5-(2,4-dimethoxyphenyl)(1,2,4-oxadiazol-3-yl)]methoxy}phenyl)-1,3-dipropyl-1,3,7-trihydropurine-2,6-dione;

8-{4-[(5-methylisoxazol-3-yl)methoxy]phenyl}-1,3-dipropyl-1,3,7-trihydropurine-2,6-dione;

8-{1-[(2-methylphenyl)methyl]pyrazol-4-yl}-1,3-dipropyl-1,3,7-trihydropurine-2,6-dione;

8-{1-[(3-methylphenyl)methyl]pyrazol-4-yl}-1,3-dipropyl-1,3,7-trihydropurine-2,6-dione;

1,3-dipropyl-8-(1-{[2-(trifluoromethyl)phenyl]methyl}pyrazol-4-yl)-1,3,7-trihydropurine-2,6-dione;

8-{1-[(4-methylphenyl)methyl]pyrazol-4-yl}-1,3-dipropyl-1,3,7-trihydropurine-2,6-dione 8-{1-[(2-methoxyphenyl)methyl]pyrazol-4-yl}-1,3-dipropyl-1,3,7-trihydropurine-2,6-dione;

8-{1-[(2-fluorophenyl)methyl]pyrazol-4-yl}-1,3-dipropyl-1,3,7-trihydropurine-2,6-dione;

8-{1-[(3-methoxyphenyl)methyl]pyrazol-4-yl}-1,3-dipropyl-1,3,7-trihydropurine-2,6-dione;

8-1-[(3-fluorophenyl)methyl]pyrazol-4-yl}-1,3-dipropyl-1,3,7-trihydropurine-2,6-dione;

8-{1-[(3-chlorophenyl)methyl]pyrazol-4-yl}-1,3-dipropyl-1,3,7-trihydropurine-2,6-dione; 1,3-dipropyl-8-(1-{[3-(trifluoromethyl)phenyl]methyl}pyrazol-4-yl)-1,3,7-trihydropurine-2,6-dione;

8-{1-[(2-chlorophenyl)methyl]pyrazol-4-y}-1,3-dipropyl-1,3,7-trihydropurine-2,6-dione;

1,3-dipropyl-8-(1-{[4-(trifluoromethyl)phenyl]methyl}pyrazol-4-yl)-1,3,7-trihydropurine-2,6-dione;

8-{1-[(4-chlorophenyl)methyl]pyrazol-4-yl}-1,3-dipropyl-1,3,7-trihydropurine-2,6-dione;

8-{1-[(4-fluorophenyl)methyl]pyrazol-4-yl}-1,3-dipropyl-1,3,7-trihydropurine-2,6-dione; and 8-{1-[(4-fluorophenyl)methyl]pyrazol-4-yl}-1,3-dipropyl-1,3,7-trihydropurine-2,6-dione.

C. Preparation of a Compound of Formula I where $R^1$ and $R^2$ are n-Propyl, Varying X, Y, and Z Similarly, following the procedure of 13A above, but replacing 5-chloromethyl 3-[(4-chloro)phenyl] oxadiazole with similar compounds, other following compounds of Formula I are prepared:

EXAMPLE 14

Preparation of a Compound of Formula (23)

A. Preparation of a Compound of Formula (23) in which $R^1$ is n-Butyl

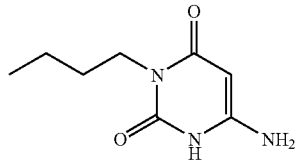

(23)

A mixture of 6-aminouracil (5 g, 10 mmol), hexamethyldisilazane (40 ml), and ammonium sulfate (260 mg, 1.97 mmol) was refluxed for 4 hours. Excess HMDS was removed under reduced pressure to provide the trimethylsilylated derivative of 6-aminouracil.

The product was combined with 1-iodobutane (10 ml) and heated in an oil bath at 130° C. for 3 days. The reaction mixture was then cooled to 0° C., and saturated aqueous sodium bicarbonate added. The resulting precipitate was filtered off, washed with water, to provide 6-amino-3-butyl-1,3-dihydropyrimidine-2,4-dione, a compound of formula (23), which was used in the next reaction with no further purification.

B. Preparation of Other Compounds of Formula (23)

Similarly, following the procedure of 14A above, but replacing 1-iodobutane with other halides of formula $R^1Hal$, the following compounds of formula (23) were prepared:
6-amino-3-ethyl-1,3-dihydropyrimidine-2,4-dione;
6-amino-3-n-propyl-1,3-dihydropyrimidine-2,4-dione;
6-amino-3-cyclopropylmethyl-1,3-dihydropyrimidine-2,4-dione;
6-amino-3-(2-methylpropyl)-1,3-dihydropyrimidine-2,4-dione;
6-amino-3-benzyl-1,3-dihydropyrimidine-2,4-dione; and
6-amino-3-ethynyl-1,3-dihydropyrimidine-2,4-dione.

C. Preparation of Other Compounds of Formula (23)

Similarly, following the procedure of 14A above, but replacing 1-iodobutane with other halides of formula $R^1Hal$, the following compounds of formula (23) are prepared.
6-amino-3-methyl-1,3-dihydropyrimidine-2,4-dione;
6-amino-3-isopropyl-1,3-dihydropyrimidine-2,4-dione;
6-amino-3-n-pentyl-1,3-dihydropyrimidine-2,4-dione;
6-amino-3-propylpentyl-1,3-dihydropyrirriidine-2,4-dione;
6-amino-3-(2-phenylethyl)-1,3-dihydropyrimidine-2,4-dione;
6-amino-3-(2-methoxyethyl)-1,3-dihydropyrimidine-2,4-dione;
6-amino-3-(3-hydroxypropyl)-1,3-dihydropyrimidine-2,4-dione;
6-amino-3-(4-fluorobutyl)-1,3-dihydropyrimidine-2,4-dione;
6-amino-3-(2-ethylcarboxyethyl)-1,3-dihydropyrimidine-2,4-dione;
6-amino-3-ethenyl-1,3-dihydropyrimidine-2,4-dione;
6-amino-3-cyclopentyl-1,3-dihydropyrimidine-2,4-dione;
6-amino-3-(3-hydroxycyclopentyl)-1,3-dihydropymmidine-2,4-dione;
6-amino-3-cyclohexyl-1,3-dihydropyrimidine-2,4-dione;
6-amino-3-cyclopropylmethyl-1,3-dihydropyrimidine-2,4-dione;
6-amino-3-phenyl-1,3-dihydropyrimidine-2,4-dione;
6-amino-3-(pyrid-3-yl)-1,3-dihydropyrimidine-2,4-dione;
6-amino-3-(pyrid-3-ylmethyl)-1,3-dihydropyrimidine-2,4-dione;

6-amino-3-(tetrahydrofuran-3-yl)-1,3-dihydropyrimidine-2, 4-dione; and
6-amino-3-(piperidin-4-yl)-1,3-dihydropyrimidine-2,4-dione.

D. Preparation of Other Compounds of Formula (23)

Similarly, following the procedure of 14A above, but replacing 1-iodobutane with other halides of formula $R^1$Hal, other compounds of formula (23) are prepared.

EXAMPLE 15

Preparation of a Compound of Formula (24)

A. Preparation of a Compound of Formula (24) in which $R^1$ is n-Butyl

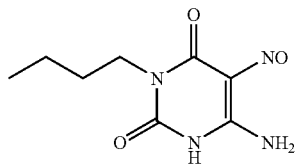

(24)

A mixture of 6-amino-3-butyl-1,3-dihydropyrimidine-2, 4-dione (4.0 g, 21.8 mmol) and aqueous acetic acid (120 ml) was heated at 70° C. until complete solution as attained, and the solution was cooled to 30° C. Sodium nitrite (3 g) was added in small portions while stirring, forming an orange precipitate. The reaction mixture was cooled to 0° C., and the precipitate filtered off, washed with water, and dried under reduced pressure, to provide 5-nitroso-6-amino-3-butyl-1,3-dihydropyrimidine-2,4-dione, which was used in the next reaction with no further purification.

B. Preparation of other Compounds of Formula (24)

Similarly, following the procedure of 15A above, but replacing 6-amino-3-butyl-1,3-dihydropyrimidine-2,4-dione with other compounds of formula (23), the following compounds of formula (24) were prepared:

5-nitroso-6-amino-3-ethyl-1,3-dihydropyrimidine-2,4-dione;
5-nitroso-6-amino-3-n-propyl-1,3-dihydropyrimidine-2,4-dione;
5-nitroso-6-amino-3-cyclopropylmethyl-1,3-dihydropyrimidine-2,4-dione;
5-nitroso-6-amino-3-(2-methylpropyl)-1,3-dihydropyrimidine-2,4-dione;
5-nitroso-6-amino-3-benzyl-1,3-dihydropyrimidine-2,4-dione; and
5-nitroso-6-amino-3-ethynyl-1,3-dihydropyrimidine-2,4-dione.

C. Preparation of Other Compounds of Formula (24)

Similarly, following the procedure of 15A above, but replacing 6-amino-3-butyl-1,3-dihydropyrimidine-2,4-dione with other halides of formula (23), the following compounds of formula (24) are prepared.

5-nitroso-6-amino-3-methyl-1,3-dihydropyrimidine-2,4-dione;
5-nitroso-6-amino-3-isopropyl-1,3-dihydropyrimidine-2,4-dione;
5-nitroso-6-amino-3-n-pentyl-1,3-dihydropyrimidine-2,4-dione;
5-nitroso-6-amino-3-propylpentyl-1,3-dihydropyrimidine-2,4-dione;
5-nitroso-6-amino-3-(2-phenylethyl)-1,3-dihydropyrimidine-2,4-dione;
5-nitroso-6-amino-3-(2-methoxyethyl)-1,3-dihydropyrimidine-2,4-dione;
5-nitroso-6-amino-3-(3-hydroxypropyl)-1,3-dihydropyrimidine-2,4-dione;
5-nitroso-6-amino-3-(4-fluorobutyl)-1,3-dihydropyrimidine-2,4-dione;
5-nitroso-6-amino-3-(2-ethylcarboxyethyl)-1,3-dihydropyrimidine-2,4-dione;
5-nitroso-6-amino-3-ethenyl-1,3-dihydropyrimidine-2,4-dione;
5-nitroso-6-amino-3-cyclopentyl-1,3-dihydropyrimidine-2, 4-dione;
5-nitroso-6-amino-3-(3-hydroxycyclopentyl)-1,3-dihydropyrimidine-2,4-dione;
5-nitroso-6-amino-3-cyclohexyl-1,3-dihydropyrimidine-2, 4-dione;
5-nitroso-6-amino-3-cyclopropylmethyl-1,3-dihydropyrimidine-2,4-dione;
5-nitroso-6-amino-3-phenyl-1, 3-dihydropyrimidine-2,4—dione;
5-nitroso-6-amino-3-pyrid-3-yl)-1,3-dihydropyrimidine-2, 4-dione;
5-nitroso-6-amino-3-(pyrid-3-ylmethyl) 1,3-dihydropyrimidine-2,4-dione;
5-nitroso-6-amino-3-(tetrahydrofuran-3-yl)-1,3-dihydropyrimidine-2,4-dione; and
5-nitroso-6-amino-3-(piperidin-4-yl)-1,3-dihydropyrimidine-2,4-dione.

D. Preparation of Other Compounds of Formula (24)

Similarly, following the procedure of 15A above, but replacing 6-amino-3-butyl-1,3-dihydropyrimidine-2,4-dione with other halides of formula (23), other compounds of formula (24) are prepared.

EXAMPLE 16

Preparation of a Compound of Formula (25)

A. Preparation of a Compound of Formula (25) in which $R^1$ is n-Butyl

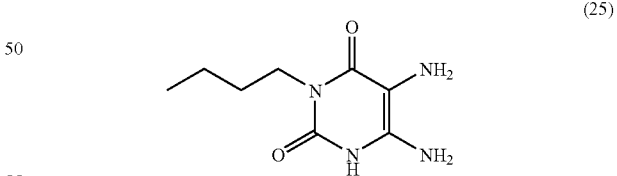

(25)

A mixture of 5-nitroso-6-amino-3-butyl-1,3-dihydropyrimidine-2,4-dione (2.1 g, 10 mmol) and aqueous ammonia (50 ml) was heated at 70° C. until complete solution as attained. Sodium hydrosulfite (7 g) was then added in small portions until the solution became clear and colorless. The reaction mixture was evaporated under reduced pressure until crystals appeared, and was then cooled to 0° C. The precipitate filtered off, washed with cold water, 5,6-diamino-3-butyl-1,3-dihydropyrimidine-2,4-dione, a compound of formula (25), which was used in the next reaction with no further purification.

B. Preparation of Other Compounds of Formula (25)

Similarly, following the procedure of 16A above, but replacing 5-nitroso-6-amino-3-butyl-1,3-dihydropyrimidine-2,4-dione with other compounds of formula (24), the following compounds of formula (25) were prepared:

5,6-diamino-3-ethyl-1,3-dihydropyrimidine-2,4-dione;
5,6-diamino-3-n-propyl-1,3-dihydropyrimidine-2,4-dione;
5,6-diamino-3-cyclopropylmethyl-1,3-dihydropyrimidine-2,4-dione;
5,6-diamino-3-(2-methylpropyl)-1,3-dihydropyrimidine-2,4-dione;
5,6-diamino-3-benzyl-1,3-dihydropyrimidine-2,4-dione; and
5,6-diamino-3-ethynyl-1,3-dihydropyrimidine-2,4-dione.

C. Preparation of Other Compounds of Formula (25)

Similarly, following the procedure of 16A above, but replacing 5-nitroso-6-amino-3-butyl-1,3-dihydropyrimidine-2,4-dione with other compounds of formula (24), the following compounds of formula (24) are prepared.

5,6-diamino-3-methyl-1,3-dihydropyrimidine-2,4-dione;
5,6-diamino-3-isopropyl-1,3-dihydropyrimidine-2,4-dione;
5,6-diamino-3-n-pentyl-1,3-dihydropyrimidine-2,4-dione;
5,6-diamino-3-propylpentyl-1,3-dihydropyrimidine-2,4-dione;
5,6-diamino-3-(2-phenylethyl)-1,3-dihydropyrimidine-2,4-dione;
5,6-diamino-3-(2-methoxyethyl)-1,3-dihydropyrimidine-2,4-dione;
5,6-diamino-3-(3-hydroxypropyl)-1,3-dihydropyrimidine-2,4-dione;
5,6-diamino-3-(4-fluorobutyl)-1,3-dihydropyrimidine-2,4-dione;
5,6-diamino-3-(2-ethylcarboxyethyl)-1,3-dihydropyrimidine-2,4-dione;
5,6-diamino-3-ethenyl-1,3-dihydropyrimidine-2,4-dione;
5,6-diamino-3-cyclopentyl-1,3-dihydropyrimidine-2,4-dione;
5,6-diamino-3-(3-hydroxycyclopentyl)-1,3-dihydropyrimidine-2,4-dione;
5,6-diamino-3-cyclohexyl-1,3-dihydropyrimidine-2,4-dione;
5,6-diamino-3-cyclopropylmethyl-1,3-dihydropyrimidine-2,4-dione;
5,6-diamino-3-phenyl-1,3-dihydropyrimidine-2,4-dione;
5,6-diamino-3-(pyrid-3-yl)-1,3-dihydropyrimidine-2,4-dione;
5,6-diamino-3-(pyrid-3-ylmethyl)-1,3-dihydropyrimidine-2,4-dione;
5,6-diamino-3-(tetrahydrofuran-3-yl)-1,3-dihydropyrimidine-2,4-dione; and
5-nitroso-6-amino-3-(piperidin-4-yl)-1,3-dihydropyrimidine-2,4-dione.

D. Preparation of Other Compounds of Formula (25)

Similarly, following the procedure of 16A above, but replacing 5-nitroso-6-amino-3-butyl-1,3-dihydropyrimidine-2,4-dione with other compounds of formula (24), other compounds of formula (25) are prepared, for example 8-[1-(1-oxy-pyridin-3-ylmethyl)-1H-pyrazol-4-yl]-1,3-dipropyl-3,7-dihydro-purine-2,6-dione.

EXAMPLE 17

Preparation of a Compound of Formula I

A. Preparation of a Compound of Formula I where $R^1$ is n-Butyl, $R^2$ is Hydrogen, $R^3$ is Hydrogen, X is 1,4-Pyrazolene, Y is a Methylene, and Z is Phenyl

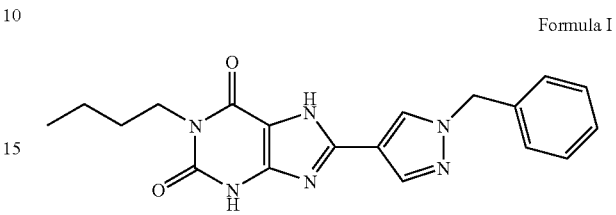

Formula I

To a mixture of 5,6-diamino-3-butyl-1,3-dihydropyrimidine-2,4-dione (1.2 g, 6 mmol) and 1-benzylpyrazole-4-carboxylic acid (1.2 g, 6 mmol) in methanol (30 ml) was added 1-(3-dimethylaminopropyl)-3-ethylcarbodiimide hydrochloride (1.16 g, 6 mmol). A bright yellow solid precipitated. The mixture was stirred overnight at room temperature, and the solid filtered off, washed with methanol, and dried under reduced pressure. The product was combined with hexamethyldisilazane (50 ml) and ammonium sulfate (18 mg) and heated at 130° C. for 48 hours. The solvent was then removed under reduced pressure, and the residue triturated with methanol water (1:1), to provide 1-butyl-8-[1-benzylpyrazol-4-yl]-1,3,7-trihydropurine-2,6-dione, a compound of Formula I.

B. Preparation of Other Compounds of Formula I

Similarly, following the procedure of 17A above, but replacing 5,6-diamino-3-butyl-1,3-dihydropyrimidine-2,4-dione with other compounds of formula (25), the following compounds of Formula I were prepared:

1-butyl-8-[1-benzylpyrazol-4-yl]-1,3,7-trihydropurine-2,6-dione;
1-butyl-8-(pyrazol-4-yl)-1,3,7-trihydropurine-2,6-dione;
1-propyl-8-[1-benzylpyrazol-4-yl]-1,3,7-trihydropurine-2,6-dione;
1-butyl-8-(1-{[3-(trifluoromethyl)phenyl]methyl}pyrazol-4-yl)-1,3,7-trihydropurine-2,6-dione;
1-butyl-8-(1-{[3-fluorophenyl]methyl}pyrazol-4-yl)-1,3,7-trihydropurine-2,6-dione;
1-butyl-8-[1-[(henylethyl)pyrazol-4-yl]-1,3,7-trihydropurine-2,6-dione;
1-(2-methylpropyl)-8-[1-benzylpyrazol-4-yl]-1,3,7-trihydropurine-2,6-dione;
1-propyl-8-(1-{[3-fluorophenyl]methyl}pyrazol-4-yl)-1,3,7-trihydropurine-2,6-dione;
1-propyl-8-(1-{[3-(triiluoromethyl)phenyl]methyl}pyrazol-4-yl)-1,3,7-trihydropurine-2,6-dione;
1-propyl-8-[1-(phenylethyl)pyrazol-4-yl]-1,3,7-trihydropurine-2,6-dione;
8-(1-{[5-(4-chlorophenyl)(1,2,4-oxadiazol-3-yl)]methyl}pyrazol-4-yl)-1-propyl-1,3,7-trihydropurine-2,6-dione;
1-propyl-8-(pyrazol-4-yl)-1,3,7-trihydropurine-2,6-dione;
1-ethyl-8-[1-benzylpyrazol-4-yl]-1,3,7-trihydropurine-2,6-dione);
8-(1-{[5-(4-chlorophenyl)(1,2,4-oxadiazol-3-yl)]methyl}pyrazol-4-yl)-1-butyl-1,3,7-trihydropurine-2,6-dione;

1-ethyl-8-(pyrazol-4-yl)-1,3,7-trihydropurine-2,6-dione;
1-cyclopropylmethyl-8-[1-benzylpyrazol-4-yl]-1,3,7-trihydropurine-2,6-dione;
1-(2-methylpropyl)-8-(pyrazol-4-yl)-1,3,7-trihydropurine-2,6-dione;
1-ethynyl-8-pyrazol-4-yl-1,3,7-trihydropurine-2,6-dione;
1-ethynyl-8-[1-benzylpyrazol-4-yl]-1,3,7-trihydropurine-2,6-dione;
1-benzyl-8-(pyrazol-4-yl)-1,3,7-trihydropurine-2,6-dione;
1-benzyl-8-[1-benzylpyrazol-4-yl]-1,3,7-trihydropurine-2,6-dione;
1-(2-methylpropyl)-8-(1-{[3-fluorophenyl]methyl}pyrazol-4-yl)-1,3,7-trihydropurine-2,6-dione;
1-(2-methylpropyl)-8-(1-{[3-trifluoromethylphenyl]methyl}pyraol-4-yl)-1,3,7-trihydropurine-2,6-dione;
8-[1-benzylpyrazol-4-yl]-1,3,7-trihydropurine-2,6-dione;
1-ethyl-8-{1-[(3-fluorophenyl)methyl]pyrazol-4-yl}-1,3,7-trihydropurine-2,6-dione;
1-ethyl-8-(1-{[3-(trifluoromethyl)phenyl]methyl}pyrazol-4-yl)-1,3,7-trihydropurine-2,6-dione;
1-(2-methylpropyl)-8-{1-[(5-phenylisoxazol-3-yl)methyl]pyrazol-4-yl}-1,3,7-trihydropurine-2,6-dione;
1-(2-methylpropyl)-8-[1-({5-[4-(trifluoromethyl)phenyl](1,2,4-oxadiazol-3-yl)}methyl)pyrazol-4-yl]-1,3,7-trihydropurine-2,6-dione;
8-{-[(2,5-dichlorophenyl)methyl]pyrazol-4-yl}-1-propyl-1,3,7-trihydropurine-2,6-dione;
8-{1-[(3,4-difluorophenyl)methyl]pyrazol-4-yl}-1-propyl-1,3,7-trihydropurine-2,6-dione;
3-{[4-(2,6-dioxo-1-propyl-1,3,7-trihydrbpurin-8-yl)pyrazolyl]methyl}benzoic acid;
8-(1-{[5-(4-chlorophenyl)(1,2,4-oxadiazol-3-yl)]methyl}pyrazol-4-yl)-1-(cyclopropylmethyl)-1,3,7-trihydropurine-2,6-dione;
1-(cyclopropylmethyl)-8-[1-({5-[4-(trifluoromethyl)phenyl](1,2,4-oxadiazol-3-yl)}methyl)pyrazol-4-yl]-1,3,7-trihydropurine-2,6-dione;
1-(cyclopropylmethyl)-8-[1-(2-pyridylmethyl)pyrazol-4-yl]-1,3,7-trihydropurine-2,6-dione;
1-n-butyl-8-[1-(6-trifluoromethylpyridin-3-ylmethyl)pyrazol-4-yl]-1,3,7-trihydropurine-2,6-dione;
8-(1-{[5-(4-chlorophenyl)isoxazol-3-yl]methyl}pyrazol-4-yl)-1-(cyclopropylmethyl)-1,3,7-trihydropurine-2,6-dione;
1-(cyclopropylmethyl)-8-[1-({5-[4-(trifluoromethyl)phenyl]isoxazol-3-yl}methyl)pyrazol-4-yl]-1,3,7-trihydropurine-2,6-dione;
8-(1-{[2-chloro-5-(trifluoromethyl)phenyl]methyl}pyrazol-4-yl)-1-propyl-1,3,7-trihydropurine-2,6-dione;
8-{1-[(5-phenylisoxazol-3-yl)methyl]pyrazol-4-yl}-1-propyl-1,3,7-trihydropurine-2,6-dione;
8-(1-{[5-(4-chlorophenyl)isoxazol-3-yl]methyl}pyrazol-4-yl)-1-propyl-1,3,7-trihydropurine-2,6-dione;
1-propyl-8-[1-({5-[4-(trifluoromethyl)phenyl](1,2,4-oxadiazol-3-yl)}methyl)pyrazol-4-yl]-1,3,7-trihydropurine-2,6-dione; and
8-{1-[(5-phenyl(1,2,4-oxadiazol-3-yl))methyl]pyrazol-4-yl}-1-propyl-1,3,7-trihydropurine-2,6-dione.

C. Preparation of Other Compounds of Formula I

Similarly, following the procedure of 17A above, but optionally replacing 5,6-diamino-3-butyl-1,3-dihydropyrimidine-2,4-dione with other compounds of formula (25), and optionally replacing 1-benzylpyrazole-4-carboxylic acid with other compounds of formula (22), the following compounds of Formula I are prepared.

1-methyl-8-(1-{[3-(trifluoromethyl)phenyl]methyl}pyrazol-4-yl)-1,3,7-trihydropurine-2,6-dione;
1-isopropyl-8-(1-{[3-fluorophenyl]methyl}pyrazol-4-yl)-1,3,7-trihydropurine-2,6-dione;
1-n-pentyl-8-(1-{[3-chlorophenyl]methyl}pyrazol-4-yl)-1,3,7-trihydropurine-2,6-dione;
1-(3-propylpentyl)-8-(1-{[3-fluorophenyl]methyl}pyrazol-4-yl)-1,3,7-trihydropurine-2,6-dione;
1-(2-phenylethyl)-8-[1-{benzyl}pyrazol-4-yl]-1,3,7-trihydropurine-2,6-dione;
1-(2-methoxyethyl)-8-(1-{[3-(trifluoromethyl)phenyl]methyl}pyrazol-4-yl)-1,3,7-trihydropurine-2,6-dione;
1-(3-hydroxypropyl)-8-(1-{[3-fluorophenyl]methyl}pyrazol-4-yl)-1,3,7-trihydropurine-2,6-dione;
1-(4-fluorobutyl)-8-(1-{[3-fluorophenyl]methyl}pyrazol-4-yl)-1,3,7-trihydropurine-2,6-dione;
1-(2-ethylcarboxyethyl)-8-(1-{[3-fluorophenyl]methyl}pyrazol-4-yl)-1,3,7-trihydropurine-2,6-dione;
1-ethenyl-8-(1-{[3-fluorophenyl]methyl}pyrazol-4-yl)-1,3,7-trihydropurine-2,6-dione;
1-cyclopentyl-8-(1-{[3-fluorophenyl]methyl}pyrazol-4-yl)-1,3,7-trihydropurine-2,6-dione;
1-(3-hydroxycyclopentyl)-8-(1-{[3-fluorophenyl]methyl}pyrazol-4-yl)-1,3,7-trihydropurine-2,6-dione;
1-cyclohexyl-8-(1-{[3-fluorophenyl]methyl}pyrazol-4-yl)-1,3,7-trihydropurine-2,6-dione;
1-cyclopropylmethyl-8-(1-{[3-fluorophenyl]methyl}pyrazol-4-yl)-1,3,7-trihydropurine-2,6-dione;
1-phenyl-8-(1-{[3-fluorophenyl]methyl}pyrazol-4-yl)-1,3,7-trihydropurine-2,6-dione;
1-(pyrid-3-yl)-8-(1-{[3-fluorophenyl]methyl}pyrazol-4-yl)-1,3,7-trihydropurine-2,6-dione;
1-(pyrid-3-ylmethyl)-8-(1-{[3-fluorophenyl]methyl}pyrazol-4-yl)-1,3,7-trihydropurine-2,6-dione;
1-(tetrahydrofuran-3-yl)-8-(1-{[3-fluorophenyl]methyl}pyrazol-4-yl)-1,3,7-trihydropurine-2,6-dione; and
1-(piperidin-4-yl)-8-(1-{[3-fluorophenyl]methyl}pyrazol-4-yl)-1,3,7-trihydropurine-2,6-dione.

D. Preparation of Other Compounds of Formula I

Similarly, following the procedure of 17A above, but optionally replacing 5,6-diamino-3-butyl-1,3-dihydropyrimidine-2,4-dione with other compounds of formula (25), and optionally replacing 1-benzylpyrazole-4-carboxylic acid with other compounds of formula (22), other compounds of Formula I are prepared.

EXAMPLE 18

Preparation of a Compound of Formula (31)

A. Preparation of a Compound of Formula (31) in which $R^2$ is Benzyl

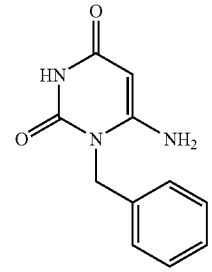

(31)

A solution of sodium ethoxide was prepared from sodium (1.53 g, 67 mmol) and dry ethanol (75 ml). To this solution was added benzyl urea (5.0 g, 33 mmol) and ethyl cyanoacetate (3.77 g, 33 mmol). This reaction mixture was stirred at reflux for 10 hours, cooled, and the precipitate filtered off and washed with ethanol. The precipitate was dissolved in water, and the pH adjusted to between 5 and 6 with hydrochloric acid. The solid material was filtered off, washed with water and dried under vacuum, to provide 6-amino-1-benzyl-1,3-dihydropyrimidine-2,4-dione, a compound of formula (31), which was used in the next reaction with no further purification.

B. Preparation of Other Compounds of Formula (31)

Similarly, following the procedure of 18A above, but replacing benzyl urea with other compounds of formula (30), the following compounds of formula (31) were prepared:
6-amino-1-methyl-1,3-dihydropyrimidine-2,4-dione;
6-amino-1-n-propyl-1,3-dihydropyrimidine-2,4-dione;
6-amino-1-n-butyl-1,3-dihydropyrimidine-2,4-dione; and
6-amino-1-isobutyl-1,3-dihydropyrimidine-2,4-dione.

C. Preparation of Other Compounds of Formula (31)

Similarly, following the procedure of 18A above, but replacing benzyl urea with other compounds of formula (30), other compounds of formula (31) are prepared.
6-amino-1-methyl-1,3-dihydropyrimidine-2,4-dione;
6-amino-1-isopropyl-1,3-dihydropyrimidine-2,4-dione;
6-amino-1-n-pentyl-1,3-dihydropyrimidine-2,4-dione;
6-amino-1-propylpentyl-1,3-dihydropyrimidine-2,4-dione;
6-amino-1-(2-phenylethyl)-1,3-dihydropyrimidine-2,4-dione;
6-amino-1-(2-methoxyethyl)-1,3-dihydropyrimidine-2,4-dione;
6-amino-1-(3-hydroxypropyl)-1,3-dihydropyrimidine-2,4-dione;
6-amino-1-(4-fluorobutyl)-1,3-dihydropyrimidine-2,4-dione;
6-amino-1-(2-ethylcarboxyethyl)-1,3-dihydropyrimidine-2,4-dione;
6-amino-1-ethenyl-1,3-dihydropyrimidine-2,4-dione;
6-amino-1-cyclopentyl-1,3-dihydropyrimidine-2,4-dione;
6-amino-1-(3-hydroxycyclopentyl)-1,3-dihydropyrimidine-2,4-dione;
6-amino-1-cyclohexyl-1,3-dihydropyrimidine-2,4-dione;
6-amino-1-cyclopropylmethyl-1,3-dihydropyrimidine-2,4-dione;
6-amino-1-phenyl-1,3-dihydropyrimidine-2,4-dione;
6-amino-1-(pyrid-3-yl)-1,3-dihydropyrimidine-2,4-dione;
6-amino-1-(pyrid-3-ylmethyl)-1,3-dihydropyrimidine-2,4-dione;
6-amino-1-(tetrahydrofuran-3-yl)-1,3-dihydropyrimidine-2,4-dione; and
6-amino-1-(piperidin-4-yl)-1,3-dihydropyrimidine-2,4-dione.

D. Preparation of Other Compounds of Formula (31)

Similarly, following the procedure of 18A above, but replacing benzyl urea with other compounds of formula (30), other compounds of formula (31) are prepared.

EXAMPLE 19

Preparation of a Compound of Formula (24)

A. Preparation of a Compound of Formula (24) in which $R^2$ is Benzyl

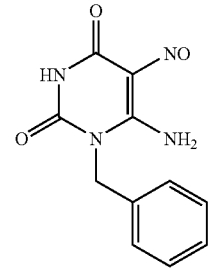

(24)

To a solution of 6-amino-1-benzyl-1,3-dihydropyrimidine-2,4-dione (2.0 g, 9.2 mmol) in a mixture of 15 ml of N,N-dimethylformamide and 5 ml of water at 90° C. was added sodium nitrite (1.27 g, 69 mmol). To this reaction mixture was added concentrated hydrochloric acid until there was no deepening of color, and the mixture was heated at 70° C. for 1 hour. The solvent was removed under reduced pressure, the residue dissolved in water, and concentrated hydrochloric acid added to produce a pH of 4.0. The precipitate was filtered off, washed with water, and dried under reduced pressure, to provide 6-amino-5-nitroso-1-benzyl-1,3-dihydropyrimidine-2,4-dione, a compound of formula (24).

B. Preparation of Other Compounds of Formula (24)

Similarly, following the procedure of 19A above, but replacing 6-amino-1-benzyl-1,3-dihydropyrimidine-2,4-dione with other compounds of formula (31), the following compounds of formula (24) were prepared:
6-amino-5-nitroso-1-methyl-1,3-dihydropyrimidine-2,4-dione;
6-amino-5-nitroso-1-n-propyl-1,3-dihydropyrimidine-2,4-dione;
6-amino-5-nitroso-1-n-butyl-1,3-dihydropyrimidine-2,4-dione; and
6-amino-5-nitroso-1-isobutyl-1,3-dihydropyrimidine-2,4-dione.

C. Preparation of Other Compounds of Formula (24)

Similarly, following the procedure of 19A above, but replacing 6-amino-1-benzyl-1,3-dihydropyrimidine-2,4-dione with other compounds of formula (31), the following compounds of formula (24) are prepared.
6-amino-5-nitroso-1-methyl-1,3-dihydropyrimidine-2,4-dione;
6-amino-5-nitroso-1-isopropyl-1,3-dihydropyrimidine-2,4-dione;
6-amino-5-nitroso-1-n-pentyl-1,3-dihydropyrimidine-2,4-dione;
6-amino-5-nitroso-1-propylpentyl-1,3-dihydropyrimidine-2,4-dione;
6-amino-5-nitroso-1-(2-phenylethyl)-1,3-dihydropyrimidine-2,4-dione;
6-amino-5-nitroso-1-(2-methoxyethyl)-1,3-dihydropyrimidine-2,4-dione;
6-amino-5-nitroso-1-(3-hydroxypropyl)-1,3-dihydropyrimidine-2,4-dione;

6-amino-5-nitroso-1-(4-fluorobutyl)-1,3-dihydropyrimidine-2,4-dione;
6-amino-5-nitroso-1-(2-ethylcarboxyethyl)-1,3-dihydropyrimidine-2,4-dione;
6-amino-5-nitroso-1-ethenyl-1,3-dihydropyrimidine-2,4-dione;
6-amino-5-nitroso-1-cyclopentyl-1,3-dihydropyrimidine-2,4-dione;
6-amino-5-nitroso-1-(3-hydroxycyclopentyl)-1,3-dihydropyrimidine-2,4-dione;
6-amino-5-nitroso-1-cyclohexyl-1,3-dihydropyrimidine-2,4-dione;
6-amino-5-nitroso-1-cyclopropylmethyl-1,3-dihydropyrimidine-2,4-dione;
6-amino-5-nitroso-1-phenyl-1,3-dihydropyrimidine-2,4-dione;
6-amino-5-nitroso-1-(pyrid-3-yl)-1,3-dihydropyrimidine-2,4-dione;
6-amino-5-nitroso-1-(pyrid-3-ylmethyl)-1,3-dihydropyrimidine-2,4-dione;
6-amino-5-nitroso-1-(tetrahydrofuran-3-yl)-1,3-dihydropyrimidine-2,4-dione; and
6-amino-5-nitroso-1-(piperidin-4-yl)-1,3-dihydropyrimidine-2,4-dione.

D. Preparation of Other Compounds of Formula (24)

Similarly, following the procedure of 19A above, but replacing 6-amino-1-benzyl-1,3-dihydropyrimidine-2,4-dione with other compounds of formula (31), other compounds of formula (24) are prepared.

EXAMPLE 20

Preparation of a Compound of Formula (21)

A. Preparation of a Compound of Formula (21) in which $R^2$ is Benzyl

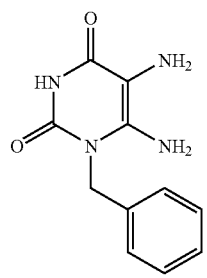

(21)

To a solution of 6-amino-5-nitroso-1-benzyl-1,3-dihydropyrimidine-2,4-dione (1.15 g, 4.7 mmol) in 12.5% aqueous ammonia (40 ml) at 70° C. was added sodium hydrosulfite (2.44 g, 14 mmol) in portions over 15 minutes. On cooling the reaction mixture in an ice bath the product precipitated out. It was filtered, washed with water, and dried under reduced pressure, to provide 5,6-diamino-1-benzyl-1,3-dihydropyrimidine-2,4-dione, a compound of formula (21).

B. Preparation of Other Compounds of Formula (21)

Similarly, following the procedure of 20A above, but replacing 6-amino-5-nitroso-1-benzyl-1,3-dihydropyrimidine-2,4-dione with other compounds of formula (23), the following compounds of formula (21) were prepared:
5,6-diamino 1-methyl-1,3-dihydropyrimidine-2,4-dione;
5,6-diamino 1-n-propyl-1,3-dihydropyrimidine-2,4-dione;
5,6-diamino-1-n-butyl-1,3-dihydropyrimidine-2,4-dione; and
5,6-diamino-1-isobutyl-1,3-dihydropyrimidine-2,4-dione.

C. Preparation of Other Compounds of Formula (21)

Similarly, following the procedure of 20A above, but replacing 6-amino-5-nitroso-1-benzyl-1,3-dihydropyrimidine-2,4-dione with other compounds of formula (23), the following compounds of formula (21) are prepared.
5,6-diamino-1-methyl-1,3-dihydropyrimidine-2,4-dione;
5,6-diamino-1-isopropyl-1,3-dihydropyrimidine-2,4-dione;
5,6-diamino-1-n-pentyl-1,3-dihydropyrimidine-2,4-dione;
5,6-diamino-1-propylpentyl-1,3-dihydropyrimidine-2,4-dione;
5,6-diamino-1-(2-phenylethyl)-1,3-dihydropyrimidine-2,4-dione;
5,6-diamino-1-(2-methoxyethyl)-1,3-dihydropyrimidine-2,4-dione;
5,6-diamino-1-(3-hydroxypropyl)-1,3-dihydropyrimidine-2,4-dione;
5,6-diamino-1-(4-fluorobutyl)-1,3-dihydropyrimidine-2,4-dione;
5,6-diamino-1-(2-ethylcarboxyethyl)-1,3-dihydropyrimidine-2,4-dione;
5,6-diamino-1-ethenyl-1,3-dihydropyrimidine-2,4-dione;
5,6-diamino-1-cyclopentyl-1,3-dihydropyrimidine-2,4-dione;
5,6-diamino-1-(3-hydroxycyclopentyl)-1,3-dihydropyrimidine-2,4-dione;
5,6-diamino-1-cyclohexyl-1,3-dihydropyrimidine-2,4-dione;
5,6-diamino-1-cyclopropylmethyl-1,3-dihydropyrimidine-2,4-dione;
5,6-diamino-1-phenyl-1,3-dihydropyrimidine-2,4-dione;
5,6-diamino-1-(pyrid-3-yl)-1,3-dihydropyrimidine-2,4-dione;
5,6-diamino-1-(pyrid-3-ylmethyl)-1,3-dihydropyrimidine-2,4-dione;
5,6-diamino-1-(tetrahydrofuran-3-yl)-1,3-dihydropyrimidine-2,4-dione; and
5,6-diamino-1-(piperidin-4-yl)-1,3-dihydropyrimidine-2,4-dione.

D. Preparation of Other Compounds of Formula (21)

Similarly, following the procedure of 20A above, but replacing 6-amino-5-nitroso-1-benzyl-1,3-dihydropyrimidine-2,4-dione with other compounds of formula (23), other compounds of formula (21) are prepared.

EXAMPLE 21

Preparation of a Compound of Formula I

A. Preparation of a Compound of Formula I where $R^1$ is Hydrogen, $R^2$ is Benzyl, $R^3$ is Hydrogen, X is 1,4-Pyrazolene, Y is Methylene, and Z is Phenyl

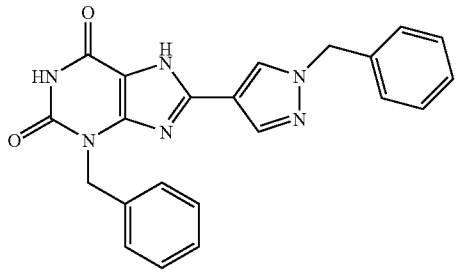

Formula I

A solution of 5,6-diamino-1-benzyl-1,3-dihydropyrimidine-2,4-dione (200 mg, 0.8 mmol), 1-benzylpyrazole-4-carboxylic acid (202 mg, 1 mmol) and 1-(3-dimethylaminopropyl)-3-ethylcarbodiimide hydrochloride (191 mg, 1 mmol) was dissolved in N,N-dimethylformamide and stirred for 16 hours. Solvent was then removed under reduced pressure, and the residue dissolved in hexamethyldisilazane (HMDS). To this solution was added ammonium sulfate, and the mixture was heated at 125° C. for 80 hours. Excess HMDS was removed under reduced: pressure, and the residue slurried with a mixture of 1:1 methanol and water. The solid was filtered off, washed with 1:1 methanol and water, and dried under reduced pressure, to provide 3-benzyl-8-[1-benzylpyrazol-4-yl]-1,3,7-trihydropurine-2,6-dione, a compound of Formula I.

B. Preparation of a Compound of Formula I where $R^1$ is Hydrogen, $R^3$ is Hydrogen, X is 1,4-Pyrazolene, Y is a Methylene, and Z is Phenyl, varying $R^2$, Similarly, following the procedure of 21A above, but replacing 5,6-diamino-1-benzyl-1,3-dihydropyrimidine-2,4-dione with other compounds of formula (21), the following compounds of Formula I were prepared:

3-n-propyl-8-[1-benzylpyrazol-4-yl]-1,3,7-trihydropurine-2,6-dione.

3-isobutyl-8-[1-benzylpyrazol-4-yl]-1,3,7-trihydropurine-2,6-dione;

3-benzyl-8-[1-benzylpyrazol-4-yl]-1,3,7-trihydropurine-2,6-dione;

3-n-butyl-8-[1-benzylpyrazol-4-yl]-1,3,7-trihydropurine-2,6-dione;

3-(2-methylpropyl)-8-[1-benzylpyrazol-4-yl]-1,3,7-trihydropurine-2,6-dione; and 3-methyl-8-[1-benzylpyrazol-4-yl]-1,3,7-trihydropurine-2,6-dione.

C. Preparation of a Compound of Formula I where $R^1$ is Hydrogen, Varying $R^2$, $R^3$ is Hydrogen, X is 1,4-Pyrazolene, Y is a Methylene, and Z is Phenyl Similarly, following the procedure of 21A above, but optionally replacing 5,6-diamino-1-benzyl-1,3-dihydropyrimidine-2,4-dione with other compounds of formula (21), and optionally replacing 1-benzylpyrazole-4-carboxylic acid with other compounds of formula (22), the following compounds of Formula I are prepared.

3-methyl-8-[1-benzylpyrazol-4-yl]-1,3,7-trihydropurine-2,6-dione.

3-isopropyl-8-[1-benzylpyrazol-4-yl]-1,3,7-trihydropurine-2,6-dione.

3-n-pentyl-8-[1-benzylpyrazol-4-yl]-1,3,7-trihydropurine-2,6-dione.

3-(1-propylpentyl)-8-[1-benzylpyrazol-4-yl]-1,3,7-trihydropurine-2,6-dione.

3-(2-phenyethyl)-8-[1-benzylpyrazol-4-yl]-1,3,7-trihydropurine-2,6-dione.

3-(2-methoxyethyl)-8-[1-benzylpyrazol-4-yl]-1,3,7-trihydropurine-2,6-dione.

3-(3-hydroxypropyl)-8-[1-benzylpyrazol-4-yl]-1,3,7-trihydropurine-2,6-dione.

3-(4-fluorobutyl)-8-[1-benzylpyrazol-4-yl]-1,3,7-trihydropurine-2,6-dione.

3-(2-ethylcarboxyethyl)-8-[1-benzylpyrazol-4-yl]-1,3,7-trihydropurine-2,6-dione.

3-ethenyl-8-[1-benzylpyrazol-4-yl]-1,3,7-trihydropurine-2,6-dione.

3-cyclopentyl-8-[1-benzylpyrazol-4-yl]-1,3,7-trihydropurine-2,6-dione.

3-(3-hydroxycyclopentyl)-8-[1-benzylpyrazol-4-yl]-1,3,7-trihydropurine-2,6-dione.

3-cyclohexyl-8-[1-benzylpyrazol-4-yl]-1,3,7-trihydropurine-2,6-dione.

3-cyclopropylmethyl-8-[1-benzylpyrazol-4-yl]-1,3,7-trihydropurine-2,6-dione.

3-phenyl-8-[1-benzylpyrazol-4-yl]-1,3,7-trihydropurine-2,6-dione.

3-(pyrid-3-yl)n-propyl-8-[1-benzylpyrazol-4-yl]-1,3,7-trihydropurine-2,6-dione.

3-(pyrid-3-ylmethyl)-8-[1-benzylpyrazol-4-yl]-1,3,7-trihydropurine-2,6-dione.

3-(tetrahydrofuran-3-yl)-8-[1-benzylpyrazol-4-yl]-1,3,7-trihydropurine-2,6-dione; and 3-(piperidin-4-yl)-8-[1-benzylpyrazol-4-yl]-1,3,7-trihydropurine-2,6-dione.

D. Preparation of a Compound of Formula I where $R^1$ is Hydrogen, Varying $R^2$, $R^3$ is Hydrogen, X is 1,4-Pyrazolene, Y is a Methylene, and Z is Phenyl Similarly, following the procedure of 21A above, but optionally replacing 5,6-diamino-1-benzyl-1,3-dihydropyrimidine-2,4-dione with other compounds of formula (21), and optionally replacing I-benzylpyrazole-4-carboxylic acid with other compounds of formula (22), other compounds of Formula I are prepared.

EXAMPLE 22

Preparation of a Compound of Formula (33)

A. Preparation of a Compound of Formula (33) in which $R^1$ is n-Butyl and $R^2$ is Methyl

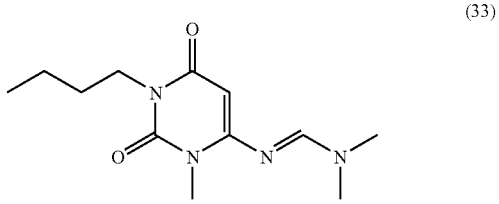

(33)

A suspension of 6-amino-1-methyl uracil (3.0 g) in anhydrous N,N-dimethylformamide dimethylacetal (10 ml) and N,N-dimethylacetamide (50 ml) was warmed at 40° C. until the disappearance of starting material was observed (60 min). Potassium carbonate (10 g) and n-butyl bromide (7.8 g) were then added, and the reaction mixture was stirred at 80° C. for 16 hours. The reaction mixture was cooled to room temperature, filtered, the solvents were evaporated and the product of formula (33), 6-[1-aza-2-(dimethylamino)vinyl]-3-butyl-1-methyl-1,3-dihydropyrimidine-2,4-dione, was used as such for the next reaction.

B. Preparation of Compounds of Formula (33). Varying $R^1$ and $R^2$

Similarly, following the procedure of 22A above, but optionally replacing 6-amino-1-methyluracil with other compounds of formula (31), and optionally replacing n-butyl bromide with other alkyl halides, the following compounds of formula (33) were prepared:

6-[1-aza-2-(dimethylamino)vinyl]-1-methyl-1,3-dihydropyrimidine-2,4-dione;
6-[1-aza-2-(dimethylamino)vinyl]-1-methyl-3-ethyl-1,3-dihydropyrimidine-2,4-dione;
6-[1-aza-2-(dimethylamino)vinyl]-1-methyl-3-propyl-1,3-dihydropyrimidine-2,4-dione;
6-[1-aza-2-(dimethylamino)vinyl]-1-ethyl-3-prop-2-ynyl-1,3-dihydropyrimidine-2,4-dione;
6-[1-aza-2-(dimethylamino)vinyl]-1-ethyl-3-propyl-1,3-dihydropyrimidine-2,4-dione;
6-[1-aza-2-(dimethylamino)vinyl]-1-methyl-3-butyl-1,3-dihydropyrimidine-2,4-dione;
6-[1-aza-2-(dimethylamino)vinyl]-1-methyl-3-sec-butyl-1,3-dihydropyrimidine-2,4-dione;
6-[1-aza-2-(dimethylamino)vinyl]-1-methyl-3-cyclopropylmethyl-1,3-dihydropyrimidine-2,4-dione;
6-[1-aza-2-(dimethylamino)vinyl]-1-ethyl-3-cyclopropylmethyl-1,3-dihydropyrimidine-2,4-dione;
6-[1-aza-2-(dimethylamino)vinyl]-1-ethyl 3-sec butyl-1,3-dihydropyrimidine-2,4-dione; and
6-[1-aza-2-(dimethylamino)vinyl]-1-ethyl-3-n butyl-1,3-dihydropyrimidine-2,4-dione.

C. Preparation of Compounds of Formula (33), Varying $R^1$ and $R^2$

Similarly, following the procedure of 22A above, but optionally replacing 6-amino-1-methyluracil with other compounds of formula (31), and optionally replacing n-butyl bromide with other alkyl halides, other compounds of formula (33) are prepared.

EXAMPLE 23

Preparation of a Compound of Formula (34)

A. Preparation of a Compound of Formula (34) in which $R^1$ is n-Butyl and $R^2$ is Methyl

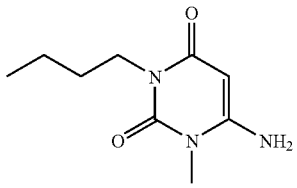

(34)

The 6-[(1E)-1-aza-2-(dimethylamino)vinyl]-3-butyl-1-methyl-1,3-dihydropyrimidine-2,4-dione (4.0 g) obtained in Example 22A was suspended in methanol. To this suspension was added aqueous ammonium hydroxide, and the reaction mixture was stirred at room temperature for 48 hours. After starting material was no longer observed, the solvents were removed under reduced pressure, the residue was suspended in water, and the precipitate was filtered, washed with water, and dried under reduced pressure, to provide crude 6-amino-3-butyl-1-methyl-1,3-dihydropyrimidine-2,4-dione, which was used as such in the next reaction.

B. Preparation of Compounds of Formula (34), Varying $R^1$ and $R^2$

Similarly, following the procedure of 23A above, but replacing 6-[(1E)-1-aza-2-(dimethylamino)vinyl]-3-butyl-1-methyl-1,3-dihydropyrimidine-2,4-dione with other compounds of formula (33), the following compounds of formula (34) were prepared:

6-amino-1-methyl-1,3-dihydropyrimidine-2,4-dione;
6-amino-1-methyl-3-ethyl-1,3-dihydropyrimidine-2,4-dione;
6-amino-1-methyl-3-propyl-1,3-dihydropyrimidine-2,4-dione;
6-amino-1-ethyl-3-(prop-2-ynyl)-1,3-dihydropyrimidine-2,4-dione;
6-amino-1-ethyl-3-propyl-1,3-dihydropyrimidine-2,4-dione;
6-amino-1-methyl-3-sec-butyl-1,3-dihydropyrimidine-2,4-dione;
6-amino-1-methyl-3-cyclopropylmethyl-1,3-dihydropyrimidine-2,4-dione;
6-amino-1-ethyl-3-cyclopropylmethyl-1,3-dihydropyrimidine-2,4-dione;
6-amino-1-ethyl 3-sec butyl-1,3-dihydropyrimidine-2,4-dione; and
6-amino-1-ethyl-3-n butyl-1,3-dihydropyrimidine-2,4-dione.

C. Preparation of Compounds of Formula (34), Varying $R^1$ and $R^2$

Similarly, following the procedure of 23A above, but replacing 6-[(1E)-1-aza-2-(dimethylamino)vinyl]-3-butyl-1-methyl-1,3-dihydropyrimidine-2,4-dione with other compounds of formula (33), other compounds of formula (34) are prepared.

EXAMPLE 24

Preparation of a Compound of Formula I

A. Preparation of a Compound of Formula I where $R^1$ is n-Butyl, $R^2$ is Methyl, X is 1,4-Pyrazolene, Y is Methylene, and Z is 3-Fluorophenyl

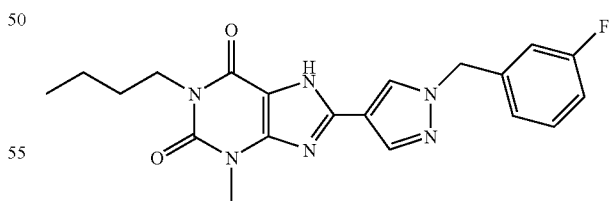

The compound of formula (34) is then converted into a compound of Formula I in the same manner as shown for the conversion of a compound of formula (23) in Examples 14, 15, 16, and 17. That is, reaction with sodium nitrite to a 5-nitroso-6-amino derivative, which is reduced to a 5,6-diamino derivative, which in turn is reacted with an appropriately substituted carboxylic acid of formula Z-Y—X—$CO_2H$ to provide a compound of Formula I. In this manner, the following compounds were prepared:

1-butyl-3-methyl-8-{1-[(3-fluorophenyl)methyl]pyrazol-4-yl}-1,3,7-trihydropurine-2,6-dione;
1-methyl-3-sec-butyl-8-pyrazol-4-yl-1,3,7-trihydropurine-2,6-dione;
3-methyl-1-propyl-8-[1-benzylpyrazol-4-yl]-1,3,7-trihydropurine-2,6-dione;
3-ethyl-1-(prop-2-ynyl)-8-[1-benzylpyrazol-4-yl]-1,3,7-trihydropurine-2,6-dione;
3-ethyl-1-propyl-8-[1-benzylpyrazol-4-yl]-1,3,7-trihydropurine-2,6-dione;
1-sec-butyl-3-methyl-8-[1-benzylpyrazol-4-yl]-1,3,7-trihydropurine-2,6-dione;
1-cyclopropylmethyl-3-methyl-8-[1-benzylpyrazol-4-yl]-1,3,7-trihydropurine-2,6-dione;
3-ethyl-1-propyl-8-{1-[(3-trifluoromethylphenyl)methyl]pyrazol-4-yl}-1,3,7-trihydropurine-2,6-dione;
3-ethyl-1-propyl-8-(pyrazol-4-yl)-1,3,7-trihydropurine-2,6-dione;
1-cyclopropylmethyl-3-ethyl-8-{1-[(3-trifluoromethylphenyl)methyl]pyrazol-4-yl}-1,3,7-trihydropurine-2,6-dione;
ethyl 2-[4-(2,6-dioxo-1,3-dipropyl(1,3,7-trihydropurin-8-yl))pyrazolyl]-2-phenylacetate;
1-cyclopropylmethyl-3-methyl-8-{1-[(3-trifluoromethylphenyl)methyl]pyrazol-4-yl}-1,3,7-trihydropurine-2,6-dione;
3-methyl-1-propyl-8-{1-[(3-trifluoromethylphenyl)methyl]pyrazol-4-yl}-1,3,7-trihydropurine-2,6-dione;
3-methyl-1-propyl-8-{1-[(3-fluorophenyl)methyl]pyrazol-4-yl}-1,3,7-trihydropurine-2,6-dione;
1-cyclopropylmethyl-3-methyl-8-{1-[(3-fluorophenyl)methyl]pyrazol-4-yl}-1,3,7-trihydropurine-2,6-dione;
1-cyclopropylmethyl-3-ethyl-8-pyrazol-4-yl-1,3,7-trihydropurine-2,6-dione;
1-sec-butyl-3-ethyl-8-{1-[(3-fluorophenyl)methyl]pyrazol-4-yl}-1,3,7-trihydropurine-2,6-dione;
1-butyl-3-methyl-8-[1-benzylpyrazol-4-yl]-1,3,7-trihydropurine-2,6-dione;
1-butyl-3-methyl-8-(pyrazol-4-yl)-1,3,7-trihydropurine-2,6-dione;
1-sec-butyl-3-ethyl-8-[1-benzylpyrazol-4-yl]-1,3,7-trihydropurine-2,6-dione;
1-sec-butyl-3-methyl-8-(pyrazol-4-yl)-1,3,7-trihydropurine-2,6-dione;
1-sec-butyl-3-methyl-8-{1-[(3-trifluoromethylphenyl)methyl]pyrazol-4-yl}-1,3,7-trihydropurine-2,6-dione;
1-sec-butyl-3-methyl-8-{1-[(3-fluorophenyl)methyl]pyrazol-4-yl}-1,3,7-trihydropurine-2,6-dione;
1-ethyl-3-methyl-8-{1-[(3-fluorophenyl)methyl]pyrazol-4-yl}-1,3,7-trihydropurine-2,6-dione;
1-ethyl-3-methyl-8-{1-[(3-trifluoromethylphenyl)methyl]pyrazol-4-yl}-1,3,7-trihydropurine-2,6-dione;
1-sec-butyl-3-ethyl-8-{1-[(3-fluorophenyl)methyl]pyrazol-4-yl}-1,3,7-trihydropurine-2,6-dione;
1-cyclopropylmethyl-3-ethyl-8-{1-[(3-fluorophenyl)methyl]pyrazol-4-yl}-1,3,7-trihydropurine-2,6-dione.
1-butyl-3-methyl-8-(1-{[3-(trifluoromethyl)phenyl]methyl}pyrazol-4-yl)-1,3,7-trihydropurine-2,6-dione;
3-ethyl-1-(2-methylpropyl)-8-pyrazol-4-yl-1,3,7-trihydropurine-2,6-dione;
1-(cyclopropylmethyl)-3-ethyl-8-{1-[(3-fluorophenyl)methyl]pyrazol-4-yl}-1,3,7-trihydropurine-2,6-dione;
1-ethyl-3-methyl-8-pyrazol-4-yl-1,3,7-trihydropurine-2,6-dione;
1-ethyl-3-methyl-8-[1-benzylpyrazol-4-yl]-1,3,7-trihydropurine-2,6-dione;
3-ethyl-1-propyl-8-[1-({5-[4-(trifluoromethyl)phenyl](1,2,4-oxadiazol-3-yl)}methyl)pyrazol-4-yl]-1,3,7-trihydropurine-2,6-dione;
3-ethyl-1-propyl-8-[1-({5-[4-(trifluoromethyl)phenyl]isoxazol-3-yl}methyl)pyrazol-4-yl]-1,3,7-trihydropurine-2,6-dione;
3-ethyl-1-propyl-8-[1-(2-pyridylmethyl)pyrazol-4-yl]-1,3,7-trihydropurine-2,6-dione;
8-(1-{[5-(4-chlorophenyl)isoxazol-3-yl]methyl}pyrazol-4-yl)-3-ethyl-1-propyl-1,3,7-trihydropurine-2,6-dione;
8-(1-{[5-(4-chlorophenyl)(1,2,4-oxadiazol-3-yl)]methyl}pyrazol-4-yl)-3-ethyl-1-propyl-1,3,7-trihydropurine-2,6-dione;
3-({4-[1-(cyclopropylmethyl)-3-methyl-2,6-dioxo-1,3,7-trihydropurin-8-yl]pyrazolyl}methyl)benzenecarbonitrile;
8-(1-{[3-(4-chlorophenyl)(1,2,4-oxadiazol-5-yl)]methyl}pyrazol-4-yl)-3-ethyl-1-propyl-1,3,7-trihydropurine-2,6-dione;
3-ethyl-8-{1-[(5-phenylisoxazol-3-yl)methyl]pyrazol-4-yl}-1-propyl-1,3,7-trihydropurine-2,6-dione;
3-ethyl-1-propyl-8-(1-{[6-(trifluoromethyl)(3-pyridyl)]methyl}pyrazol-4-yl)-1,3,7-trihydropurine-2,6-dione;
3-{[4-(3-ethyl-2,6-dioxo-1-propyl-1,3,7-trihydropurin-8-yl)pyrazolyl]methyl}-benzenecarbonitrile;
3-ethyl-1-propyl-8-{1-[(3-(1H-1,2,3,4-tetraazol-5-yl)phenyl)methyl]pyrazol-4-yl}-1,3,7-trihydropurine-2,6-dione;
3-ethyl-8-{1-[(6-methyl(3-pyridyl))methyl]pyrazol-4-yl}-1-propyl-1,3,7-trihydroprine-2,6-dione;
1-(cyclopropylmethyl)-3-ethyl-8-(1-{[6-(trifluoromethyl)(3-pyridyl)]methyl}pyrazol-4-yl)-1,3,7-trihydropurine-2,6-dione;
3-ethyl-1-(2-methylpropyl)-8-(1-{[6-(trifluoromethyl)(3-pyridyl)]methyl}pyrazol-4-yl)-1,3,7-trihydropurine-2,6-dione; and
8-[1-(2-(1H-1,2,3,4-tetraazol-5-yl)ethyl)pyrazol-4-yl]-1-(cyclopropylmethyl)-3-methyl-1,3,1-trihydropurine-2,6-dione.

EXAMPLE 25

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 26

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 27

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 28

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 29

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 30

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 31

A subcutaneous formulation may be prepared as follows:

| Ingredient | Quantity |
|---|---|
| Active Ingredient | 5.0 mg |
| Corn Oil | 1.0 mL |

EXAMPLE 32

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 33

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60) C with stirring. A sufficient quantity of water at 60) C is then added with vigorous stirring to emulsify the ingredients, and water then added q.s. 100 g.

EXAMPLE 34

Sustained Release Composition

| Ingredient | Weight Range (%) | Preferred Range (%) | Most Preferred |
|---|---|---|---|
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit®E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 35

$A_{2B}$ Adenosine Receptor Assays

Methods

Radioligand binding for $A_{2B}$ adenosine receptor. Human $A_{2B}$ adenosine receptor cDNA was stably transfected into HEK-293 cells (referred to as HEK-$A_{2B}$ cells). Monolayer of HEK-$A_{2B}$ cells were washed with PBS once and harvested in a buffer containing 10 mM HEPES (pH 7.4), 10 mM EDTA and protease inhibitors. These cells were homogenized in polytron for 1 minute at setting 4 and centrifuged at 29000 g for 15 minutes at 4° C. The cell pellets were washed once with a buffer containing 10 mM HEPES (pH7.4), 1 mM EDTA and protease inhibitors, and were resuspended in the same buffer supplemented with 10% sucrose. Frozen aliquots were kept at −80° C. Competition assays were started by mixing 10 nM $^3$H-ZM214385 (Tocris Cookson) with various concentrations of test compounds and 50 μg membrane proteins in TE buffer (50 mM Tris and 1 mM EDTA) supplemented with 1 Unit/mL adenosine deaminase. The assays were incubated for 90 minutes, stopped by filtration using Packard Harvester and washed four times with ice-cold TM buffer (10 mM Tris, 1 mM MgC12, pH 7.4). Non specific binding was determined in the presence of 10 μM ZM214385. The affinities of compounds (i.e. Ki values) were calculated using GraphPad software.

Radioliand binding for other adenosine receptors. Human $A_1$, $A_{2A}$, $A_3$ adenosine receptor cDNAs were stably transfected into either CHO or HEK-293 cells (referred to as CHO-A1, HEK-A2A, CHO-A3). Membranes were prepared from these cells using the same protocol as described above. Competition assays were started by mixing 0.5 nM $^3$H-CPX (for CHO-A1), 2 nM $^3$H-ZM214385 (HEK-A2A) or 0.1 nM $^{125}$I-AB-MECA (CHO-A3) with various concentrations of test compounds and the perspective membranes in TE buffer (50 mM Tris and 1 mM EDTA fo CHO-A1 and HEK-A2A) or TEM buffer (50 mM Tris, 1 mM EDTA and 10 mM $MgCl_2$ for CHO-A3) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 1 μM CPX (CHO-A1), 1 μM ZM214385 (HEK-A2A) and 1 μM IB-MECA (CHO-A3). The affinities of compounds (i.e. Ki values) were calculated using GraphPad software.

cAMP measurements. Monolayer of transfected cells were collected in PBS containing 5 mM EDTA. Cells were washed once with DMEM and resuspended in DMEM containing 1. Unit/mL adenosine deaminase at a density of 100,000-500,000 cells/ml. 100 μl of the cell suspension was mixed with 25 μl containing various agonists and/or antagonists and the reaction was kept at 37° C. for 15 minutes. At the end of 15 minutes, 125 μl 0.2N HCl was added to stop the reaction. Cells were centrifuged for 10 minutes at 1000 rpm. 100 μl of the supernatant was removed and acetylated. The concentrations of cAMP in the supernatants were measured using the direct cAMP assay from Assay Design.

$A_{2A}$ and $A_{2B}$ adenosine receptors are coupled to Gs proteins and thus agonists for $A_{2A}$ adenosine receptor (such as CGS21680) or for $A_{2B}$ adenosine receptor (such as NECA) increase the cAMP accumulations whereas the antagonists to these receptors prevent the increase in cAMP accumulations-induced by the agonists. $A_1$ and $A_3$ adenosine receptors are coupled to Gi proteins and thus agonists for $A_1$ adenosine receptor (such as CPA) or for $A_3$ adenosine receptor (such as IB-MECA) inhibit the increase in cAMP accumulations-induced by forskolin. Antagonists to $A_1$ and $A_3$ receptors prevent the inhibition in cAMP accumulations.

The compounds of the invention were shown to be A₂B-antagonists by the above tests.

Compounds of the invention were also tested in a mouse model for asthma, using the procedures disclosed in U.S. Pat. No. 6,387,913, the relevant portion of which is hereby incorporated by reference, and shown to be efficacious.

What is claimed is:

1. A compound of the Formula I or Formula II:

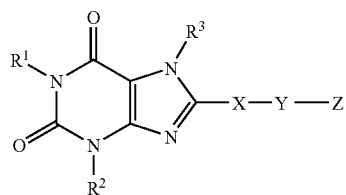

Formula I

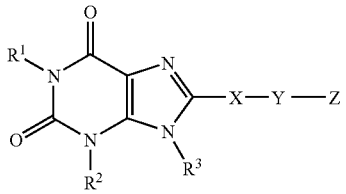

Formula II wherein:
R¹ and R² are independently chosen from hydrogen or loweralkyl;
R³ hydrogen,;
X is five or six membered monocyclic arylene or heteroarylene that is attached to the purine ring at a carbon atom;
Y is a covalent bond or alkylene in which one carbon atom can be optionally replaced by —O—, —S—, or —NH—; and
Z is optionally substituted monocyclic aryl or optionally substituted monocyclic heteroaryl.

2. The compound of claim 1, wherein,
X is phenylene or pyrazolene,
Y is lower alkylene in which one carbon atom can be optionally replaced by —O—, —S—, or —NH—, and
Z is optionally substituted phenyl, optionally substituted oxadiazolyl, optionally substituted isoxazolyl, or optionally substituted pyridyl.

3. The compound of claim 2, wherein R¹ is lower alkyl and R² is hydrogen.

4. The compound of claim 2, wherein X is optionally substituted 1,4-pyrazolene.

5. The compound of claim 2, wherein Z is optionally substituted phenyl.

6. The compound of claim 2, wherein Z is optionally substituted oxadiazolyl.

7. The compound of claim 2, wherein Z is optionally substituted pyridyl.

8. The compound of claim 2, wherein Z is optionally substituted isoxazolyl.

9. The compound of claim 2, wherein R¹ is hydrogen and R² is lower alkyl.

10. The compound of claim 2, wherein R¹ and R² are independently lower alkyl.

11. The compound of claim 2, wherein X is phenylene.

12. The compound of claim 2, wherein Y is methylene.

13. The compound of claim 2, wherein Y is —O—CH₂—.

14. The compound of claim 1, wherein Y is a covalent bond.

15. A pharmaceutical composition comprising a therapeutically effective amount of a compound of claim 1 and a pharmaceutically acceptable carrier.

* * * * *